United States Patent
Schneck et al.

(10) Patent No.: US 11,939,595 B2
(45) Date of Patent: Mar. 26, 2024

(54) NANOSCALE ARTIFICIAL ANTIGEN PRESENTING CELLS

(71) Applicant: The Johns Hopkins University, Baltimore, MD (US)

(72) Inventors: Jonathan Schneck, Baltimore, MD (US); Mathias Oelke, Baltimore, MD (US); Karlo Perica, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1097 days.

(21) Appl. No.: 16/548,953

(22) Filed: Aug. 23, 2019

(65) Prior Publication Data

US 2020/0095546 A1 Mar. 26, 2020

Related U.S. Application Data

(62) Division of application No. 14/775,855, filed as application No. PCT/US2014/025889 on Mar. 13, 2014, now Pat. No. 10,435,668.

(60) Provisional application No. 61/942,797, filed on Feb. 21, 2014, provisional application No. 61/786,135, filed on Mar. 14, 2013.

(51) Int. Cl.
| | |
|---|---|
| *C12N 5/0783* | (2010.01) |
| *A61K 39/00* | (2006.01) |
| *A61K 39/39* | (2006.01) |
| *A61K 39/44* | (2006.01) |
| *A61K 47/68* | (2017.01) |
| *A61K 47/69* | (2017.01) |
| *C12N 5/0781* | (2010.01) |
| *A61K 9/51* | (2006.01) |
| *A61K 35/17* | (2015.01) |

(52) U.S. Cl.
CPC ............ *C12N 5/0635* (2013.01); *A61K 39/39* (2013.01); *A61K 39/44* (2013.01); *A61K 47/6849* (2017.08); *A61K 47/6939* (2017.08); *C12N 5/0636* (2013.01); *A61K 35/17* (2013.01); *A61K 2039/5158* (2013.01); *A61K 2039/55555* (2013.01); *A61K 2039/572* (2013.01); *A61K 2039/60* (2013.01); *A61K 2039/605* (2013.01); *A61K 2039/6087* (2013.01); *A61K 2039/625* (2013.01); *A61K 2039/64* (2013.01); *C12N 2501/50* (2013.01); *C12N 2501/51* (2013.01); *C12N 2529/00* (2013.01); *C12N 2533/10* (2013.01); *C12N 2533/70* (2013.01)

(58) Field of Classification Search
None
See application file for complete search history.

(56) References Cited

U.S. PATENT DOCUMENTS

| | | | |
|---|---|---|---|
| 6,015,884 A | 1/2000 | Schneck et al. | |
| 6,140,113 A | 10/2000 | Schneck et al. | |
| 6,268,411 B1 | 7/2001 | Schneck et al. | |
| 6,448,071 B1 | 9/2002 | Schneck et al. | |
| 6,458,354 B1 | 10/2002 | Schneck et al. | |
| 6,734,013 B2 | 5/2004 | Schneck et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,541,184 B2 | 6/2009 | Berenson et al. | |
| 7,572,631 B2 | 8/2009 | Berenson et al. | |
| 7,973,137 B1 | 7/2011 | Schneck et al. | |
| 10,098,939 B2 * | 10/2018 | Schneck ................ C07K 16/00 | |
| 10,987,412 B2 * | 4/2021 | Schneck ............ G01N 33/54326 | |
| 11,007,220 B2 * | 5/2021 | Strober .................... A61P 13/12 | |
| 2002/0131960 A1 | 9/2002 | Sadelain et al. | |
| 2004/0115216 A1 | 6/2004 | Schneck et al. | |
| 2004/0224402 A1 | 11/2004 | Bonyhadi et al. | |
| 2010/0008920 A1 | 1/2010 | Schneck et al. | |
| 2010/0284965 A1 | 11/2010 | Fahmy et al. | |
| 2011/0293637 A1 | 12/2011 | Hacohen et al. | |
| 2015/0366991 A1 | 12/2015 | Schneck et al. | |
| 2016/0000829 A1 | 1/2016 | June et al. | |
| 2016/0051698 A1 | 2/2016 | Schneck et al. | |

FOREIGN PATENT DOCUMENTS

| | | |
|---|---|---|
| WO | 2009094273 | 7/2009 |
| WO | WO202041968 | * 3/2020 |

OTHER PUBLICATIONS

Durai et al (Cancer. Immunol. Immunother. 2009, 58: 209-220) (Year: 2009).*
Rapoport et al (Blood, 2011, 117(3): 788-797) (Year: 2011).*
Niosh, 2018, pp. 1-3 (Year: 2018).*
Nanowerk , 2023, pp. 1-8 (Year: 2023).*
Bayda et al (Molecules, 2019, 25, 112, doi: 10.3390/molecules 25010112, pp. 1-15) (Year: 2019).*
Pollack et al., "Tetramer guided, cell sorter assisted production of clinical grade autologous NY-ESO-1 specific CD8+ T cells," Journal for Immuno Therapy of Cancer 2014, vol. 2 No. 36, pp. 1-10.
Zappasodi, et al., "The effect of artificial antigen-presenting cells with preclustered anti-CD28/-CD3/-LFA-1 monoclonal antibodies on the induction of ex vivo expansion of functional human antitumor T cells," Haematologica, 2008, vol. 93, No. 10, pp. 1523-1534.
Greten, et al., Development and Use of Multimeric Major Histocompatibility Complex Molecules, Clinical and Diagnostic Laboratory Immunology, 2002, pp. 216-220, vol. 9, No. 2.
Perica, et al., "Magnetic field-induced T cell receptor clustering by nanoparticles enhances T cell activation and stimulates antitumor activity", ACS Nano, Epub. Feb. 24, 2014, vol. 8, No. 3, pp. 2252-2260.

(Continued)

*Primary Examiner* — G. R. Ewoldt
*Assistant Examiner* — Marianne DiBrino
(74) *Attorney, Agent, or Firm* — Morgan, Lewis & Bockius LLP

(57) ABSTRACT

This disclosure provides nano-scale Artificial Antigen Presenting Cells (aAPC), which deliver stimulatory signals to lymphocytes, including T-helper lymphocytes, for use as a powerful tool for immunotherapy.

16 Claims, 41 Drawing Sheets

Specification includes a Sequence Listing.

(56) References Cited

OTHER PUBLICATIONS

Quintarelli, et al., "Cytotoxic T lymphocytes directed to the preferentially expressed antigen of melanoma (PRAME) target chronic myeloid leukemia," Blood, 2008, vol. 112, No. 5, pp. 1876-1885.
Turtle, et al., "Artificial Antigen Presenting Cells for use in Adoptive Immunotherapy," Cancer J., 2010, vol. 16, No. 4, pp. 374-381.
Perica, et al., "Nanoscale artificial antigen presenting cells for T cell immunitherapy", Nanomedicine, Epub. Jul. 24, 2013, vol. 10 No. 1 pp. 119-129.
Saengruengrit et al (J. Colloid and Interface Science, 2018, 520: 101-111) (Year: 2018).
Dal Porto et al (PNAS 1993, 90-6671-6675) (Year: 1993).
Yee et al (J. Immunol. 1999, 162: 2227-2234) (Year: 1999).
Greten and Korangy (Nagorsen and Marincola, Eds., Analyzing T cell responses, Chapter 13-MHC-Ig dimeric molecules, 2005: 227 -238) (Year: 2005).
Delke & Schneck, "Overview of a HLA-Ig based "Lego-like system" for T cell monitoring, modulation and expansion," Immunologic Research, vol. 47, No. 1-3, Jul. 2010, pp. 248-256.
Steen Block et al., "A comprehensive platform for ex vivo T-cell expansion based on biodegradable polymeric artificial antigen-presenting cells," Molecular Therapy, vol. 16, No. 4, Apr. 1, 2008, pp. 765-772.
Chiu et al., "HLA-Ig based artificial antigen presenting cells for efficient ex vivo expansion of human CTL," Journal of Visualized Experments, Apr. 11, 2011, vol. 50, pp. 1-4.
Perica et al., "Nanoscale artificial antigen presenting cells for T cell immunotherapy," Nanomedicine, Jul. 24, 2013, vol. 10, No. 1, pp. 119-129, published online Jul. 24, 2013.

\* cited by examiner

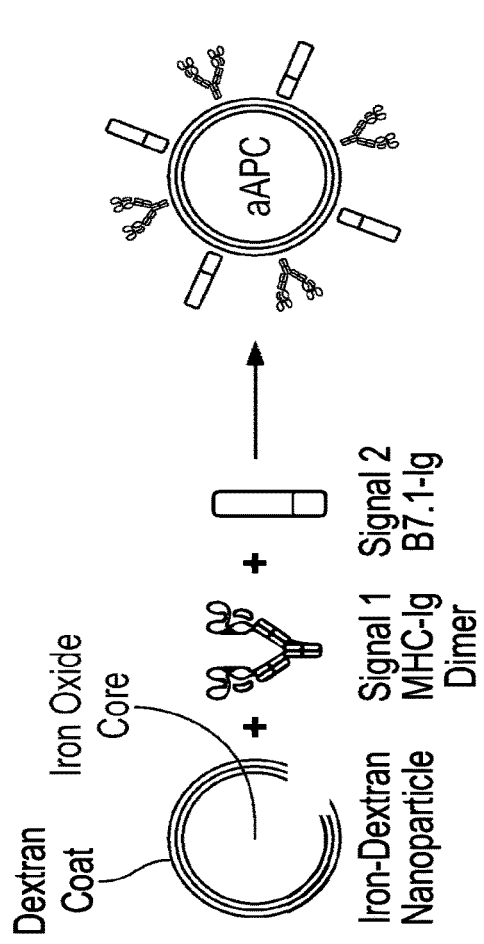
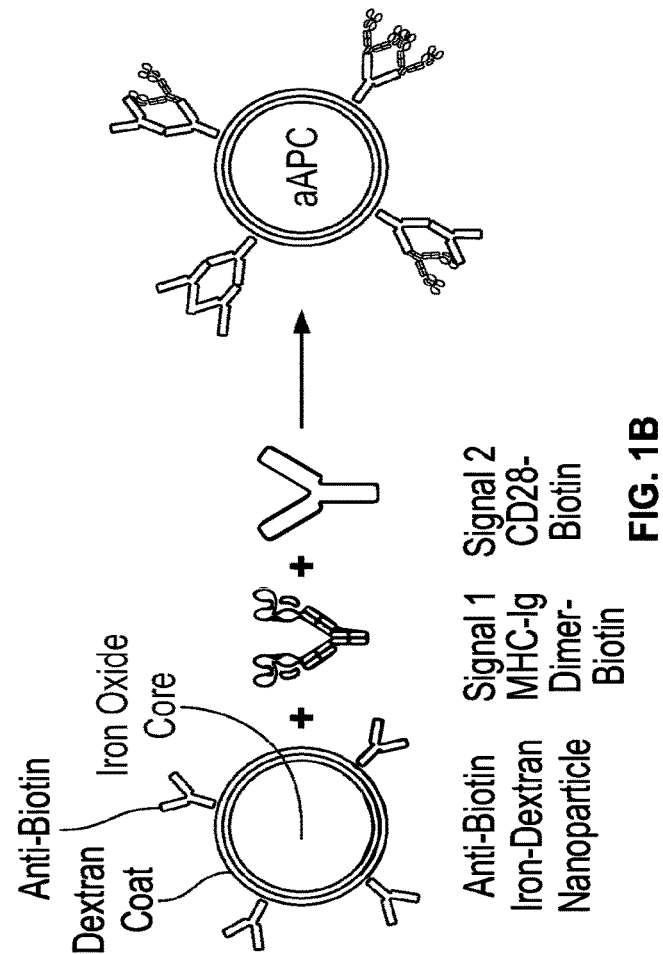
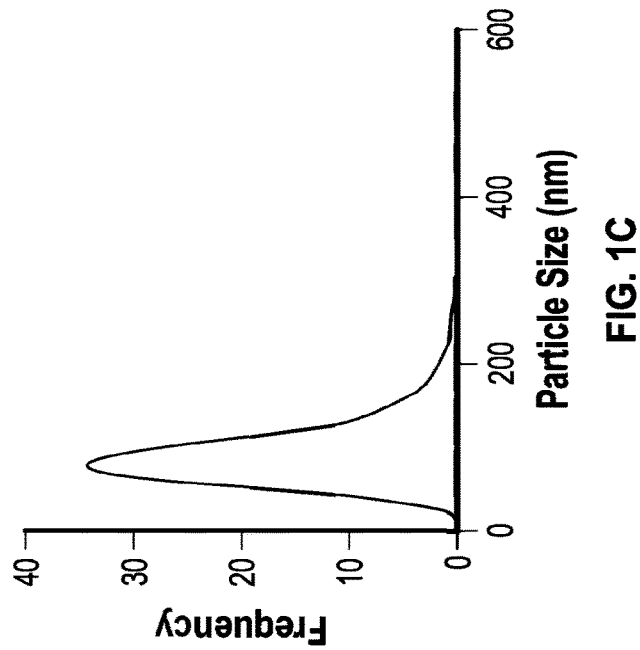

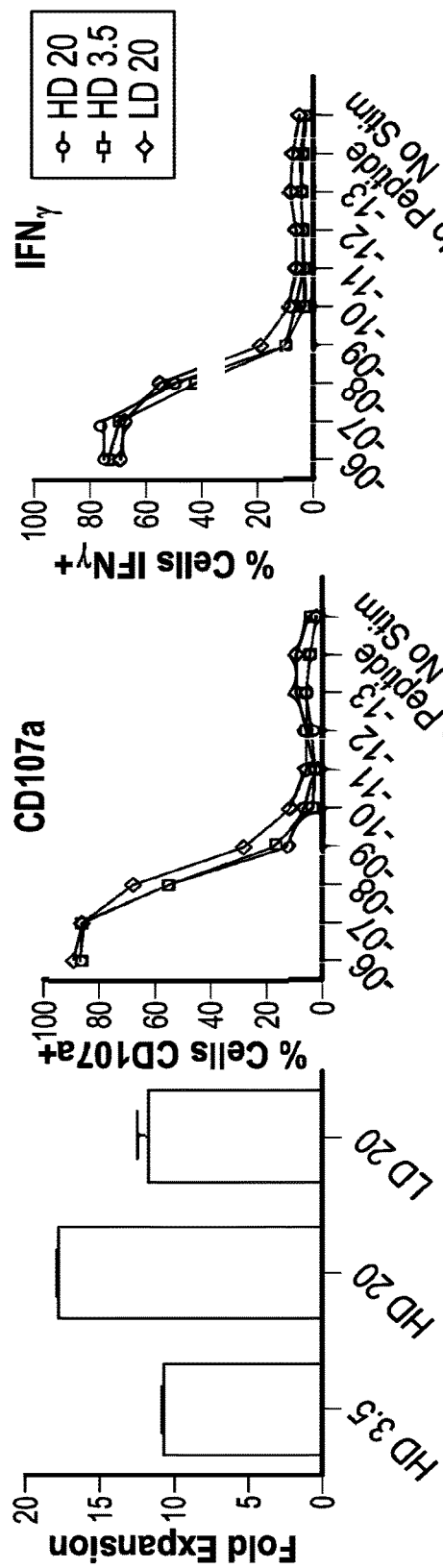
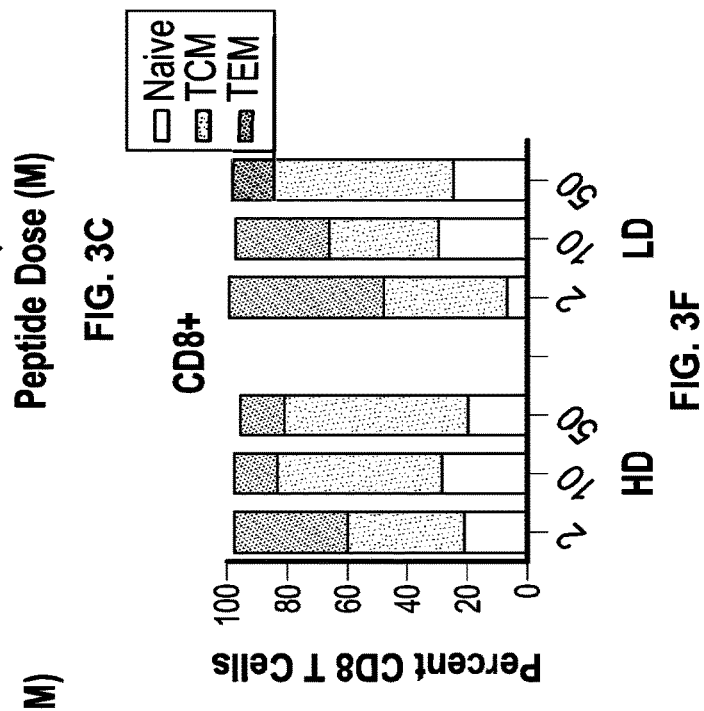
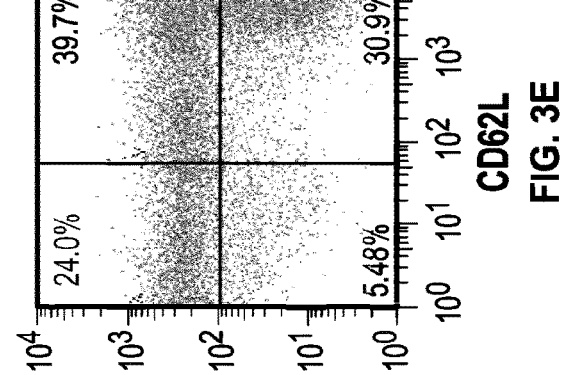
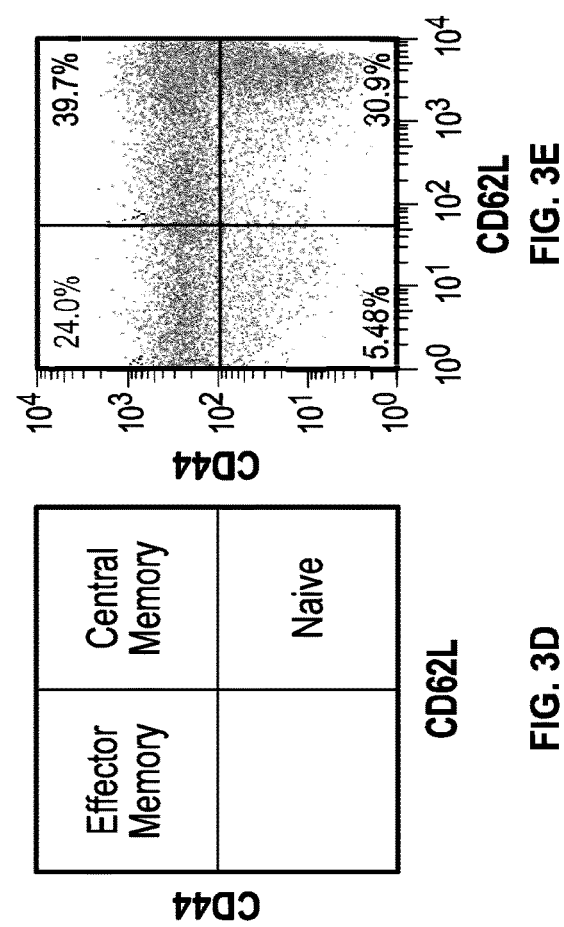
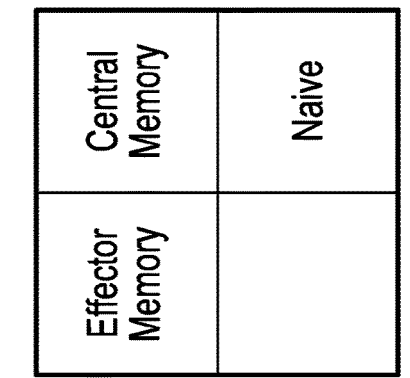
FIG. 3A  FIG. 3B  FIG. 3C  FIG. 3D  FIG. 3E  FIG. 3F

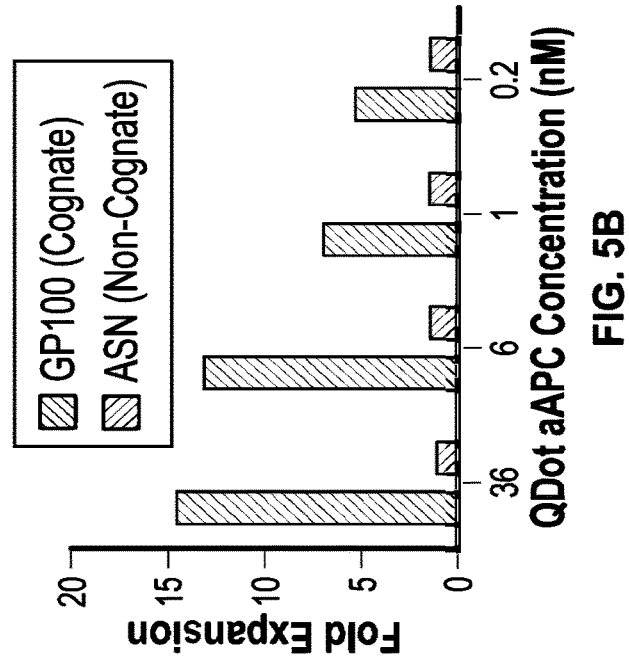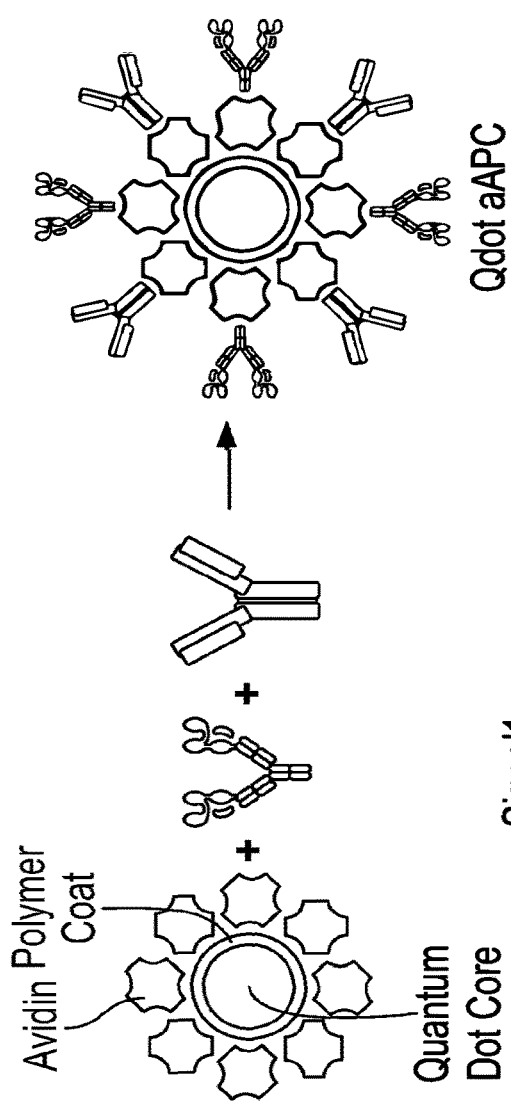
FIG. 5A
FIG. 5B

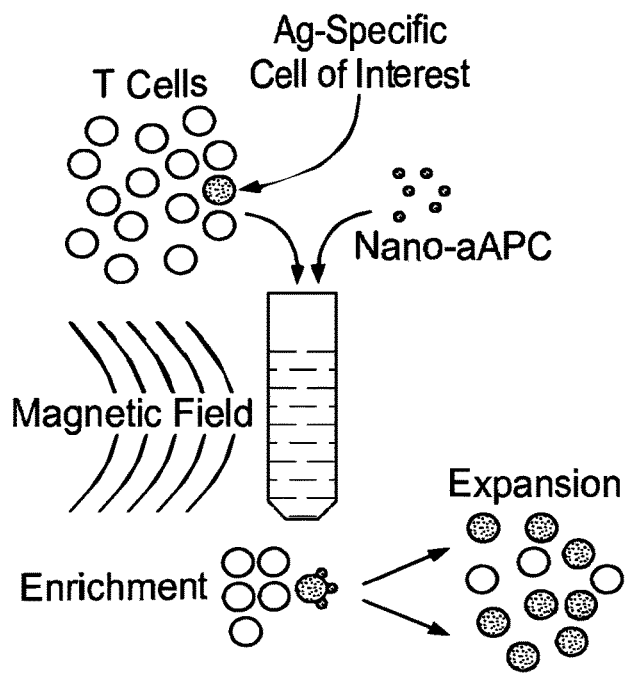
FIG. 8A
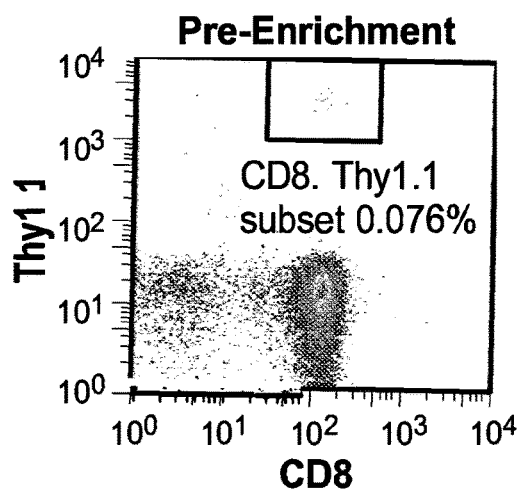 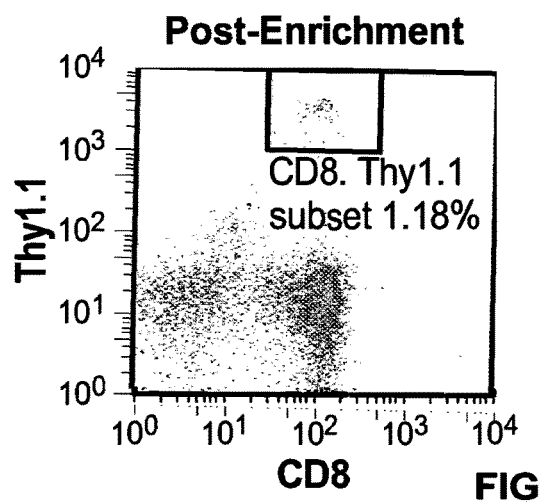
FIG. 8B
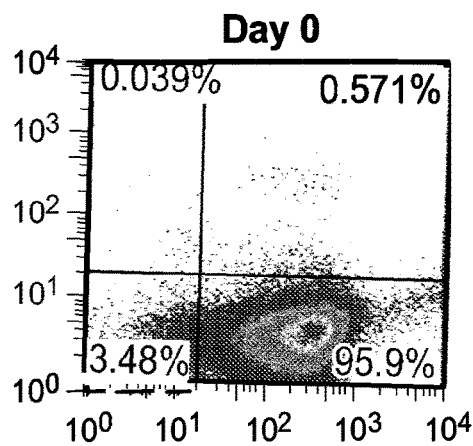 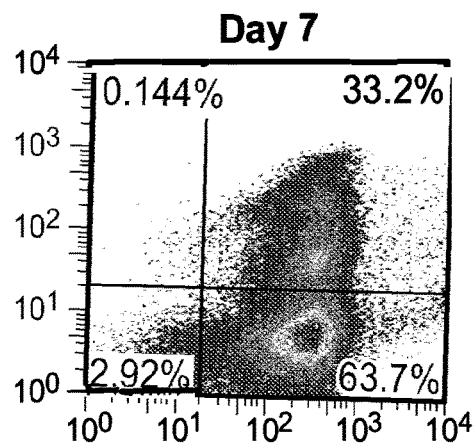
FIG. 8C

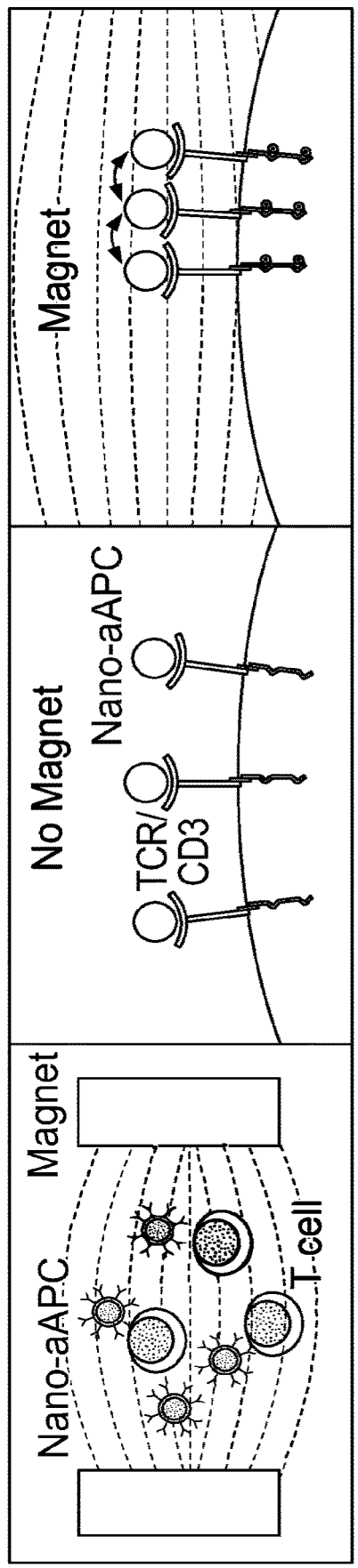

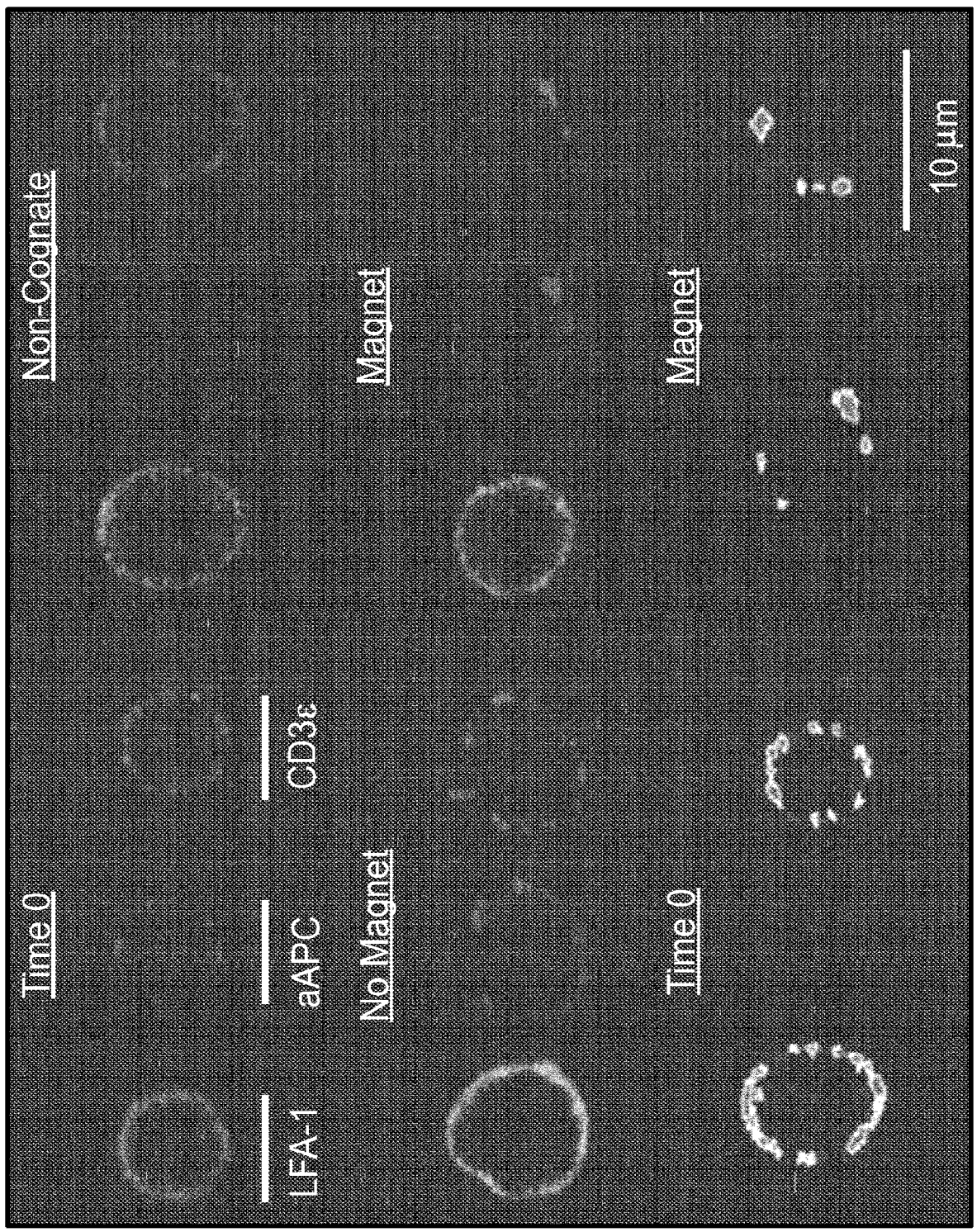

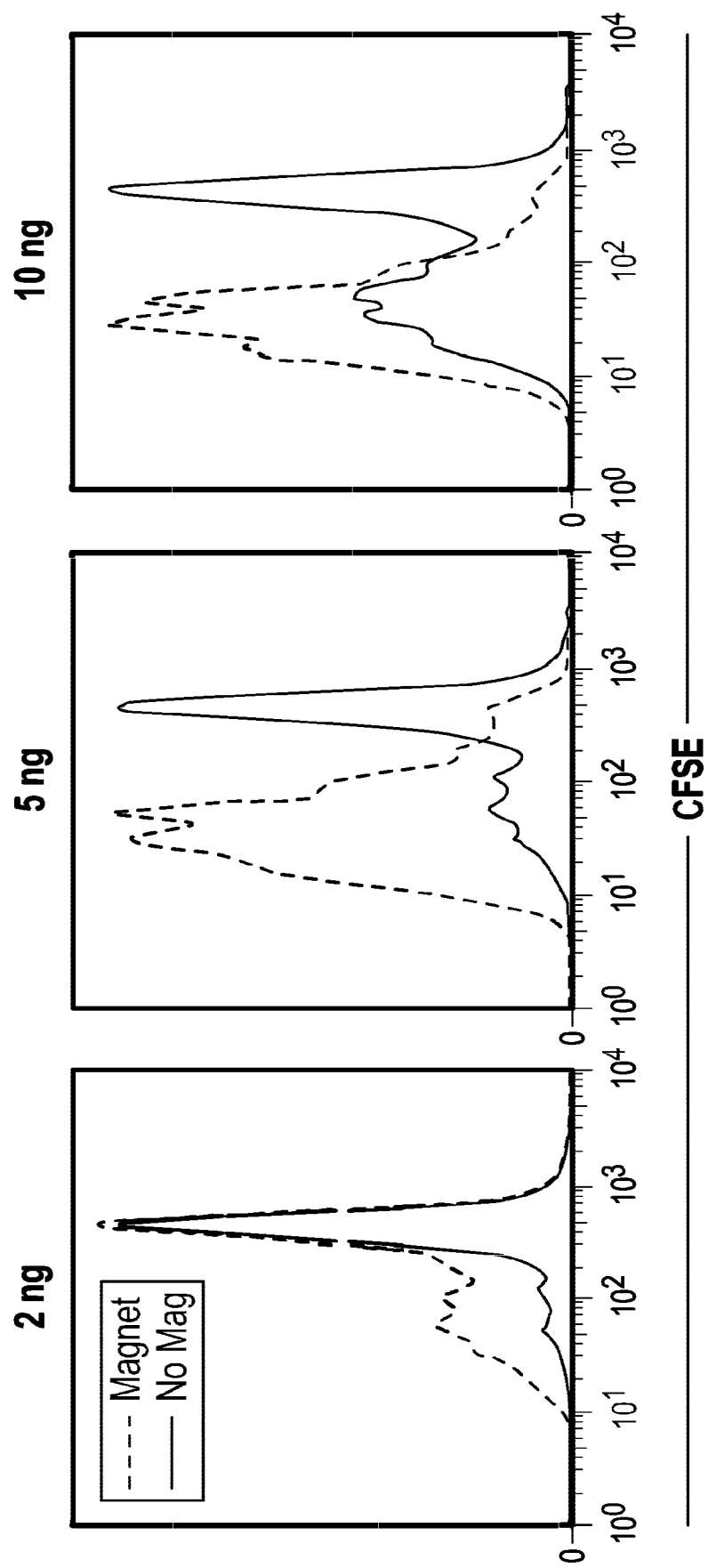

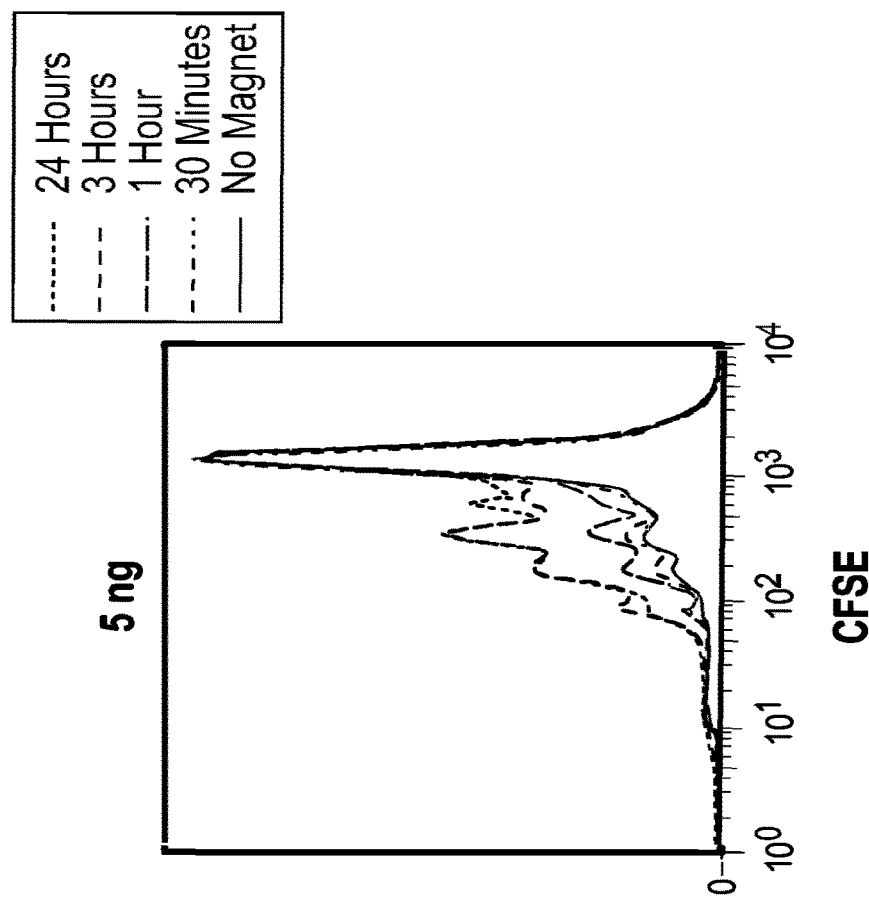
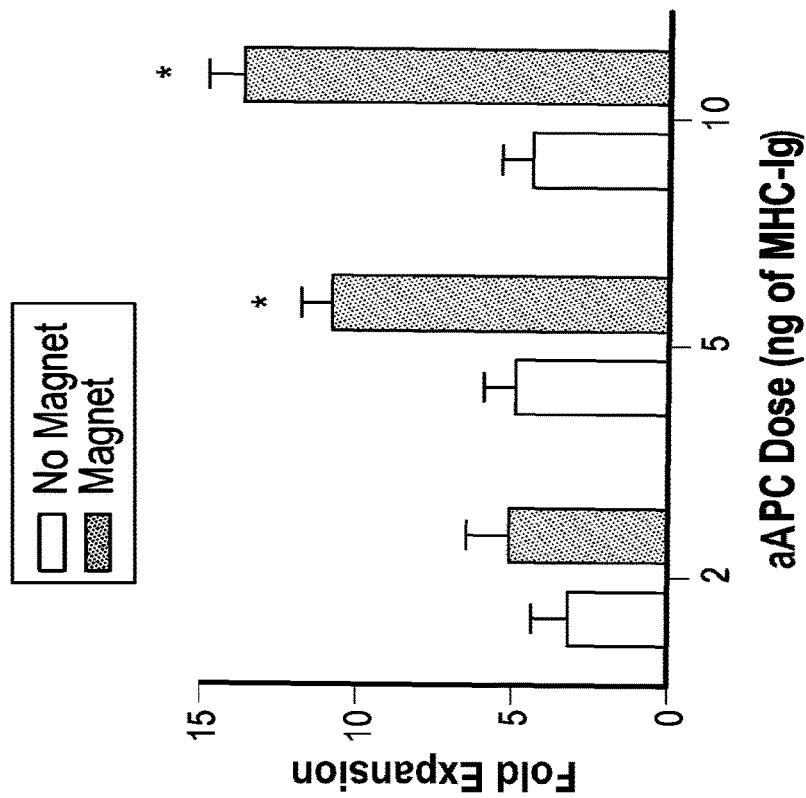
FIG. 11C
FIG. 11B

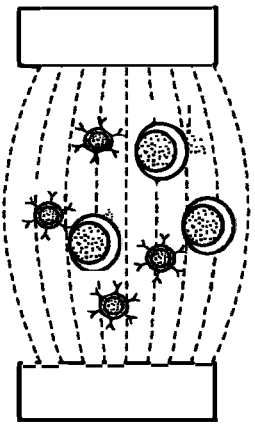
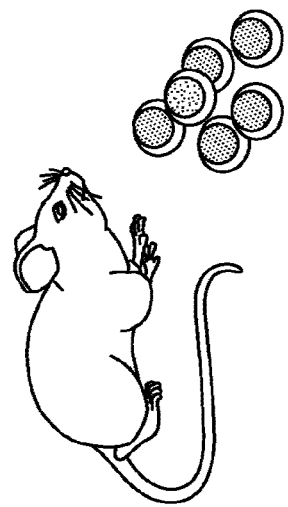
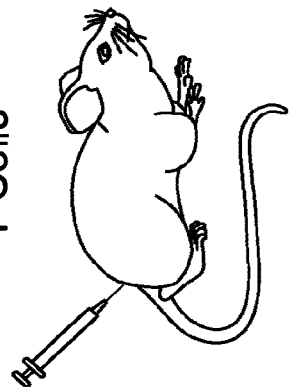
FIG. 12A

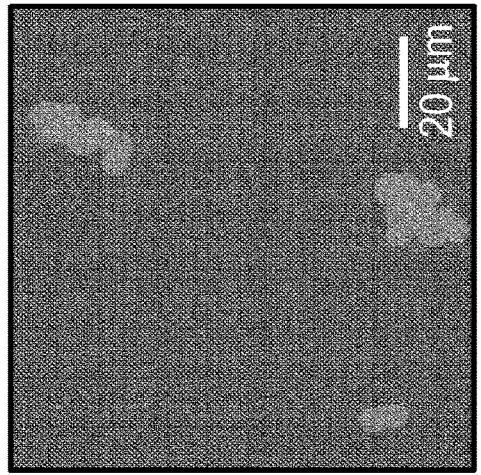
FIG. 16A
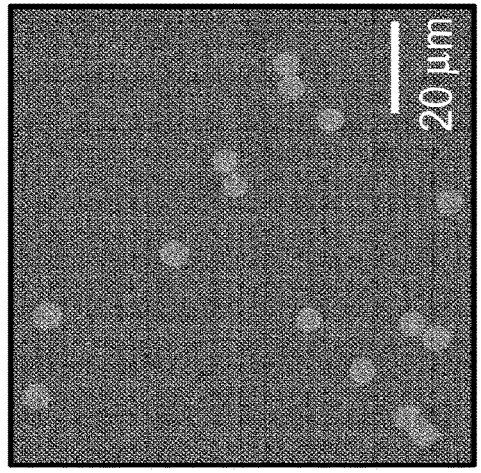
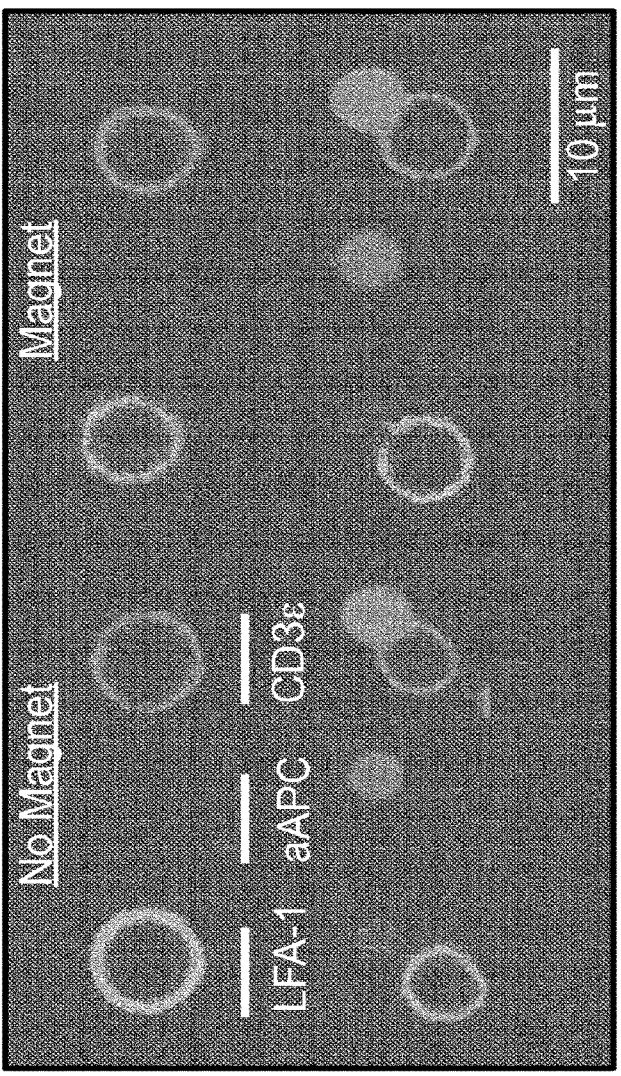
FIG. 16B

NANOSCALE ARTIFICIAL ANTIGEN PRESENTING CELLS

REFERENCE TO PRIORITY APPLICATIONS

This application is a divisional application of U.S. patent application Ser. No. 14/775,855, filed Sep. 14, 2015, which is now U.S. Pat. No. 10,435,668, which is a U.S. national stage application of International Application No. PCT/US2014/025889, filed Mar. 13, 2014, which claims the benefit of, and claims priority to, U.S. Provisional Application No. 61/942,797, filed Feb. 21, 2014, and U.S. Provisional Application No. 61/786,135, filed Mar. 14, 2013, each of which is hereby incorporated by reference in their entireties.

Each reference cited in this disclosure is incorporated herein by reference in its entirety.

TECHNICAL FIELD

This disclosure relates to immunotherapy.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NEX-006DV_Sequence_Listing.txt; date created: Aug. 23, 2019; file size: 1,734 bytes in size).

BRIEF DESCRIPTION OF THE DRAWINGS

FIGS. 1A-C. Synthesis and Characterization of Iron-Dextran Nano-aAPC. Nano-aAPC were synthesized in one of two ways: FIG. 1A, Direct chemical coupling of soluble MHC-Ig Dimer (Signal 1) and B7.1-Ig (Signal 2) in a 1:1 molar ratio to the surface of a paramagnetic iron-oxide, dextran-coated particle. FIG. 1B, Binding of biotinylated MHC-Ig dimer (Signal 1) and biotinylated anti-CD28 (Signal 2) in a 1:1 molar ratio to anti-biotin coated particles. FIG. 1C, Nanoparticle Tracking Analysis confirms that Nano-aAPC are a monodisperse mixture of particles with a mean diameter of 50-100 nm suspended at a concentration of 8.3 nM.

FIG. 2A, Antigen specific nano-aAPC induce proliferation. TCR transgenic 2C (grey) and pMEL (white) T cells proliferated only when incubated with anti-biotin coated particles bearing cognate MHC/peptide, and not in the presence of particles bearing either non-cognate peptide or non-cognate MHC. FIG. 2B, Addition of both Signal 1 and Signal 2 leads to optimal T cell expansion. At a dose of 10 particles per $1*10^6$ T cells, only anti-biotin particles bearing both MHC-Ig and anti-CD28 induced robust T cell proliferation. FIG. 2C, Proliferation of CD8+ CTL induced by LD and HD particles at dose equivalent concentrations by Day 3 CFSE dilution. Decreased fluorescence indicates increased proliferation. Equivalent volumes of HD particles induces greater proliferation than LD particles, with 0.5 uL LD particles inducing almost no expansion. FIG. 2D, Fold expansion on day 7 of samples in (A) shows a similar pattern. Proliferation is dose-dependent and 2-4 fold greater for HD particles compared to an equivalent dose of LD particles. FIG. 2E, Day 3 CFSE dilution of CD8+ CTL induced by LD and HD particles at protein equivalent concentrations. When particle doses are normalized to equivalent protein concentrations, particles induce similar amounts of proliferation. FIG. 2F, Fold expansion on day 7 of samples in (C) demonstrates equivalent expansion for HD and LD particles at an equivalent protein dose. A threshold of about 0.5 uL LD particles or 0.08 uL HD particles is required to induce detectable expansion.

FIGS. 3A-F. T cell Functional Characterization. FIG. 3A, CD8+ T cells were expanded using HD and LD particles. Particle doses were chosen to induce equivalent expansion by HD and LD particles (3.5 uL and 20 uL, respectively) and to induce more robust expansion (HD 20 uL). Samples were re-stimulated on day 7 and assessed for effector function by intracellular cytokine staining assay. 20 uL HD sample (black circles), 3.5 uL HD sample (black filled square), and 20 uL LD samples (unfilled square) all induced robust, equivalent, and dose-dependent (FIG. 3B) degranulation measured by CD107a and (FIG. 3C) IFNγ production. FIG. 3D, Memory effector phenotype measured by staining of surface proteins CD44 and CD62L. T cells can be classified as naive (CD62Lhi, CD44lo), Central Memory (CD62Lhi, CD44hi), or Effector Memory (CD62Llo, CD44hi). E) Representative FACS plot shows three populations seven days after nano-aAPC stimulation. FIG. 3F, T cells were stimulated with 2, 10 and 50 μL of LD or HD iron-oxide nano-aAPC and characterized seven days later. Bar plots show percentage of Naive (unfilled), $T_{cm}$ (grey fill), and $T_{em}$ (black fill) cells generated after stimulation.

FIG. 4A, PBMC were incubated with increasing doses of iron-dextran nano-aAPC bearing A2-M1 MHC-Ig and assessed for antigen-specificity by tetramer staining before stimulation (PBMC, top row) or after one (middle row) or two (bottom row) weeks of stimulation. Numbers in top left represent percentage of CD8+ cells that were tetramer+ (gated). The size of the M1 specific population increases with repeated rounds of stimulation (top to bottom) and increasing dose of nano-aAPC (left to right). Plots are representative of results from three separate experiments, summarized in panel B. FIG. 4B, Percentage of CD8+ PBMC binding M1 tetramer increases with repeated stimulation and increasing dose of nano-aAPC (left panel). The total number of tetramer-positive cells (right panel) similarly increases with rounds of stimulation and particle dose, expanding up to 800-fold of the initial precursor population.

FIGS. 5A-B. Synthesis and Characterization of Quantum Dot Nano-Aapc. FIG. 5A, Quantum Dot (Qdot) Nano-aAPC were constructed by avidin-biotin mediated coupling of soluble MHC-Ig Dimer (Signal 1) and anti-CD28 antibody (Signal 2) in a 1:1 ratio to the surface of a polymer-coated quantum dot particle. FIG. 5B, Qdot Nano-aAPC expansion in whole CD8+ T cells. Fold expansion on Day 7 is dose dependent and antigen-specific. Non cognate particles did not induce any expansion, whereas the highest dose of cognate quantum dot aAPC induced 14.6 fold expansion of CTL.

FIG. 6A, quantum dot aAPC. B16 Tumors were injected subcutaneously on day 0, with injection of naive pMEL T cells on the same day. One day later, quantum dot aAPC were injected intravenously (iv). Tumor size was measured as surface area (mm 2) on indicated days, with Area Under Curve (AUC) shown at right. Mice treated with pMEL T cells and cognate quantum dot aAPC (black bars) had less tumor growth compared to no treatment (white), T cells alone (light grey), and T cells+noncognate quantum dot aAPC (checkered) (4 mice per group). Significance was characterized over entire experiment by AUC (p<0.02) for treatment group compared to non-cognate quantum dot aAPC. FIG. 6B, Iron-Dextran aAPC. Naive pMEL T cells were injected intravenously on day −7. One day later, quantum dot aAPC were injected either iv or subcutaneously (sc) on the right flank. B16 tumors were injected sc on right flank on day 0. Mice in treatment arms were given an additional injection on day 4 post tumor injection either iv or sc, to form four treatment groups: noncognate aAPC iv (day −6) then sc (day 4) (checkered), cognate aAPC iv then iv (light grey), cognate aAPC iv then sc (dark grey), and cognate aAPC sc then sc (black). Mice treated with pMEL T cells and cognate Iron-Dextran aAPC iv/sc or sc/sc (filled squares) had less tumor growth compared to noncognate aAPC (7 mice per group, * p<0.01 for AUC).

FIG. 8A. Schematic of magnetic enrichment strategy for enhanced T cell activation. Low-frequency precursors cells are bound to nano-aAPC carrying specific antigen of interest. Antigen-specific cells are enriched by positive magnetic selection, enhancing subsequent expansion. FIG. 8B. The frequency of antigen specific T cells (y axis) is enhanced by magnetic enrichment using nano-aAPC. FIG. 8C. Increased frequency of antigen specific cells after seven days of nano-aAPC mediated expansion post enrichment.

FIG. 9A, Schematic of nano-aAPC synthesis by coupling MHC-Ig dimers and co-stimulatory anti-CD28 to iron-dextran nanoparticles. FIG. 9B, Proliferation of naive (left) and activated (right) pmel T cells measured by CFSE dilution 3 days after stimulation with nano-aAPC presenting 8 ng of db-GP100. Unstimulated controls in grey. FIG. 9C, Fold expansion of naive (red) and activated (blue) cells seven days after nano-aAPC stimulation. Nano-aAPC presenting 8 ng or less of MHC-Ig induced minimal proliferation in naive cells (*, p<0.01 compared to activated T cells. FIG. 9D, Disassociation of Kb-SIY nanoparticles bound to 2C T cells (half-lives significantly different p<0.02 by paired Student's t-test). See Table 1. FIG. 9E, Mean TCR-MHC contacts made between Kb-Sly dimers (MHC-Ig) and Kb-SIY nanoparticles (Particle) with naive (red) and activated (blue) cells as estimated from disassociation data (p<0.05 by ANOVA with Tukey's post-test, see Table 1). FIG. 9F, Equilibrium binding of increasing doses of nano-aAPC (measured by total MHC-Ig presented) to naive (red) and activated (blue) cells (p<0.0001 by two-way ANOVA). FIG. 9G, A binding model that explains increased equilibrium binding and particle off-rate: naive cells bind more beads with fewer contacts per bead than activated cells.

FIGS. 10A-G. Clustering of aAPC and CD3ε Induced by a Magnetic Field. FIG. 10A-C, Schematic of magnet-induced clustering. FIG. 10D, aAPC and CD3 aggregation immediately after nano-aAPC binding (Time 0) and after incubation in the presence or absence of a magnetic field. Cells were labeled with antibodies against LFA-1 (green), MHC-Ig on nano-aAPC (red), and CD3ε (magenta). Representative images are shown for cells prior to incubation (Time 0, top left), cells incubated with non-cognate particles (Non-Cognate, top right), cells incubated with cognate nano-aAPC (No Magnet, bottom left), and cells incubated with cognate nano-aAPC in a magnetic field (Magnet, bottom right). FIG. 10E, Aggregate detection shown for representative images from Time 0 group (two on left) and Magnet group (two on right). White outlines represent borders of CD3 clusters (magenta) identified by algorithm. FIG. 10F, Average cluster area identified with cluster detection algorithm (15 cells/group). The No Magnet group had significantly larger clusters than Time 0 (*, mean difference 0.22 $\mu m^2$), and the Magnet group had significantly larger clusters than both Time 0 (, mean difference 0.46 $\mu m^2$, p<0.0001 by ANOVA with Tukey post-test) and No Magnet (, mean difference 0.24 $\mu m^2$). FIG. 10G, Cells in No Magnet group had fewer clusters per cell than Time 0 (*, mean difference 5.8 clusters) and Magnet group cells had fewer clusters per cell than No Magnet (**, mean difference 1.9 clusters, p<0.001 by ANOVA with Tukey post-test).

FIGS. 11A-G. Magnet-enhanced Nano-aAPC Stimulation Leads to Robust T cell Proliferation In Vitro. FIG. 11A, Pmel T cell proliferation by CFSE dilution three days after stimulation with nano-aAPC in the presence (red) or absence (black) of a 0.2 T external magnetic field. FIG. 11B, Fold expansion of samples described in A seven days after stimulation. FIG. 11C, Pmel T cells incubated with 5 ng MHC-Ig dose of nano-aAPC and 0.2 T magnetic field for 0-24 hours. Proliferation assessed by CFSE dilution at day 3. FIG. 11D, Fold expansion of samples from C seven days after stimulation. (*, p<0.001 by ANOVA with Tukey post-test) FIG. 11E, Pmel T cells incubated with 5 ng MHC-Ig dose of nano-aAPC and magnetic fields of increasing maximal strength (0.15-0.225 T) generated by neodymium magnets of increasing thickness for twenty-four hours. FIG. 11F, Proliferation of samples from E seven days after stimulation (* greater than no magnet, ** greater than 0.15 T magnet, p<0.001 by ANOVA with Tukey post-test). FIG. 11G, Antigen-specific expansion of endogenous CD8+ lymphocytes from wild type mice after stimulation with Kb-Trp2 nano-aAPC in the presence or absence of a 0.2 T magnetic field for twenty-four hours. After seven days, populations were stained with cognate Kb-Trp2 (top row) or non-cognate Kb-SIINF (bottom row) MHC-Ig dimer.

FIGS. 12A-F. Magnet-Enhanced T Cell Expansion In Vivo and Increased Efficacy of Adoptive Immunotherapy. FIG. 12A, Schematic of adoptive immunotherapy model. CD44lo, CD8+ T cells from Thy1.1+ pmel TCR transgenic mice were stimulated in vitro for 24 hours in the presence or absence of nano-aAPC (5 ng total MHC-Ig) and magnetic field prior to being adoptively transferred into wild type, Thy1.2+ B6 recipient mice (6 mice per group). FIG. 12B, Representative frequencies of Thy1.1 cells from spleens 7 days after transfer and day lymph nodes 21 days after transfer. FIG. 12C, Frequencies of Thy1.1+ cells were significantly higher in mice given T cells stimulated with nano-aAPC in a magnetic field (red) compared to nano-aAPC with no magnet (grey) and no stimulation (white) (p<0.001 for treatment effect by two-way ANOVA for day 7 and 21). FIG. 12D, Total Thy1.1+ cells in all organs combined on Day 7 and Day 21. Five-fold more cells were observed in the nano-aAPC+Magnet group than nano-aAPC alone group on day 7 (p <0.05 by student's t-test), but did not reach significance on Day 21 (p=0.15). FIG. 12E, Schematic of treatment of established tumors with magnetic field enhanced adoptive immunotherapy. SC tumors were administered on Day 0, partial myeloablation on Day 9, and CD44lo, CD8+ pmel T cells stimulated for 24 hours with either nano-aAPC (5 ng total MHC-Ig) in a magnetic field (red) or nano-aAPC with no magnet (black) were transferred on Day 10. T cell alone (grey) and untreated (unfilled) groups were used as control (8 mice per group). FIG. 12F, Treatment with magnet-enhanced nano-aAPC activated T cells attenuated tumor growth compared to no magnet and control groups ($p<0.0001$ for treatment effect by two-way ANOVA). Arrow indicates timepoint of adoptive transfer (day 10). Mice were censored if dead or tumors were greater than 150 mm$^2$. Treatment led to increased survival in T cells+nano-aAPC+Magnet group ($p<0.001$ by Mantel-Cox log-rank test).

FIG. 13A, Mean fluorescence intensity (MFI) of antibody bound to nanoparticles and controls. Nano-aAPC and Micro-aAPC (cell-sized) particles were incubated with excess of monoclonal anti-mouse IgG1 (for MHC-Ig) and anti-antibody conjugated with PE for 30 minutes, and washed on a magnetic column. Fluorescent antibody bound to particles was detectable above background samples, including micro- and nano-particles not stained with anti-IgG1 (No Ab) and particles which were not coupled to protein and stained with anti-IgG1 (Blank). Protein concentration in solution was determined by comparison to an IgG1-PE standard curve. Fluorescence is shown for anti-IgG1 and is representative of three experiments. HD—High Density. LD—Low Density. FIG. 13B, Particles in solution do not interfere with antibody fluorescence. Soluble anti-IgG1 PE antibody was titrated and measured for fluorescence. Similar fluorescence emission was observed when soluble antibody was measured in the presence of blank micro- and nano-particles. FIG. 13C, Washing in magnetic column was sufficient to remove free antibody. After three washes (Fraction 3), fluorescence is not detectable above background. Fluorescence of 0.63 ug/ml free antibody is provided for comparison. FIG. 13D, Nanoparticle concentration was characterized by iron absorbance at 405 nm. Particle concentrations were determined by Nanoparticle Tracking Analysis. Titrations of nanoparticles were measured for absorbance and a standard curve was calculated to determine particle concentration.

FIG. 14A, CD8+ pMEL splenocytes include a population of memory-phenotype, CD44 positive cells (representative percentage shown as percentage of CD8, left). CD44lo naive cells were isolated by a no-touch negative selection enrichment with anti-CD44 antibody in a magnetic enrichment column. FIG. 14B, Proliferation of Naive CD44lo (left) and activated (right) cells by CFSE dilution stimulated three days with micro-aAPC (dark red and blue lines) and nano-aAPC (light red and blue lines) or unstimulated (grey lines). Micro- and nano-aAPC were used at doses presenting equivalent total amount of MHC-Ig (8 ng). Nano-aAPC data are re-produced from FIG. 1. FIG. 14C, Proliferation of naive (red) and active (blue) cells seven days after stimulation with indicated doses of micro-aAPC. FIG. 14D, Effect of MHC-Ig density on micro-aAPC induced stimulation. High density (HD, blue) and low density (LD, red) micro-aAPC were nonnalized for total MHC-Ig (4-16 ng). See Table 1 for density. Proliferation assessed by CFSE dilution three days after activation. FIG. 14E, Fold expansion of samples shown in FIG. 14D seven days after activation, representative of three experiments.

FIG. 15A, Kb-SIY nanoparticle binding to cognate 2C T cells. Binding to activated cells, seven days after peptide activation (activated, blue, MFI 89) as compared to naive, CD44lo isolated 2C T cells (naive, red, MFI 179) and control non-cognate CD44lo pmel T cells (non-specific binding, grey, MFI 21). Binding is characterized as mean fluorescence intensity of Alexa 647 labeled particles bound to cells. FIG. 15B, Surface TCR expression of naive (MFI 137) and activated (MFI 128) cells measured with fluorescent anti-TCRβ. FIG. 15C, Disassociation of Kb-SIY MHC-Ig dimers from activated (dark blue) and naive (dark red) cells. Disassociation of nano-aAPC from activated (light blue) and naive (light red) cells are reproduced from FIG. 1 for comparison. FIG. 15D, Disassociation curves of nano-aAPC bound to naive CD44low cells before (red) and after (black) one hour of incubation in a magnetic field. FIG. is representative of 2 experiments.

FIGS. 16A-E. TCR Clustering and Expansion by Micro-aAPC in a Magnetic Field FIG. 16A, Micro-aAPC aggregation in a magnetic field. Representative confocal images of micro-aAPC (red) shown before (left) and after (right) application of a magnetic field. FIG. 16B, Micro-aAPC magnetic aggregation does not induce CD3 aggregation. Cells were labeled with antibodies against LFA-1 (green), MHC-Ig on micro-aAPC (red), and CDR (magenta). Micro-aAPC displayed auto-fluorescence in all three channels, particularly in the red and magenta channels. Representative images are shown for cells incubated with cognate micro-aAPC (No Magnet), both not in contact (top) and in contact (bottom) with micro-aAPC, and cells incubated with cognate nano-aAPC in a magnetic field (Magnet). FIG. 16C, Average cluster area and clusters per cell identified with cluster detection algorithm (20 cells/group, divided evenly between cells in contact and not in contact with particles). Control samples include cells prior to incubation (Time 0) and cells incubated with non-cognate microparticles (Non-Cognate) ($p>0.05$ by ANOVA). FIG. 16D, Pmel T cells incubated with 5 ng (left) and 10 ng (right) MHC-Ig dose of micro-aAPC with (red) and without (black) a 0.2 T magnetic field for 3 days. Proliferation assessed by CFSE dilution at day 4. FIG. 16E, Fold expansion of pmel T cells incubated with increasing doses of micro-aAPC with and without a 0.2 T magnetic field seven days after stimulation ($p>0.05$ by two-way ANOVA).

SUMMARY

Figure 2A:
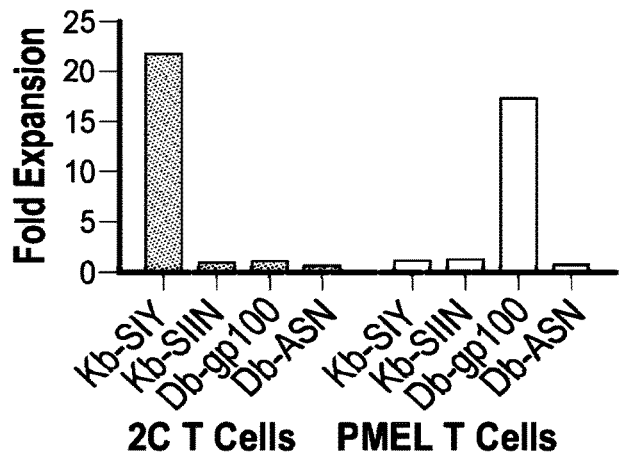
FIGS. 2A-F. Nano aAPC Induced Proliferation is Antigen-Specific and Dose-Dependent.

This disclosure provides a nano-scale artificial antigen presenting cell (nano-aAPC) comprising a nanoparticle; at least one lymphocyte affecting molecule on the surface of the nanoparticle; and at least one molecular complex on the surface of the nanoparticle that, when bound to an antigen, engages a unique clonotypic lymphocyte receptor, i.e., an antigen-specific lymphocyte receptor.

This disclosure provides a nano-aAPC comprising a nanoparticle; at least one B cell affecting molecule on the surface of the nanoparticle; and at least one molecular complex on the surface of the nanoparticle that engages B cell surface immunoglobulins or MHC-antigen complexes on a B cell surface.

This disclosure provides a nano-aAPC comprising a nanoparticle; at least one T cell costimulatory molecule on the surface of the nanoparticle; and at least one MHC class I molecular complex on the surface of the nanoparticle. The at least one MHC class I molecular complex comprises at least two fusion proteins. A first fusion protein comprises a first MHC class I α chain and a first immunoglobulin heavy chain and wherein a second fusion protein comprises a second MHC class I α chain and a second immunoglobulin heavy chain. The first and second immunoglobulin heavy chains associate to form the MHC class I molecular complex. The MHC class I molecular complex comprises a first MHC class I peptide binding cleft and a second MHC class I peptide binding cleft.

This disclosure provides a preparation comprising a plurality of nano-aAPCs described above.

This disclosure provides a method of inducing the formation of antigen-specific T cells. The method comprises contacting an isolated preparation comprising a plurality of precursor T cells with at least one first nano-aAPC which comprises a T cell affecting molecule and an antigen presenting complex that comprises at least one antigen binding cleft. An antigen is bound to the antigenic binding cleft. Members of the plurality of precursor T cells are thereby induced to form a first cell population comprising antigen-specific T cells that recognize the antigen. The number or percentage of antigen-specific T cells in the first cell population is greater than the number or percentage of antigen-specific T cells that are formed if precursor T cells are incubated with a nano-aAPC that comprises an antibody that specifically binds to CD3 but does not comprise an antigen presenting complex.

This disclosure provides a method of increasing the number or percentage of antigen-specific T cells in a population of cells. The method comprises incubating a first cell population comprising antigen-specific T cells with at least one first nano-aAPC which comprises a T cell affecting molecule and an antigen presenting complex that comprises at least one antigen binding cleft. An antigen is bound to the antigen binding cleft. The incubation is carried out for a period of time sufficient to form a second cell population comprising an increased number or percentage of antigen-specific T cells relative to the number or percentage of antigen-specific T cells in the first cell population.

This disclosure provides a method of regulating an immune response in a patient. The method comprises administering to a patient a preparation comprising (A) a plurality of particles and (B) a pharmaceutically acceptable carrier. Members of the plurality of particles comprise (1) at least one T cell affecting molecule; and (2) at least one antigen presenting complex. The at least one antigen presenting complex comprises at least one antigen binding cleft. An antigen is bound to the at least one antigen binding cleft.

This disclosure provides a method of suppressing an immune response in a patient. The method comprises administering to a patient a preparation comprising (A) a plurality of particles and (B) a pharmaceutically acceptable carrier. Members of the plurality of particles comprise (1) at least one apoptosis-inducing molecule; and (2) at least one antigen presenting complex. The at least one antigen presenting complex comprises at least one antigen binding cleft. An antigen is bound to the at least one antigen binding cleft.

This disclosure provides a method of increasing the number or percentage of antibody-producing B cells in a population. The method comprises contacting an isolated preparation comprising a plurality of precursor B cells with at least one first nano-aAPC which comprises a nanoparticle; at least one B cell affecting molecule on the surface of the nanoparticle; and at least one molecular complex on the surface of the nanoparticle that engages B cell surface immunoglobulins or MHC-antigen complexes on a B cell surface. Members of the plurality of precursor B cells are thereby induced to form a first cell population comprising antibody-producing B cells that produce antibodies that specifically bind to the antigenic peptide.

This disclosure provides a method of increasing the number or percentage of antibody-producing B cells in a population. The method comprises incubating a first cell population comprising antibody-producing B cells with at least one first nano-aAPC which comprises a nanoparticle; at least one B cell affecting molecule on the surface of the nanoparticle; and at least one molecular complex on the surface of the nanoparticle that engages B cell surface immunoglobulins or MHC-antigen complexes on a B cell surface. The incubating is carried out for a period of time sufficient to form a second cell population comprising an increased number or percentage of antibody-producing B cells relative to the number or percentage of antibody-producing B cells in the first cell population.

This disclosure provides a method of increasing the number or percentage of antibody-producing B cells in a population. The method comprises contacting an isolated preparation comprising a plurality of precursor B cells with a preparation of nano-aAPCs. The nano-aAPCs comprise a nanoparticle, at least one B cell affecting molecule on the surface of the nanoparticle; and at least one molecular complex on the surface of the nanoparticle that engages B cell surface immunoglobulins or MHC-antigen complexes on a B cell surface. Members of the plurality of precursor B cells are thereby induced to form a first cell population comprising antibody-producing B cells that produce antibodies that specifically bind to the antigenic peptide.

This disclosure provides a method of regulating an immune response in a patient. The method comprises administering to a patient a preparation comprising (A) a plurality of particles and (B) a pharmaceutically acceptable carrier. Members of the plurality of particles comprise (1) at least one B cell affecting molecule; and (2) at least one molecular complex that engages B cell surface immunoglobulins or MHC-antigen complexes on a B cell surface.

This disclosure provides a method of enriching antigen-specific T cells in a polyclonal T cell population. The method comprises incubating the polyclonal T cell population with a nano-aAPC comprising a nanoparticle; at least one lymphocyte affecting molecule on the surface of the nanoparticle; and at least one molecular complex on the surface of the nanoparticle that, when bound to an antigen, engages antigen-specific lymphocyte receptors. The nano-aAPC further comprises a cross-linking antibody or an oligomerizing molecule.

This disclosure provides a method of activating T cells. The method comprises incubating in the presence of a magnetic field a population of T cells with a nano-aAPC which comprises a T cell affecting molecule and an antigen presenting complex that comprises at least one antigen binding cleft. The nano-aAPC is paramagnetic.

This disclosure provides a method of providing a population of antigen-specific T cells to a patient in need thereof, comprising:

(1) contacting an isolated population of T cells with a plurality of nano-scale artificial antigen presenting cells (nano-aAPCs) in the presence of a magnetic field of sufficient strength to generate antigen-specific T cells, wherein nano-aAPCs of the plurality are paramagnetic nanoparticles which comprise on their surface (i) at least one T cell affecting molecule and (ii) at least one antigen presenting complex, wherein the antigen presenting complex comprises at least one antigen binding cleft and wherein the antigen binding cleft comprises an antigen;

(2) isolating complexes of antigen-specific T cells bound to nano-aAPC from the isolated population of T cells; and (3) administering the complexes to the patient.

In some variations of this method, the isolated population of T cells comprises naïve T cells. In some variations of these methods, complexes are isolated using a magnetic enrichment column, flow cytometry, or differential centrifugation. In some variations of this method, the complexes are administered by a route of administration selected from the group consisting of intravenous administration, intra-arterial administration, subcutaneous administration, intradermal administration, intralymphatic administration, and intra-tumoral administration.

This disclosure provides a method of providing a population of antigen-specific T cells to a target area in a patient in need thereof, comprising:

(1) administering to the patient a plurality of nano-scale artificial antigen presenting cells (nano-aAPCs) in the presence of a magnetic field of sufficient strength to stimulate antigen-specific T cells, wherein nano-aAPCs of the plurality are paramagnetic and comprise on their surface (i) a T cell affecting molecule and (ii) an antigen presenting complex, wherein the antigen presenting complex comprises an antigen binding cleft, wherein binding of an antigen to the antigen binding cleft engages a unique antigen-specific lymphocyte receptors; and (2) applying to the target area a magnetic field, wherein the target area comprises the antigen which engages unique antigen-specific lymphocyte receptors., thereby directing the nano-aAPCs to the target area.

In some variations of the method described above, nano-aAPC are administered by a route of administration selected from the group consisting of intravenous administration, intra-arterial administration, subcutaneous administration, intradermal administration, intralymphatic administration, and intra-tumoral administration.

In some variations of the methods described above, the at least one antigen presenting complex comprises an MHC class I peptide binding cleft.

In some variations of the methods described above, the at least one antigen presenting complex is an MHC class I molecule. In some of these variations, the at least one antigen presenting complex is an MHC class I molecular complex comprising at least two fusion proteins, wherein a first fusion protein comprises a first MHC class I α chain and a first immunoglobulin heavy chain and wherein a second fusion protein comprises a second MHC class I α chain and a second immunoglobulin heavy chain, wherein the first and second immunoglobulin heavy chains associate to form the MHC class I molecular complex, wherein the MHC class I molecular complex comprises a first MHC class I peptide binding cleft and a second MHC class I peptide binding cleft.

In some variations of the methods described above, the at least one antigen presenting complex comprises an MHC class II peptide binding cleft. In some of these variations, the antigen presenting complex is an MHC class II molecule. In some of these variations, the antigen presenting complex is an MHC class II molecular complex comprising at least four fusion proteins, wherein (a) two first fusion proteins comprise (i) an immunoglobulin heavy chain and (ii) an extracellular domain of an MHC class IIβ chain; and (b) two second fusion proteins comprise (i) an immunoglobulin light chain and (ii) an extracellular domain of an MHC class IIα chain, wherein the two first and the two second fusion proteins associate to form the MHC class II molecular complex, wherein the extracellular domain of the MHC class IIα chain of each first fusion protein and the extracellular domain of the MHC class IIα chain of each second fusion protein form an MHC class II peptide binding cleft. In some of these variations, the immunoglobulin heavy chain comprises a variable region.

In some variations of the methods described above, an antigenic peptide is bound to the at least one antigen binding cleft. In some of these variations, the antigenic peptide is selected from the group consisting of a peptide of a tumor-associated antigen, a peptide of an autoantigen, a peptide of an alloantigen, and a peptide of an infectious agent antigen.

In some variations of the methods described above, nano-APCs comprise at least two antigen presenting complexes. In some of these variations, an identical antigen is bound to each antigen binding cleft of the at least two antigen presenting complexes. In other of these variations, different antigens are bound to each antigen binding cleft of the at least two antigen presenting complexes. In some variations, a first antigen presenting complex comprises at least one MHC class I peptide binding cleft and wherein a second antigen presenting complex comprises at least one MHC class II peptide binding cleft.

In some variations of the methods described above, the at least one antigen presenting complex is a non-classical MHC-like molecule. In some of these variations, the non-classical MHC-like molecule is a CD1 family member. The non-classical MHC-like molecule can be selected from the group consisting of CD1a, CD 1b, CD1c, CD1d, and CD1e.

In some variations of the methods described above, the at least one T cell affecting molecule is a T cell costimulatory molecule. The T cell costimulatory molecule can be selected from the group consisting of CD80 (B7-1), CD86 (B7-2), B7-H3, 4-1BBL, CD27, CD30, CD134 (OX-40L), B7h (B7RP-1), CD40, LIGHT, an antibody that specifically binds to CD28, an antibody that specifically binds to HVEM, an antibody that specifically binds to CD40L, an antibody that specifically binds to OX40, and an antibody that specifically binds to 4-1BB.

In some variations of the methods described above, the at least one T cell affecting molecule is an adhesion molecule.

In some variations of the methods described above, the adhesion molecule is selected from the group consisting of ICAM-1 and LFA-3.

In some variations of the methods described above, the at least one T cell affecting molecule is a T cell growth factor. The T cell growth factor can be selected from the group consisting of a cytokine and a superantigen. The cytokine can be selected from the group consisting of IL-2, IL-4, IL-7, IL-10, IL-12, IL-15, and gamma interferon. The T cell growth factor can be selected from the group consisting of (A) a first molecular complex comprising at least two fusion proteins, wherein a first fusion protein comprises a first cytokine and an immunoglobulin heavy chain and wherein a second fusion protein comprises a second cytokine and a second immunoglobulin heavy chain, wherein the first and second immunoglobulin heavy chains associate to form the first molecular complex; and (B) a second molecular complex comprising at least four fusion proteins, wherein, (a) two first fusion proteins comprise (i) an immunoglobulin heavy chain and (ii) a first cytokine; and (b) two second fusion proteins comprise (i) an immunoglobulin light chain and (ii) a second cytokine, wherein the two first and the two second fusion proteins associate to form the second molecular complex.

In some of the variations described above, the T cell growth factor is the first molecular complex. In some of these variations, the first and second cytokines are identical. In other of these variations, the first and second cytokines are different.

In some of the variations described above, the T cell growth factor is the second molecular complex. In some of these variations, the first and second cytokines are identical. In other of these variations, the first and second cytokines are different.

In some variations of the methods described above, the at least one T cell affecting molecule is a regulatory T cell inducer molecule. The T cell inducer molecule can be selected from the group consisting of TGFβ, IL-10, interferon-α, and IL-15.

In some variations of the methods described above, the at least one T cell affecting molecule is an apoptosis-inducing molecule. The apoptosis-inducing molecule can be selected from the group consisting of a toxin, TNFα, and Fas ligand.

In some variations of the methods described above, nano-aAPCs comprise at least two different T cell affecting molecules.

In some variations of the methods described above, the incubation is carried out at 37° C. for 10 minutes to 3 days.

In some variations of the methods described above, the antigen-specific T cells are cytotoxic T cells.

In some variations of the methods described above, the antigen-specific T cells are helper T cells.

In some variations of the methods described above, the antigen-specific T cells are regulatory T cells.

In some variations of the methods described above, the patient has cancer, an autoimmune disease, an infectious disease, or is immunosuppressed.

In some variations of the methods described above, the precursor T cells are obtained from the patient.

In some variations of the methods described above, the precursor T cells are obtained from a donor who is not the patient.

In some variations of the methods described above, the antigen-specific T cells are administered by a route of administration selected from the group consisting of intravenous administration, intra-arterial administration, subcutaneous administration, intradermal administration, intralymphatic administration, and intra-tumoral administration.

Figure 9A:
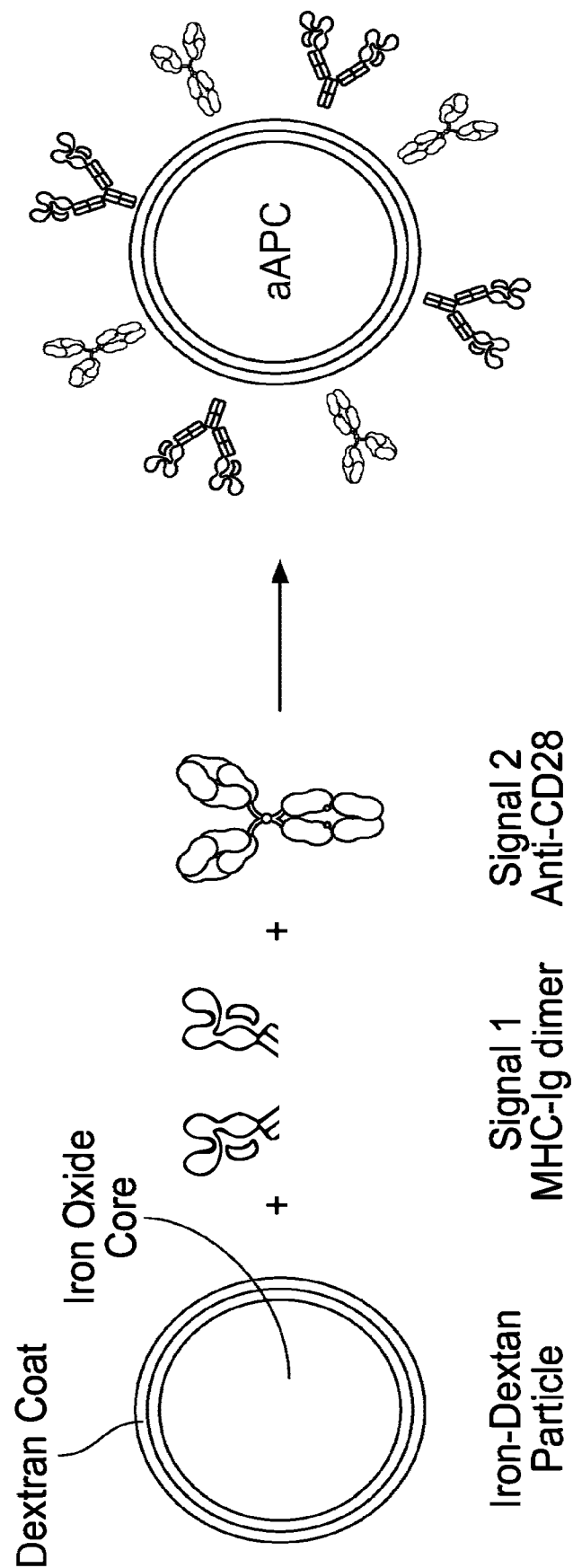
FIGS. 9A-G. Nano-aAPC Bind to Naive and Activated Cells.
Figure 9B:
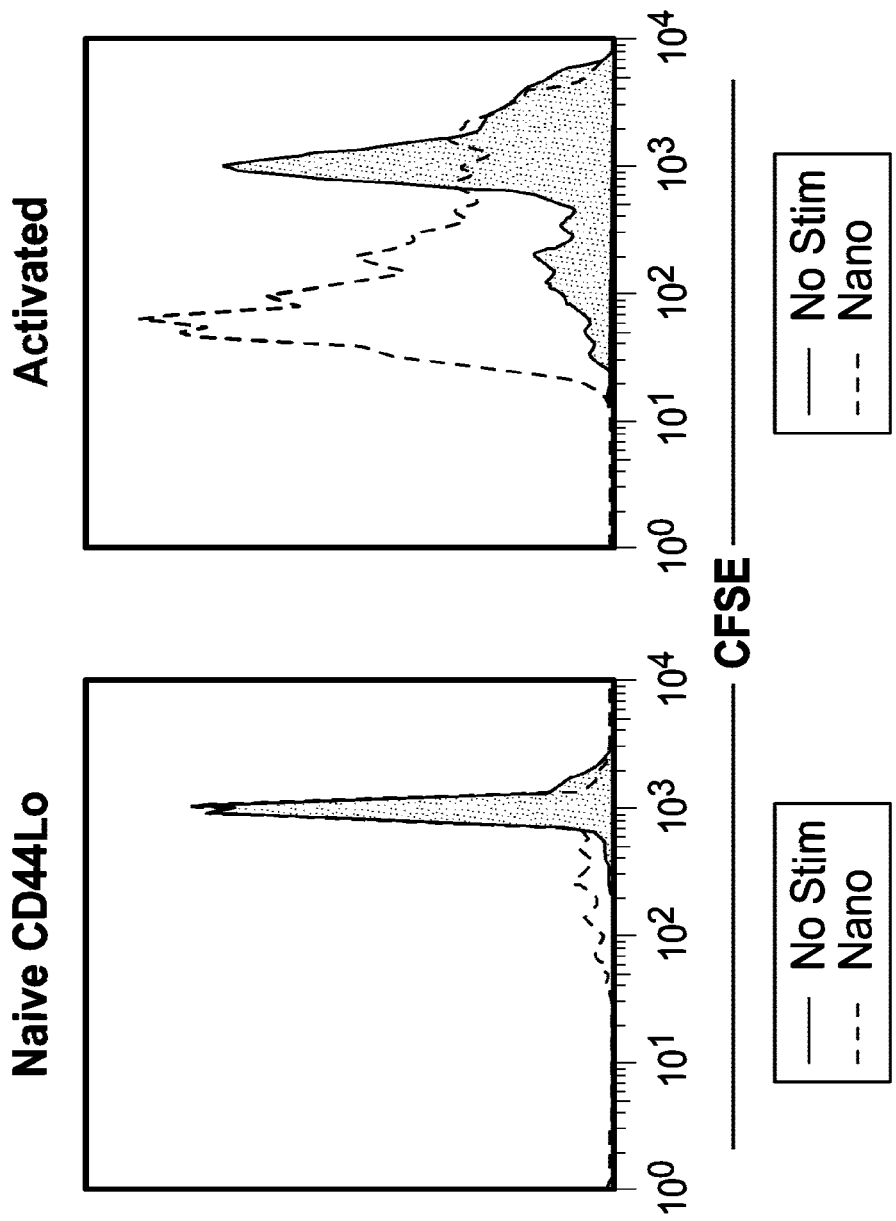
Figure 9C:
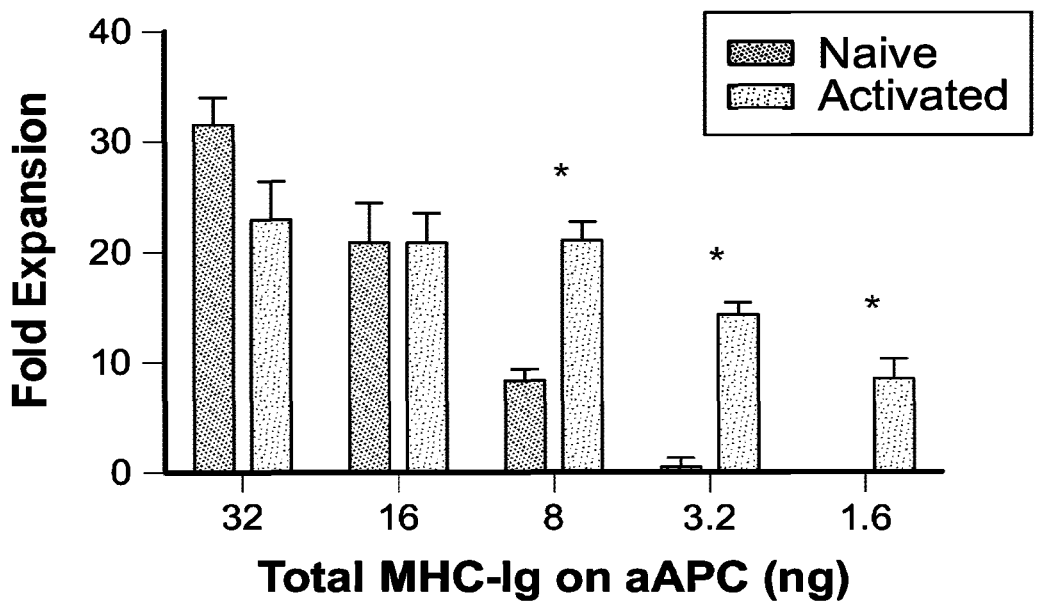

This disclosure provides methods of using nanoparticles, e.g., magnetic nanoparticles, to target cells in different physiological states (e.g., naive vs previously activated T cells) and stimulate the target cell population. For example, as shown in FIG. 9C and discussed in more detail in the specific examples below, nano-aAPCs providing a dose of 32 ng of MHC stimulates both naïve and previously activated T cells between 20- and 30-fold in a week's time. However, at 8 ng or 3.2 ng of MHC, only the activated T cells were stimulated. Thus, a dose of nano-aAPC comprising, e.g., 3.2-8 ng of MHC can be used to stimulate previously activated T cells in a T cell population without affecting naïve T cells in the population.

This disclosure provides methods of differentially stimulating previously activated T cells vs naive T cells. In some variations, nano-aAPC comprising 3.2-8 ng MHC vs 32 ng MHC can be used to separate nano-aAPC binding and isolation of T cells from the activation of the T cells. In some variations, a population of T cells is substantially depleted of previously active T cells using, e.g., an antibody to CD44, leaving a population enriched for naive T cells. Naïve T cells bound to the nano-aAPCs would permit their purification. The naïve T cells comprising the bound nano-aAPCs can then be activated by exposing the T cell-nano-aAPC complexes to a magnetic field.

This disclosure provides methods of separating, characterizing, and using as a therapeutic for other cells including, e.g., B cells and stem cells. The optimum ligand density on the surface of a nanoparticle (or, alternatively, the dose of nanoparticles comprising such ligands) which will differentially activate cells of a population in different physiological states is determined using methods such as those described below in Example 9. Depending on the cell population, the ligand can comprise, e.g., an antibody or a portion of an antibody, a peptide, a nucleotide, a carbohydrate, a lipid, all or portion of the natural ligand for a given receptor (e.g., EGF, PDGF), a chemical (e.g., a chromium salt or a monovalent synthetic ligand that binds immunophilin molecule receptors such as FKBP binding domain), single anti-integrin Fab fragments, RGD peptides, and the like.

DETAILED DESCRIPTION

Immunotherapy includes the activation and expansion of immune cells to treat disease. Induction of cytotoxic (CD8+) lymphocyte (CTL) responses is attractive for therapy because CTL are specific for a given tumor antigen or pathogen, expand several logs to produce robust responses, and generate long-term memory that can prevent recurrence of disease(1). CTL can be directly activated in vivo or can be expanded in vitro and adoptively transferred into a patient (3, 4).

Artificial Antigen Presenting Cells (aAPC), which deliver stimulatory signals to cytotoxic lymphocytes, are a powerful tool for in vitro and in vivo immunotherapy. Thus far, particle-based aAPC have been synthesized by coupling a T cell activating protein to a rigid support several microns in diameter. For example, we previously developed a cell-sized, 4.5 μm diameter ("microscale") bead-based T cell expansion platform by coupling proteins that deliver two necessary and sufficient T cell activation signals (5, 6). Signals present on APC that are required for T cell activation include Signal 1, cognate antigenic peptide presented in the context of Major Histocompatibility Complex (MHC) that bind the TCR (7); and Signal 2, a group of co-stimulatory receptors that modulate T cell response. In some embodiments of this system, Signal 1 is conferred by a chimeric MHC-immunoglobulin dimer loaded with specific peptide (MHC-Ig), and Signal 2 is either B7.1 (the natural ligand for the T cell receptor CD28) or an activating antibody against CD28. Both proteins are directly chemically coupled to the surface of a microscale (4.5 μm) bead to create an artificial Antigen Presenting Cell (aAPC).

However, there are several drawbacks to microscale aAPC. Large beads can lodge in capillary beds and induce tissue damage when injected intravenously. When injected subcutaneously, micron-sized beads are not easily carried to lymph nodes where most T cells reside (8, 9). Furthermore, micron-sized beads are known to be preferentially cleared by phagocytic cells of the reticulo-endothelial system (10, 11).

The present disclosure overcomes these limitations by providing various nanoscale aAPC (nano-aAPC). To our knowledge, this is the first description of nanoscale bead-based aAPC that induces T cell proliferation. Nanoparticles have been evaluated for antigen or drug uptake; however, aAPC platforms require specific cell surface receptor-ligand interactions to occur at the nanoparticle-cell interface. Studies have suggested that only beads larger than 2 microns in diameter are able to induce T cell proliferation (16, 17); and work with smaller size particles, such as quantum dot nanocrystals, has focused on the use of those reagents to study biophysical aspects of TCR-MHC interaction (15). When directly tested, recent work demonstrated that nanoparticles were much less efficient than microbeads in inducing short-term functional responses, with no reported proliferation (18).

It was therefore unexpected that nano-aAPC as described herein induce antigen-specific T cell proliferation, both from TCR transgenic mouse splenocytes and from human polyclonal peripheral blood T cells. Stimulated T cells had a robust effector phenotype, degranulating and producing IFNγ after re-challenge. Nanoscale aAPCs described herein also mediate tumor rejection in a subcutaneous mouse melanoma model when injected in vivo.

Although not limited to the embodiments described in the working examples below, those examples illustrate two embodiments of nano-aAPC: (1) biocompatible iron-dextran paramagnetic beads 50-100 nm in diameter; and (2) avidin-coated quantum dot nanocrystals less than 20 nm in diameter. In these embodiments, signal 1 is provided by peptide-MHC complexes, and signal 2 is provided by B7.1-Ig or anti-CD28.

Nano-aAPC permit exploration of new particle-based immunotherapy strategies. As noted above, microscale aAPC are too large to be carried by lymphatics, and when injected subcutaneously remain at the injection site. When injected intravenously, they lodge in capillary beds. In fact, the poor trafficking of microscale beads has precluded the study of where aAPC should traffic for optimal immunotherapy. Trafficking and biodistribution of nano-aAPC is likely to be more efficient than microscale aAPC and will therefore allow the exploration of new in vivo immunotherapy strategies.

For example, two potential sites where an aAPC might be most effective are the lymph node, where naive and memory T cells reside, and the tumor itself. Nanoparticles of approximately 50-100 nm diameter can be taken up by lymphatics and transported to the lymph nodes (8, 30), thus gaining access to a larger pool of T cells. As described in the Examples below, subcutaneous injection of nano-aAPC resulted in less tumor growth than controls or intravenously injected beads. This points to drainage of nano-aAPC from the extracellular space to lymph nodes as a potential mechanism for optimal in vivo T cell expansion. In addition, nanoscale delivery vehicles preferentially accumulate in tumors through the Enhanced Permeability Retention effect due to poorly formed tumor vasculature (45, 46). By delivering a immunostimulatory signal in situ, aAPC in the tumor microenvironment may address one of the most prominent hurdles in cancer immunotherapy, the immunosuppressive tumor microenvironment (47).

In some embodiments, stimulation of naïve T cell responses can be achieved by clustering nano-aAPC after administration to a patient. Two strategies are illustrated in Example 7, below, although other strategies can be used. In the first strategy, magnetic nano-aAPC beads were used to enrich for anti-tumor, antigen specific T cells prior to stimulation. While not wishing to be bound by this explanation, we think enrichment increases cytokine availability and provides a better environment for T cell expansion in vitro. In the second strategy, magnetic nano-aAPC beads and T cells were incubated in a magnetic field, which boosts nano-aAPC mediated activation. This strategy required the development of an in vitro culture system based on commercially available cell enrichment columns, which are not intended for short-term cell culture or magnet-induced activation. Clustering also can be achieved, for example, using a secondary antibody or bead that "caps" the nano-aAPC. For example, cross-linking antibodies against proteins on the nano-aAPC or oligomerizing molecules (e.g., oligonucleotides or antibodies to the nano-aAPC surface) can be used to achieve clustering.

Use of nano-aAPC for ex vivo expansion of antigen-specific T cells and antibody-specific B cells, respectively, has a number of important advantages. Nano-aAPC can be preformed, have reproducible antigen presenting or antibody inducing activity, and can be used for a large patient population. The use of nano-aAPC dramatically simplifies and shortens the ex vivo expansion process of antigen-specific T cells compared to methods using dendritic cells and can induce expansion of precursor T or B cells to numbers suitable for therapeutic use. In addition, nano-aAPC can combine precursor T or B cell isolation with antigen-specific stimulation in one step.

T cell receptors are internalized after engagement (40), suggesting the possibility for nano-aAPC to both stimulate T cell receptors and subsequently deliver intracellular cargo such as siRNA.

While TCR-MHC interactions have been extensively studied for MHC presented on cells[7] and cell-sized, MHC-coated particles,[8-11] receptor-ligand interactions at the cell-nanoparticle interface have not been well understood.[12] As described below and in the specific examples, nanoparticle binding and cellular activation are sensitive to membrane spatial organization, which is particularly important during T cell activation, and magnetic fields can be used to manipulate cluster-bound nanoparticles to enhance activation. For example, T cell activation induces a state of persistently enhanced nanoscale TCR clustering[13-16] and, as described below, nanoparticles are sensitive to this clustering in a way that larger particles are not.

Furthermore, nanoparticle interactions with TCR clusters can be exploited to enhance receptor triggering. T cell activation is mediated by aggregation of signaling proteins,[17] with "signaling clusters" hundreds of nanometers across, initially forming at the periphery of the T cell-APC contact site and migrating inward.[18] As described below, an external magnetic field can be used to drive aggregation of paramagnetic nano-aAPC bound to TCR, resulting in aggregation of TCR clusters and enhanced activation of naive T cells.

Magnetic fields can exert appropriately strong forces on paramagnetic particles, but are otherwise biologically inert, making them a powerful tool to control particle behavior.[19,20] In methods described below, T cells bound to paramagnetic nano-aAPC are activated in the presence of an externally applied magnetic field. Nano-aAPC are themselves magnetized, and attracted to both the field source and to nearby nanoparticles in the field,[20,21] inducing bead and thus TCR aggregation to boost aAPC-mediated activation.

As demonstrated in the specific examples below, nano-aAPC bind more TCR on and induce greater activation of previously activated compared to naive T cells. In addition, application of an external magnetic field induces nano-aAPC aggregation on naive cells, enhancing T cells proliferation both in vitro and following adoptive transfer in vivo. Importantly, in a melanoma adoptive immunotherapy model, T cells activated by nano-aAPC in a magnetic field mediate tumor rejection. Thus, the use of applied magnetic fields permits activation of naive T cell populations, which otherwise are poorly responsive to stimulation. This is an important feature of immunotherapy as naive T cells have been shown to be more effective than more differentiated subtypes for cancer immunotherapy,[43-45] with higher proliferative capacity and greater ability to generate strong, long-term T cell responses. Thus, this disclosure provides a novel approach whereby nano-aAPC can be coupled to magnetic field enhanced activation of T cells to increase the yield and activity of antigen-specific T cells expanded from naive precursors, improving cellular therapy for, e.g., patients with infectious diseases, cancer, or autoimmune diseases, or to provide prophylactic protection to immunosuppressed patients.

Nano-aAPC

Unless otherwise indicated, a "nano-aAPC" includes at least one lymphocyte-effecting molecule and at least one antigen presenting complex that comprises at least one antigen binding cleft. Optionally, an antigen can be bound to the antigen binding cleft.

In some embodiments, a nano-aAPC includes at least one T cell affecting molecule and at least one antigen presenting complex that comprises at least one antigen binding cleft. Optionally, an antigen can be bound to the antigen binding cleft.

Nano-aAPC can be used to stimulate antibody formation. In these embodiments (also referred to herein as "antibody-inducing nano-aAPC"), a nano-aAPC comprises at least one B cell affecting molecule (e.g., CD40 ligand, a cytokine, or a cytokine molecular complex, described below) and at least one molecular complex that engages B cell surface immunoglobulins or engages MHC-antigen complexes on the surface of a B cell.

Nanoparticles

Nanoparticles can be made, for example, out of metals such as iron, nickel, aluminum, copper, zinc, cadmium, titanium, zirconium, tin, lead, chromium, manganese and cobalt; metal oxides and hydrated oxides such as aluminum oxide, chromium oxide, iron oxide, zinc oxide, and cobalt oxide; metal silicates such as of magnesium, aluminum, zinc, lead, chromium, copper, iron, cobalt, and nickel; alloys such as bronze, brass, stainless steel, and so forth. Nanoparticles can also be made of non-metal or organic materials such as cellulose, ceramics, glass, nylon, polystyrene, rubber, plastic, or latex. In some embodiments, nanoparticles comprise a combination of a metal and a non-metal or organic compound, for example, methacrylate- or styrene-coated metals and silicate coated metals. The base material can be doped with an agent to alter its physical or chemical properties. For example, rare earth oxides can be included in aluminosilicate glasses to create a paramagnetic glass materials with high density (see White & Day, *Key Engineering Materials Vol.* 94-95, 181-208, 1994). In some embodiments, nanoparticles comprise or consist of biodegradable organic materials, such as cellulose, dextran, and the like. Suitable commercially available particles include, for example, nickel particles (Type 123, VM 63, 18/209A, 10/585A, 347355 and HDNP sold by Novamet Specialty Products, Inc., Wyckoff, N.J.; 08841R sold by Spex, Inc.; 01509BW sold by Aldrich), stainless steel particles (P316L sold by Ametek), zinc dust (Aldrich), palladium particles (D13A17, John Matthey Elec.), and $TiO_2$, $SiO_2$, or $MnO_2$ particles (Aldrich).

The density of particles can be selected such that the particles will differentially settle through a sample suspension more rapidly than cells. Thus, particles preferably are composed of a high-density material to facilitate cell separation and manipulation of the particles. Use of such particles permits the particles to settle under gravity to facilitate their separation from antigen-specific T cells, T cell precursors, B cell precursors, B cells, or other cells.

In some embodiments, a nanoparticle is coated before proteins are bound to its surface. Once a coating chemistry has been chosen, the surface of a nanoparticle can be activated to allow the specific attachment of particular protein molecules. Thus, coatings can be selected with a view to optimal reactivity and biocompatibility with various T or B cell populations or T or B precursor cell populations. Preferably, whatever coating chemistry is used provides a suitable matrix for further activation chemistry. Numerous such coatings are well known in the art. For example, nanoparticle can be coated with human serum albumin, tris (3-mercaptopropyl)-N-glycylamino) methane (U.S. Pat. No. 6,074,884), gelatin-aminodextrans (U.S. Pat. No. 5,466, 609), or amino acid homopolymers or random copolymers. In some embodiments, a random amino acid copolymer comprising poly(glutamate, lysine, tyrosine) [6:3:1] is used; this copolymer is available from Sigma Chemical Co. as Product No. P8854. It is a linear random polymer of the amino acids glutamic acid, lysine, and tyrosine in a ratio of 6 parts glutamic acid, 3 parts lysine, and 1 part tyrosine. In some embodiments, an amino acid copolymer is used that includes lysine and tyrosine in a ratio of 4 parts lysine to 1 part tyrosine. In some embodiments, an amino acid copolymer is used that includes lysine and alanine in a ratio of 1 part lysine to 1 part alanine.

In some embodiments, a nanoparticle is coated with a synthetic polymer, then the synthetic polymer is activated before it is linked to a protein molecule including, but not limited to, a T or B cell affecting molecule, an antigen presenting complex, or a molecular complex that engages B cell surface immunoglobulins or MHC-antigen complexes on a B cell surface.

In some embodiments, particularly well suited for nickel surfaces (especially particles), a nanoparticle is coated with silica. A silica surface has several advantages over the more commonly used organic polymer surfaces. It is highly uniform, chemically defined, and chemically and thermally stable, with silanol residues covering the entire surface and available for stable covalent coupling with amino- or epoxy-derivatives of triethoxysilanes for attaching proteins and other biomolecules. Silane derivatives can cover the entire surface, forming a monolayer of a two-dimensional polymer that permits a high degree of control over specific and non-specific interactions on the surface. Methods for coating various solid supports with silica are disclosed in U.S. Pat. No. 2,885,399; see also Birkmeyer et al., Clin Chem. 1987 September; 33(9):1543-7. For example, a nanoparticle can be incubated with a solution of sodium metasilicate, sodium aluminate, and boric acid to form polymerized silica that deposits on the surface. Another method of silica coating is to mix sodium silicate with the nanoparticle and lower the pH with sulfuric acid at 95° C., followed by water washes. See U.S. Pat. No. 2,885,366; Eagerton, KONA 16, 46-58, 1998. For example, nickel surfaces can be coated by first dispersing them in a 0.2 N $NaSO_4$ solution and heating the solution to 95° C. The pH is adjusted to 10 with NaOH.

Sodium silicate in sulfuric acid is then added and mixed at 95° C. for 0.5 hours. The support is washed several times with distilled water. The extent of coating can be examined by determining the resistance of the support to nitric acid digestion. ESCA analysis for surface chemical composition, which is based on X-ray scattering, can be used to obtain the elemental composition of a support surface, providing information on the degree of surface coating and silanation with active residues.

In some embodiments, a surface matrix on a nanoparticle is provided by "passivating" a nickel surface with a non-toxic metal oxide coating, such as aluminum oxide. Other methods of coating include depositing metal oxides such as aluminum oxide to the surface of the nanoparticle. Aluminum oxide is a useful matrix because it provides an inert surface with low nonspecific binding properties that can be functionalized for protein conjugation.

An aluminum oxide coating can be provided by a number of methods, such as the sol-gel process, in which a thin, continuous layer of amorphous aluminum oxide is formed by evaporation of an aluminum sol-gel onto the nanoparticle, followed by baking in air to form the oxide. Ozer et al, *SPIE* 3789, 77-83, 1999. In other embodiments, conventional physical vapor deposition techniques (Smidt, *Inter Mat Rev* 35, 21-27, 1990) or chemical vapor deposition (Koh et al., *Thin Solid Films* 304, 222-24, 1997) can be used. If a nickel nanoparticle is used, the thickness of such coatings can be controlled to provide adequate stability while minimizing nickel leaching. The success of sealing the nickel can be tested by quantitative chemical assays of nickel ions. Nanoparticles can be incubated at various temperatures in various buffers and biological fluids, and the levels of nickel ions in these media can be measured.

The completeness of a surface coating can be determined through surface leaching assays. For example, when the surface of a nickel nanoparticle is completely coated by glass or other non-reactive metal, the nanoparticle is resistant to nickel leaching under acidic conditions. For example, a known mass of coated nickel nanoparticles can be incubated in 10% nitric acid and observed for 24 hours. As nickel is dissolved the solution turns green. Untreated nickel turns the solution green immediately. Nickel nanoparticles that have a nickel oxide layer on their surface turn the solution green in about 20 minutes. Nanoparticles coated with a layer of silica as described above are resistant to nitric acid for greater than 8 hours, which indicates that a thick layer of silica deposited on the surface. Nanoparticles can also be tested in aqueous conditions by incubating the supports in cell culture medium similar to the culture conditions used for B or T cell activation (described below). The amount of nickel leached into the solution can be measured by atomic absorption spectrometry.

If desired, nanoparticles can be pre-treated before being coated. Pre-treatment of a nanoparticle, for example, can sterilize and depyrogenated the support, as well as create an oxide layer on the support's surface. This pretreatment is particularly beneficial when metallic nanoparticles are used. In some embodiments, pre-treatment involves heating a nickel nanoparticle for about 2-6 hours, preferably for about 5 hours, at a temperature within the range of about 200-350° C., preferably about 250° C.

Molecules can be directly attached to nanoparticles by adsorption or by direct chemical bonding, including covalent bonding. See, e.g., Henuanson, BIOCONJUGATE TECHNIQUES, Academic Press, New York, 1996. A molecule itself can be directly activated with a variety of chemical functionalities, including nucleophilic groups, leaving groups, or electrophilic groups. Activating functional groups include alkyl and acyl halides, amines, sulfhydryls, aldehydes, unsaturated bonds, hydrazides, isocyanates, isothiocyanates, ketones, and other groups known to activate for chemical bonding. Alternatively, a molecule can be bound to a nanoparticle through the use of a small molecule-coupling reagent. Non-limiting examples of coupling reagents include carbodiimides, maleimides, N-hydroxysuccinimide esters, bischloroethylamines, bifunctional aldehydes such as glutaraldehyde, anyhydrides and the like. In other embodiments, a molecule can be coupled to a nanoparticle through affinity binding such as a biotinstreptavidin linkage or coupling, as is well known in the art. For example, streptavidin can be bound to a nanoparticle by covalent or non-covalent attachment, and a biotinylated molecule can be synthesized using methods that are well known in the art. See, for example, Hermanson, 1996.

If covalent binding to a nanoparticle is contemplated, the support can be coated with a polymer that contains one or more chemical moieties or functional groups that are available for covalent attachment to a suitable reactant, typically through a linker. For example, amino acid polymers can have groups, such as the s-amino group of lysine, available to couple a molecule covalently via appropriate linkers. This disclosure also contemplates placing a second coating on a nanoparticle to provide for these functional groups.

Activation chemistries can be used to allow the specific, stable attachment of molecules to the surface of nanoparticles. There are numerous methods that can be used to attach proteins to functional groups; see Hermanson, 1996. For example, the common cross-linker glutaraldehyde can be used to attach protein amine groups to an aminated nanoparticle surface in a two-step process. The resultant linkage is hydrolytically stable. Other methods include use of cross-linkers containing n-hydro-succinimido (NHS) esters which react with amines on proteins, cross-linkers containing active halogens that react with amine-, sulfhydryl-, or histidine-containing proteins, cross-linkers containing epoxides that react with amines or sulfhydryl groups, conjugation between maleimide groups and sulfhydryl groups, and the formation of protein aldehyde groups by periodate oxidation of pendant sugar moieties followed by reductive amination.

In some embodiments, protein molecules are attached to a silica coating using 3-aminopropyltriethoxysilane (Weetall & Filbert, *Methods Enzymol.* 34, 59-72, 1974). This compound forms a stable covalent bond with a silica surface and at the same time renders the surface more hydrophobic. The silanation reaction can be conducted in an aqueous low pH medium, which is known to allow the formation of a monolayer with the amino groups available for conjugation. The attachment of proteins can be via the homobifunctional coupling agent glutaraldehyde or by a heterobifunctional agents such as SMCC. After protein attachment, residual surface-associated coupling agents can be activated by incubating with various proteins, hydrophilic polymers, and amino acids. Albumin and polyethylene glycols are particularly suitable because they block non-specific binding of proteins and cells to solid phases.

In some embodiments, aminosilanation is used to activate the surface of aluminum oxide-coated nanoparticles. See U.S. Pat. No. 4,554,088 1985. Another method of activating the surface of the aluminum oxide coated nanoparticles is to adsorb a strongly adhering polymer, such as a glu-lys-tyr tripeptide. The tripeptide polymer can be activated through the lysine amines by reaction with a homobifunctional cross-linker, such as difluorodinitrobenzene, or by reaction with glutaraldehyde. Proteins can then be attached directly to the activated surface.

The attachment of specific proteins to a nanoparticle surface can be accomplished by direct coupling of the protein or by using indirect methods. Certain proteins will lend themselves to direct attachment or conjugation while other proteins or antibodies retain better functional activity when coupled to a linker or spacer protein such as anti-mouse IgG or streptavidin. If desired, linkers or attachment proteins can be used.

The ratio of particular proteins on the same nanoparticle can be varied to increase the effectiveness of the nanoparticle in antigen or antibody presentation. For example, optimal ratios of A2-Ig (Signal 1) to anti-CD28 (Signal 2) can be tested as follows. Nanoparticles are coupled with A2-Ig and anti-CD28 at a variety of ratios, such as 30:1, 10:1, 3:1, 1:1, 0.3:1; 0.1:1, and 0.03:1. The total amount of protein coupled to the supports is kept constant (for example, at 150 mg/ml of particles) or can be varied. Because effector functions such as cytokine release and growth may have differing requirements for Signal 1 versus Signal 2 than T cell activation and differentiation, these functions can be assayed separately.

Nanoparticles can be characterized by several analytical assays to evaluate the additions and reactions taking place as supports are produced. These include assays for functional groups, such as amines and aldehydes, and assays for the binding of particular types of protein molecules. In addition, functional assays can be used to evaluate biological activity of the nanoparticles. The amount of protein bound to the surface of nanoparticles can be determined by any method known in the art. For example, bound protein can be measured indirectly by determining the amount of protein that is removed from the reaction solution using absorbance at 280 nm. In this embodiment, the protein content of the reaction solution before and after addition to the nanoparticle is measured by absorbance at 280 nm and compared. The amount of protein contained in any wash solutions is also measured and added to the amount found in the post reaction solution. The difference is indicative of the amount bound to the surface of the nanoparticle. This method can be used to rapidly screen for binding efficiency of different reaction conditions.

In some embodiments, the amount of protein bound to nanoparticles can be measured in a more direct assay by binding assays of labeled antigens and antibodies. For example, various concentration of antibody-conjugated nanoparticles can be incubated with a constant concentration of HRP-labeled antigen or goat-anti-mouse IgG. The supports are washed in buffer to remove unbound labeled protein. Measuring the support-associated HRP using OPD substrate gives the concentration of bound labeled protein. HRP-labeled antibodies can be obtained commercially or antibodies can be labeled with HRP using the glutaraldehyde method of Avrameas & Ternync, *Immunochemistry* 8, 1175-79, 1971.

The methods described above measure both covalently bound and non-covalently bound protein. To distinguish between the two types of binding, nanoparticles can be washed with a strong chaotrope, such as 6 M guanidine hydrochloride or 8 M urea. Non-specific binding is disrupted by these conditions, and the amount of protein washed off the nanoparticles can be measured by absorbance at 280 nm. The difference between the total amount of protein bound and the amount washed off with the chaotrope represents the amount of protein that is tightly bound and is likely to be covalently attached.

The configuration of nanoparticles can vary from being irregular in shape to being spherical and/or from having an uneven or irregular surface to having a smooth surface. Preferred characteristics of nanoparticles can be selected depending on the particular conditions under which an ATR will be prepared and/or used.

Nanoparticles may be of uniform or variable size. Particle size distribution can be conveniently determined, for example, using dynamic light scattering.

In some embodiments, nanoparticles have a mean particle diameter of 2-500 nm.

In some embodiments nm, nanoparticles have a mean particle diameter of 2-3 nm, 2-4 nm, 2-5 nm, 2-6 nm, 2-7 nm, 2-8 nm, 2-9 nm, 2-10 nm, 2-11 nm, 2-12 nm, 2-13 nm, 2-14 nm, 2-15 nm, 2-16 nm, 2-17 nm, 2-18 nm, 2-19 nm, 2-20 nm, 2-21 nm, 2-22 nm, 2-23 nm, 2-24 nm, 2-25 nm, 2-26 nm, 2-27 nm, 2-28 nm, 2-29 nm, 2-30 nm, 3-4 nm, 3-5 nm, 3-6 nm, 3-7 nm, 3-8 nm, 3-9 nm, 3-10 nm, 3-11 nm, 3-12 nm, 3-13 nm, 3-14 nm, 3-15 nm, 3-16 nm, 3-17 nm, 3-18 nm, 3-19 nm, 3-20 nm, 3-21 nm, 3-22 nm, 3-23 nm, 3-24 nm, 3-25 nm, 3-26 nm, 3-27 nm, 3-28 nm, 3-29 nm, 3-30 nm, 4-5 nm, 4-6 nm, 4-7 nm, 4-8 nm, 4-9 nm, 4-10 nm, 4-11 nm, 4-12 nm, 4-13 nm, 4-14 nm, 4-15 nm, 4-16 nm, 4-17 nm, 4-18 nm, 4-19 nm, 4-20 nm, 4-21 nm, 4-22 nm, 4-23 nm, 4-24 nm, 4-25 nm, 4-26 nm, 4-27 nm, 4-28 nm, 4-29 nm, 4-30 nm, 5-6 nm, 5-7 nm, 5-8 nm, 5-9 nm, 5-10 nm, 5-11 nm, 5-12 nm, 5-13 nm, 5-14 nm, 5-15 nm, 5-16 nm, 5-17 nm, 5-18 nm, 5-19 nm, 5-20 nm, 5-21 nm, 5-22 nm, 5-23 nm, 5-24 nm, 5-25 nm, 5-26 nm, 5-27 nm, 5-28 nm, 5-29 nm, 5-30 nm, 6-7 nm, 6-8 nm, 6-9 nm, 6-10 nm, 6-11 nm, 6-12 nm, 6-13 nm, 6-14 nm, 6-15 nm, 6-16 nm, 6-17 nm, 6-18 nm, 6-19 nm, 6-20 nm, 6-21 nm, 6-22 nm, 6-23 nm, 6-24 nm, 6-25 nm, 6-26 nm, 6-27 nm, 6-28 nm, 6-29 nm, 6-30 nm, 7-8 nm, 7-9 nm, 7-10 nm, 7-11 nm, 7-12 nm, 7-13 nm, 7-14 nm, 7-15 nm, 7-16 nm, 7-17 nm, 7-18 nm, 7-19 nm, 7-20 nm, 7-21 nm, 7-22 nm, 7-23 nm, 7-24 nm, 7-25 nm, 7-26 nm, 7-27 nm, 7-28 nm, 7-29 nm, 7-30 nm, 8-9 nm, 8-10 nm, 8-11 nm, 8-12 nm, 8-13 nm, 8-14 nm, 8-15 nm, 8-16 nm, 8-17 nm, 8-18 nm, 8-19 nm, 8-20 nm, 8-21 nm, 8-22 nm, 8-23 nm, 8-24 nm, 8-25 nm, 8-26 nm, 8-27 nm, 8-28 nm, 8-29 nm, 8-30 nm, 9-10 nm, 9-11 nm, 9-12 nm, 9-13 nm, 9-14 nm, 9-15 nm, 9-16 nm, 9-17 nm, 9-18 nm, 9-19 nm, 9-20 nm, 9-21 nm, 9-22 nm, 9-23 nm, 9-24 nm, 9-25 nm, 9-26 nm, 9-27 nm, 9-28 nm, 9-29 nm, 9-30 nm, 10-11 nm, 10-12 nm, 10-13 nm, 10-14 nm, 10-15 nm, 10-16 nm, 10-17 nm, 10-18 nm, 10-19 nm, 10-20 nm, 10-21 nm, 10-22 nm, 10-23 nm, 10-24 nm, 10-25 nm, 10-26 nm, 10-27 nm, 10-28 nm, 10-29 nm, 10-30 nm, 11-12 nm, 11-13 nm, 11-14 nm, 11-15 nm, 11-16 nm, 11-17 nm, 11-18 nm, 11-19 nm, 11-20 nm, 11-21 nm, 11-22 nm, 11-23 nm, 11-24 nm, 11-25 nm, 11-26 nm, 11-27 nm, 11-28 nm, 11-29 nm, 11-30 nm, 12-13 nm, 12-14 nm, 12-15 nm, 12-16 nm, 12-17 nm, 12-18 nm, 12-19 nm, 12-20 nm, 12-21 nm, 12-22 nm, 12-23 nm, 12-24 nm, 12-25 nm, 12-26 nm, 12-27 nm, 12-28 nm, 12-29 nm, 12-30 nm, 13-14 nm, 13-15 nm, 13-16 nm, 13-17 nm, 13-18 nm, 13-19 nm, 13-20 nm, 13-21 nm, 13-22 nm, 13-23 nm, 13-24 nm, 13-25 nm, 13-26 nm, 13-27 nm, 13-28 nm, 13-29 nm, 13-30 nm, 14-15 nm, 14-16 nm, 14-17 nm, 14-18 nm, 14-19 nm, 14-20 nm, 14-21 nm, 14-22 nm, 14-23 nm, 14-24 nm, 14-25 nm, 14-26 nm, 14-27 nm, 14-28 nm, 14-29 nm, 14-30 nm, 15-16 nm, 15-17 nm, 15-18 nm, 15-19 nm, 15-20 nm, 15-21 nm, 15-22 nm, 15-23 nm, 15-24 nm, 15-25 nm, 15-26 nm, 15-27 nm, 15-28 nm, 15-29 nm, 15-30 nm, 16-17 nm, 16-18 nm, 16-19 nm, 16-20 nm, 16-21 nm, 16-22 nm, 16-23 nm, 16-24 nm, 16-25 nm, 16-26 nm, 16-27 nm, 16-28 nm, 16-29 nm, 16-30 nm, 17-18 nm, 17-19 nm, 17-20 nm, 17-21 nm, 17-22 nm, 17-23 nm, 17-24 nm, 17-25 nm, 17-26 nm, 17-27 nm, 17-28 nm, 17-29 nm, 17-30 nm, 18-19 nm, 18-20 nm, 18-21 nm, 18-22 nm, 18-23 nm, 18-24 nm, 18-25 nm, 18-26 nm, 18-27 nm, 18-28 nm, 18-29 nm, 18-30 nm, 19-20 nm, 19-21 nm, 19-22 nm, 19-23 nm, 19-24 nm, 19-25 nm, 19-26 nm, 19-27 nm, 19-28 nm, 19-29 nm, 19-30 nm, 20-21 nm, 20-22 nm, 20-23 nm, 20-24 nm, 20-25 nm, 20-26 nm, 20-27 nm, 20-28 nm, 20-29 nm, 20-30 nm, 21-21 nm, 21-22 nm, 21-23 nm, 21-24 nm, 21-25 nm, 21-26 nm, 21-27 nm, 21-28 nm, 21-29 nm, 21-30 nm, 22-23 nm, 22-24 nm, 22-25 nm, 22-26 nm, 22-27 nm, 22-28 nm, 22-29 nm, 22-30 nm, 23-24 nm, 23-25 nm, 23-26 nm, 23-27 nm, 23-28 nm, 23-29 nm, 23-30 nm, 24-25 nm, 24-26 nm, 24-27 nm, 24-28 nm, 24-29 nm, 24-30 nm, 25-26 nm, 25-27 nm, 25-28 nm, 25-29 nm, 25-30 nm, 26-27 nm, 26-28 nm, 26-29 nm, 26-30 nm, 27-28 nm, 27-29 nm, 27-30 nm, 28-29 nm, 28-30 nm, or 29-30 nm.

In some embodiments, nanoparticles have a mean particle diameter of 25-500 nm+/−5 nm, 25-500 nm+/−10 nm, 25-500 nm+/−15 nm, 25-500 nm+/−20 nm, 25-500 nm+/−25 nm, 25-500 nm+/−30 nm, 25-500 nm+/−35 nm, 25-500 nm+/−40 nm, 25-500 nm+/−45 nm, or 25-500 nm+/−50 nm.

In some embodiments, nanoparticles have a mean particle diameter of 25-30 nm, 25-35 nm, 25-40 nm, 25-45 nm, 25-50 nm, 25-55 nm, 25-60 nm, 25-70 nm, 25-75 nm, 25-80 nm, 25-90 nm, 25-95 nm, 25-100 nm, 25-125 nm, 25-150 nm, 25-200 nm, 25-300 nm, 25-400 nm, 30-35 nm, 35-40 nm, 35-45 nm, 35-50 nm, 35-55 nm, 35-60 nm, 35-70 nm, 35-75 nm, 35-80 nm, 35-90 nm, 35-95 nm, 35-100 nm, 35-125 nm, 35-150 nm, 35-200 nm, 35-300 nm, 35-400, 35-500 nm, 40-45 nm, 35-50 nm, 45-55 nm, 45-60 nm, 45-70 nm, 45-75 nm, 45-80 nm, 45-90 nm, 45-95 nm, 45-100 nm, 45-125 nm, 45-150 nm, 45-200 nm, 45-300 nm, 45-400, 45-500 nm, 50-55 nm, 50-60 nm, 50-70 nm, 50-75 nm, 50-80 nm, 50-90 nm, 50-95 nm, 50-100 nm, 50-125 nm, 50-150 nm, 50-200 nm, 50-300 nm, 50-400 nm, 50-500 nm, 55-60 nm, 55-70 nm, 55-75 nm, 55-80 nm, 55-90 nm, 55-95 nm, 55-100 nm, 55-125 nm, 55-150 nm, 55-200 nm, 55-300 nm, 55-400 nm, 55-500 nm, 60-70 nm, 60-75 nm, 60-80 nm, 60-90 nm, 60-95 nm, 60-100 nm, 60-125 nm, 60-150 nm, 60-200 nm, 60-300 nm, 60-400, 60-500 nm, 65-70 nm, 65-75 nm, 65-80 nm, 65-90 nm, 65-95 nm, 65-100 nm, 65-125 nm, 65-150 nm, 65-200 nm, 65-300 nm, 65-400, 65-500 nm, 70-75 nm, 70-80 nm, 70-90 nm, 70-95 nm, 70-100 nm, 70-125 nm, 70-150 nm, 70-200 nm, 70-300 nm, 70-400, 70-500 nm, 75-80 nm, 75-90 nm, 75-95 nm, 75-100 nm, 75-125 nm, 75-150 nm, 75-200 nm, 75-300 nm, 75-400, 75-500 nm, 80-90 nm, 80-95 nm, 80-100 nm, 80-125 nm, 80-150 nm, 80-200 nm, 80-300 nm, 80-400, 80-500 nm, 85-90 nm, 85-95 nm, 85-100 nm, 85-125 nm, 85-150 nm, 85-200 nm, 85-300 nm, 85-400, 85-500 nm, 90-95 nm, 90-100 nm, 90-125 nm, 90-150 nm, 90-200 nm, 90-300 nm, 90-400, 90-500 nm, 100-125 nm, 100-150 nm, 100-200 nm, 100-300 nm, 100-400, 100-500 nm, 125-150 nm, 125-200 nm, 125-300 nm, 125-400, 125-500 nm, 150-200 nm, 150-300 nm, 150-400, 150-500 nm, 175-200 nm, 175-300 nm, 175-400, 175-500 nm, 200-300 nm, 200-400, 200-500 nm, 300-400, 300-500 nm, or 400-500 nm.

In some embodiments, nanoparticles have a mean particle diameter of 25-30 nm+/−5 nm, 25-35 nm+/−5 nm, 25-40 nm+/−5 nm, 25-45 nm+/−5 nm, 25-50 nm+/−5 nm, 25-55 nm+/−5 nm, 25-60 nm+/−5 nm, 25-70 nm+/−5 nm, 25-75 nm+/−5 nm, 25-80 nm+/−5 nm, 25-90 nm+/−5 nm, 25-95 nm+/−5 nm, 25-100 nm+/−5 nm, 25-125 nm+/−5 nm, 25-150 nm+/−5 nm, 25-200 nm+/−5 nm, 25-300 nm+/−5 nm, 25-400 nm+/−5 nm, 30-35 nm+/−5 nm, 35-40 nm+/−5 nm, 35-45 nm+/−5 nm, 35-50 nm+/−5 nm, 35-55 nm+/−5 nm, 35-60 nm+/−5 nm, 35-70 nm+/−5 nm, 35-75 nm+/−5 nm, 35-80 nm+/−5 nm, 35-90 nm+/−5 nm, 35-95 nm+/−5 nm, 35-100 nm+/−5 nm, 35-125 nm+/−5 nm, 35-150 nm+/−5 nm, 35-200 nm+/−5 nm, 35-300 nm+/−5 nm, 35-400, 35-500 nm+/−5 nm, 40-45 nm+/−5 nm, 35-50 nm+/−5 nm, 45-55 nm+/−5 nm, 45-60 nm+/−5 nm, 45-70 nm+/−5 nm, 45-75 nm+/−5 nm, 45-80 nm+/−5 nm, 45-90 nm+/−5 nm, 45-95 nm+/−5 nm, 45-100 nm+/−5 nm, 45-125 nm+/−5 nm, 45-150 nm+/−5 nm, 45-200 nm+/−5 nm, 45-300 nm+/−5 nm, 45-400, 45-500 nm+/−5 nm, 50-55 nm+/−5 nm, 50-60 nm+/−5 nm, 50-70 nm+/−5 nm, 50-75 nm+/−5 nm, 50-80 nm+/−5 nm, 50-90 nm+/−5 nm, 50-95 nm+/−5 nm, 50-100 nm+/−5 nm, 50-125 nm+/−5 nm, 50-150 nm+/−5 nm, 50-200 nm+/−5 nm, 50-300 nm+/−5 nm, 50-400, 50-500 nm+/−5 nm, 55-60 nm+/−5 nm, 55-70 nm+/−5 nm, 55-75 nm+/−5 nm, 55-80 nm+/−5 nm, 55-90 nm+/−5 nm, 55-95 nm+/−5 nm, 55-100 nm+/−5 nm, 55-125 nm+/−5 nm, 55-150 nm+/−5 nm, 55-200 nm+/−5 nm, 55-300 nm+/−5 nm, 55-400, 55-500 nm+/−5 nm, 60-70 nm+/−5 nm, 60-75 nm+/−5 nm, 60-80 nm+/−5 nm, 60-90 nm+/−5 nm, 60-95 nm+/−5 nm, 60-100 nm+/−5 nm, 60-125 nm+/−5 nm, 60-150 nm+/−5 nm, 60-200 nm+/−5 nm, 60-300 nm+/−5 nm, 60-400, 60-500 nm+/−5 nm, 65-70 nm+/−5 nm, 65-75 nm+/−5 nm, 65-80 nm+/−5 nm, 65-90 nm+/−5 nm, 65-95 nm+/−5 nm, 65-100 nm+/−5 nm, 65-125 nm+/−5 nm, 65-150 nm+/−5 nm, 65-200 nm+/−5 nm, 65-300 nm+/−5 nm, 65-400, 65-500 nm+/−5 nm, 70-75 nm+/−5 nm, 70-80 nm+/−5 nm, 70-90 nm+/−5 nm, 70-95 nm+/−5 nm, 70-100 nm+/−5 nm, 70-125 nm+/−5 nm, 70-150 nm+/−5 nm, 70-200 nm+/−5 nm, 70-300 nm+/−5 nm, 70-400, 70-500 nm+/−5 nm, 75-80 nm+/−5 nm, 75-90 nm+/−5 nm, 75-95 nm+/−5 nm, 75-100 nm+/−5 nm, 75-125 nm+/−5 nm, 75-150 nm+/−5 nm, 75-200 nm+/−5 nm, 75-300 nm+/−5 nm, 75-400, 75-500 nm+/−5 nm, 80-90 nm+/−5 nm, 80-95 nm+/−5 nm, 80-100 nm+/−5 nm, 80-125 nm+/−5 nm, 80-150 nm+/−5 nm, 80-200 nm+/−5 nm, 80-300 nm+/−5 nm, 80-400, 80-500 nm+/−5 nm, 85-90 nm+/−5 nm, 85-95 nm+/−5 nm, 85-100 nm+/−5 nm, 85-125 nm+/−5 nm, 85-150 nm+/−5 nm, 85-200 nm+/−5 nm, 85-300 nm+/−5 nm, 85-400, 85-500 nm+/−5 nm, 90-95 nm+/−5 nm, 90-100 nm+/−5 nm, 90-125 nm+/−5 nm, 90-150 nm+/−5 nm, 90-200 nm+/−5 nm, 90-300 nm+/−5 nm, 90-400, 90-500 nm+/−5 nm, 100-125 nm+/−5 nm, 100-150 nm+/−5 nm, 100-200 nm+/−5 nm, 100-300 nm+/−5 nm, 100-400, 100-500 nm+/−5 nm, 125-150 nm+/−5 nm, 125-200 nm+/−5 nm, 125-300 nm+/−5 nm, 125-400, 125-500 nm+/−5 nm, 150-200 nm+/−5 nm, 150-300 nm+/−5 nm, 150-400, 150-500 nm+/−5 nm, 175-200 nm+/−5 nm, 175-300 nm+/−5 nm, 175-400, 175-500 nm+/−5 nm, 200-300 nm+/−5 nm, 200-400, 200-500 nm+/−5 nm, 300-400, 300-500 nm+/−5 nm, or 400-500 nm+/−5 nm.

In some embodiments, nanoparticles have a mean particle diameter of 25-30 nm+/−10 nm, 25-35 nm+/−10 nm, 25-40 nm+/−10 nm, 25-45 nm+/−10 nm, 25-100 nm+/−10 nm, 25-105 nm+/−10 nm, 25-60 nm+/−10 nm, 25-70 nm+/−10 nm, 25-75 nm+/−10 nm, 25-80 nm+/−10 nm, 25-90 nm+/−10 nm, 25-95 nm+/−10 nm, 25-100 nm+/−10 nm, 25-125 nm+/−10 nm, 25-150 nm+/−10 nm, 25-200 nm+/−10 nm, 25-300 nm+/−10 nm, 25-400 nm+/−10 nm, 30-35 nm+/−10 nm, 35-40 nm+/−10 nm, 35-45 nm+/−10 nm, 35-100 nm+/−10 nm, 35-105 nm+/−10 nm, 35-60 nm+/−10 nm, 35-70 nm+/−10 nm, 35-75 nm+/−10 nm, 35-80 nm+/−10 nm, 35-90 nm+/−10 nm, 35-95 nm+/−10 nm, 35-100 nm+/−10 nm, 35-125 nm+/−10 nm, 35-150 nm+/−10 nm, 35-200 nm+/−10 nm, 35-300 nm+/−10 nm, 35-400, 35-1000 nm+/−

10 nm, 40-45 nm+/−10 nm, 35-100 nm+/−10 nm, 45-105 nm+/−10 nm, 45-60 nm+/−10 nm, 45-70 nm+/−10 nm, 45-75 nm+/−10 nm, 45-80 nm+/−10 nm, 45-90 nm+/−10 nm, 45-95 nm+/−10 nm, 45-100 nm+/−10 nm, 45-125 nm+/−10 nm, 45-150 nm+/−10 nm, 45-200 nm+/−10 nm, 45-300 nm+/−10 nm, 45-400, 45-1000 nm+/−10 nm, 50-105 nm+/−10 nm, 50-60 nm+/−10 nm, 50-70 nm+/−10 nm, 50-75 nm+/−10 nm, 50-80 nm+/−10 nm, 50-90 nm+/−10 nm, 50-95 nm+/−10 nm, 50-100 nm+/−10 nm, 50-125 nm+/−10 nm, 50-150 nm+/−10 nm, 50-200 nm+/−10 nm, 50-300 nm+/−10 nm, 50-400, 50-1000 nm+/−10 nm, 55-60 nm+/−10 nm, 55-70 nm+/−10 nm, 55-75 nm+/−10 nm, 55-80 nm+/−10 nm, 55-90 nm+/−10 nm, 55-95 nm+/−10 nm, 55-100 nm+/−10 nm, 55-125 nm+/−10 nm, 55-150 nm+/−10 nm, 55-200 nm+/−10 nm, 55-300 nm+/−10 nm, 55-400, 55-1000 nm+/−10 nm, 60-70 nm+/−10 nm, 60-75 nm+/−10 nm, 60-80 nm+/−10 nm, 60-90 nm+/−10 nm, 60-95 nm+/−10 nm, 60-100 nm+/−10 nm, 60-125 nm+/−10 nm, 60-150 nm+/−10 nm, 60-200 nm+/−10 nm, 60-300 nm+/−10 nm, 60-400, 60-1000 nm+/−10 nm, 65-70 nm+/−10 nm, 65-75 nm+/−10 nm, 65-80 nm+/−10 nm, 65-90 nm+/−10 nm, 65-95 nm+/−10 nm, 65-100 nm+/−10 nm, 65-125 nm+/−10 nm, 65-150 nm+/−10 nm, 65-200 nm+/−10 nm, 65-300 nm+/−10 nm, 65-400, 65-1000 nm+/−10 nm, 70-75 nm+/−10 nm, 70-80 nm+/−10 nm, 70-90 nm+/−10 nm, 70-95 nm+/−10 nm, 70-100 nm+/−10 nm, 70-125 nm+/−10 nm, 70-150 nm+/−10 nm, 70-200 nm+/−10 nm, 70-300 nm+/−10 nm, 70-400, 70-1000 nm+/−10 nm, 75-80 nm+/−10 nm, 75-90 nm+/−10 nm, 75-95 nm+/−10 nm, 75-100 nm+/−10 nm, 75-125 nm+/−10 nm, 75-150 nm+/−10 nm, 75-200 nm+/−10 nm, 75-300 nm+/−10 nm, 75-400, 75-1000 nm+/−10 nm, 80-90 nm+/−10 nm, 80-95 nm+/−10 nm, 80-100 nm+/−10 nm, 80-125 nm+/−10 nm, 80-150 nm+/−10 nm, 80-200 nm+/−10 nm, 80-300 nm+/−10 nm, 80-400, 80-1000 nm+/−10 nm, 85-90 nm+/−10 nm, 85-95 nm+/−10 nm, 85-100 nm+/−10 nm, 85-125 nm+/−10 nm, 85-150 nm+/−10 nm, 85-200 nm+/−10 nm, 85-300 nm+/−10 nm, 85-400, 85-1000 nm+/−10 nm, 90-95 nm+/−10 nm, 90-100 nm+/−10 nm, 90-125 nm+/−10 nm, 90-150 nm+/−10 nm, 90-200 nm+/−10 nm, 90-300 nm+/−10 nm, 90-400, 90-1000 nm+/−10 nm, 100-125 nm+/−10 nm, 100-150 nm+/−10 nm, 100-200 nm+/−10 nm, 100-300 nm+/−10 nm, 100-400, 100-1000 nm+/−10 nm, 125-150 nm+/−10 nm, 125-200 nm+/−10 nm, 125-300 nm+/−10 nm, 125-400, 125-1000 nm+/−10 nm, 150-200 nm+/−10 nm, 150-300 nm+/−10 nm, 150-400, 150-1000 nm+/−10 nm, 175-200 nm+/−10 nm, 175-300 nm+/−10 nm, 175-400, 175-1000 nm+/−10 nm, 200-300 nm+/−10 nm, 200-400, 200-1000 nm+/−10 nm, 300-400, 300-1000 nm+/−10 nm, or 400-1000 nm+/−10 nm.

In some embodiments, nanoparticles have a mean particle diameter of 25-30 nm+/−15 nm, 25-35 nm+/−15 nm, 25-40 nm+/−15 nm, 25-45 nm+/−15 nm, 25-150 nm+/−15 nm, 25-155 nm+/−15 nm, 25-60 nm+/−15 nm, 25-70 nm+/−15 nm, 25-75 nm+/−15 nm, 25-80 nm+/−15 nm, 25-90 nm+/−15 nm, 25-95 nm+/−15 nm, 25-100 nm+/−15 nm, 25-125 nm+/−15 nm, 25-150 nm+/−15 nm, 25-200 nm+/−15 nm, 25-300 nm+/−15 nm, 25-400 nm+/−15 nm, 30-35 nm+/−15 nm, 35-40 nm+/−15 nm, 35-45 nm+/−15 nm, 35-150 nm+/−15 nm, 35-155 nm+/−15 nm, 35-60 nm+/−15 nm, 35-70 nm+/−15 nm, 35-75 nm+/−15 nm, 35-80 nm+/−15 nm, 35-90 nm+/−15 nm, 35-95 nm+/−15 nm, 35-100 nm+/−15 nm, 35-125 nm+/−15 nm, 35-150 nm+/−15 nm, 35-200 nm+/−15 nm, 35-300 nm+/−15 nm, 35-400, 35-1500 nm+/−15 nm, 40-45 nm+/−15 nm, 35-150 nm+/−15 nm, 45-155 nm+/−15 nm, 45-60 nm+/−15 nm, 45-70 nm+/−15 nm, 45-75 nm+/−15 nm, 45-80 nm+/−15 nm, 45-90 nm+/−15 nm, 45-95 nm+/−15 nm, 45-100 nm+/−15 nm, 45-125 nm+/−15 nm, 45-150 nm+/−15 nm, 45-200 nm+/−15 nm, 45-300 nm+/−15 nm, 45-400, 45-1500 nm+/−15 nm, 50-155 nm+/−15 nm, 50-60 nm+/−15 nm, 50-70 nm+/−15 nm, 50-75 nm+/−15 nm, 50-80 nm+/−15 nm, 50-90 nm+/−15 nm, 50-95 nm+/−15 nm, 50-100 nm+/−15 nm, 50-125 nm+/−15 nm, 50-150 nm+/−15 nm, 50-200 nm+/−15 nm, 50-300 nm+/−15 nm, 50-400, 50-1500 nm+/−15 nm, 55-60 nm+/−15 nm, 55-70 nm+/−15 nm, 55-75 nm+/−15 nm, 55-80 nm+/−15 nm, 55-90 nm+/−15 nm, 55-95 nm+/−15 nm, 55-100 nm+/−15 nm, 55-125 nm+/−15 nm, 55-150 nm+/−15 nm, 55-200 nm+/−15 nm, 55-300 nm+/−15 nm, 55-400, 55-1500 nm+/−15 nm, 60-70 nm+/−15 nm, 60-75 nm+/−15 nm, 60-80 nm+/−15 nm, 60-90 nm+/−15 nm, 60-95 nm+/−15 nm, 60-100 nm+/−15 nm, 60-125 nm+/−15 nm, 60-150 nm+/−15 nm, 60-200 nm+/−15 nm, 60-300 nm+/−15 nm, 60-400, 60-1500 nm+/−15 nm, 65-70 nm+/−15 nm, 65-75 nm+/−15 nm, 65-80 nm+/−15 nm, 65-90 nm+/−15 nm, 65-95 nm+/−15 nm, 65-100 nm+/−15 nm, 65-125 nm+/−15 nm, 65-150 nm+/−15 nm, 65-200 nm+/−15 nm, 65-300 nm+/−15 nm, 65-400, 65-1500 nm+/−15 nm, 70-75 nm+/−15 nm, 70-80 nm+/−15 nm, 70-90 nm+/−15 nm, 70-95 nm+/−15 nm, 70-100 nm+/−15 nm, 70-125 nm+/−15 nm, 70-150 nm+/−15 nm, 70-200 nm+/−15 nm, 70-300 nm+/−15 nm, 70-400, 70-1500 nm+/−15 nm, 75-80 nm+/−15 nm, 75-90 nm+/−15 nm, 75-95 nm+/−15 nm, 75-100 nm+/−15 nm, 75-125 nm+/−15 nm, 75-150 nm+/−15 nm, 75-200 nm+/−15 nm, 75-300 nm+/−15 nm, 75-400, 75-1500 nm+/−15 nm, 80-90 nm+/−15 nm, 80-95 nm+/−15 nm, 80-100 nm+/−15 nm, 80-125 nm+/−15 nm, 80-150 nm+/−15 nm, 80-200 nm+/−15 nm, 80-300 nm+/−15 nm, 80-400, 80-1500 nm+/−15 nm, 85-90 nm+/−15 nm, 85-95 nm+/−15 nm, 85-100 nm+/−15 nm, 85-125 nm+/−15 nm, 85-150 nm+/−15 nm, 85-200 nm+/−15 nm, 85-300 nm+/−15 nm, 85-400, 85-1500 nm+/−15 nm, 90-95 nm+/−15 nm, 90-100 nm+/−15 nm, 90-125 nm+/−15 nm, 90-150 nm+/−15 nm, 90-200 nm+/−15 nm, 90-300 nm+/−15 nm, 90-400, 90-1500 nm+/−15 nm, 100-125 nm+/−15 nm, 100-150 nm+/−15 nm, 100-200 nm+/−15 nm, 100-300 nm+/−15 nm, 100-400, 100-1500 nm+/−15 nm, 125-150 nm+/−15 nm, 125-200 nm+/−15 nm, 125-300 nm+/−15 nm, 125-400, 125-1500 nm+/−15 nm, 150-200 nm+/−15 nm, 150-300 nm+/−15 nm, 150-400, 150-1500 nm+/−15 nm, 175-200 nm+/−15 nm, 175-300 nm+/−15 nm, 175-400, 175-1500 nm+/−15 nm, 200-300 nm+/−15 nm, 200-400, 200-1500 nm+/−15 nm, 300-400, 300-1500 nm+/−15 nm, or 400-1500 nm+/−15 nm.

In some embodiments, nanoparticles have a mean particle diameter of 25-30 nm+/−20 nm, 25-35 nm+/−20 nm, 25-40 nm+/−20 nm, 25-45 nm+/−20 nm, 25-200 nm+/−20 nm, 25-205 nm+/−20 nm, 25-60 nm+/−20 nm, 25-70 nm+/−20 nm, 25-75 nm+/−20 nm, 25-80 nm+/−20 nm, 25-90 nm+/−20 nm, 25-95 nm+/−20 nm, 25-100 nm+/−20 nm, 25-125 nm+/−20 nm, 25-150 nm+/−20 nm, 25-200 nm+/−20 nm, 25-300 nm+/−20 nm, 25-400 nm+/−20 nm, 30-35 nm+/−20 nm, 35-40 nm+/−20 nm, 35-45 nm+/−20 nm, 35-200 nm+/−20 nm, 35-205 nm+/−20 nm, 35-60 nm+/−20 nm, 35-70 nm+/−20 nm, 35-75 nm+/−20 nm, 35-80 nm+/−20 nm, 35-90 nm+/−20 nm, 35-95 nm+/−20 nm, 35-100 nm+/−20 nm, 35-125 nm+/−20 nm, 35-150 nm+/−20 nm, 35-200 nm+/−20 nm, 35-300 nm+/−20 nm, 35-400, 35-2000 nm+/−20 nm, 40-45 nm+/−20 nm, 35-200 nm+/−20 nm, 45-205 nm+/−20 nm, 45-60 nm+/−20 nm, 45-70 nm+/−20 nm, 45-75 nm+/−20 nm, 45-80 nm+/−20 nm, 45-90 nm+/−20 nm, 45-95 nm+/−20 nm, 45-100 nm+/−20 nm, 45-125 nm+/−20 nm, 45-150 nm+/−20 nm, 45-200 nm+/−20 nm, 45-300 nm+/−20 nm, 45-400, 45-2000 nm+/−20 nm, 50-205 nm+/−20 nm, 50-60 nm+/−20 nm, 50-70 nm+/−20 nm, 50-75 nm+/−20 nm, 50-80 nm+/−20 nm, 50-90 nm+/−20 nm, 50-95 nm+/−20 nm, 50-100 nm+/−20 nm, 50-125 nm+/−20 nm, 50-150 nm+/−20 nm, 50-200 nm+/−20 nm, 50-300 nm+/−20 nm, 50-400, 50-2000 nm+/−20 nm, 55-60 nm+/−20 nm, 55-70 nm+/−20 nm, 55-75 nm+/−20 nm, 55-80 nm+/−20 nm, 55-90 nm+/−20 nm, 55-95 nm+/−20 nm, 55-100 nm+/−20 nm, 55-125 nm+/−20 nm, 55-150 nm+/−20 nm, 55-200 nm+/−20 nm, 55-300 nm+/−20 nm, 55-400, 55-2000 nm+/−20 nm, 60-70 nm+/−20 nm, 60-75 nm+/−20 nm, 60-80 nm+/−20 nm, 60-90 nm+/−20 nm, 60-95 nm+/−20 nm, 60-100 nm+/−20 nm, 60-125 nm+/−20 nm, 60-150 nm+/−20 nm, 60-200 nm+/−20 nm, 60-300 nm+/−20 nm, 60-400, 60-2000 nm+/−20 nm, 65-70 nm+/−20 nm, 65-75 nm+/−20 nm, 65-80 nm+/−20 nm, 65-90 nm+/−20 nm, 65-95 nm+/−20 nm, 65-100 nm+/−20 nm, 65-125 nm+/−20 nm, 65-150 nm+/−20 nm, 65-200 nm+/−20 nm, 65-300 nm+/−20 nm, 65-400, 65-2000 nm+/−20 nm, 70-75 nm+/−20 nm, 70-80 nm+/−20 nm, 70-90 nm+/−20 nm, 70-95 nm+/−20 nm, 70-100 nm+/−20 nm, 70-125 nm+/−20 nm, 70-150 nm+/−20 nm, 70-200 nm+/−20 nm, 70-300 nm+/−20 nm, 70-400, 70-2000 nm+/−20 nm, 75-80 nm+/−20 nm, 75-90 nm+/−20 nm, 75-95 nm+/−20 nm, 75-100 nm+/−20 nm, 75-125 nm+/−20 nm, 75-150 nm+/−20 nm, 75-200 nm+/−20 nm, 75-300 nm+/−20 nm, 75-400, 75-2000 nm+/−20 nm, 80-90 nm+/−20 nm, 80-95 nm+/−20 nm, 80-100 nm+/−20 nm, 80-125 nm+/−20 nm, 80-150 nm+/−20 nm, 80-200 nm+/−20 nm, 80-300 nm+/−20 nm, 80-400, 80-2000 nm+/−20 nm, 85-90 nm+/−20 nm, 85-95 nm+/−20 nm, 85-100 nm+/−20 nm, 85-125 nm+/−20 nm, 85-150 nm+/−20 nm, 85-200 nm+/−20 nm, 85-300 nm+/−20 nm, 85-400, 85-2000 nm+/−20 nm, 90-95 nm+/−20 nm, 90-100 nm+/−20 nm, 90-125 nm+/−20 nm, 90-150 nm+/−20 nm, 90-200 nm+/−20 nm, 90-300 nm+/−20 nm, 90-400, 90-2000 nm+/−20 nm, 100-125 nm+/−20 nm, 100-150 nm+/−20 nm, 100-200 nm+/−20 nm, 100-300 nm+/−20 nm, 100-400, 100-2000 nm+/−20 nm, 125-150 nm+/−20 nm, 125-200 nm+/−20 nm, 125-300 nm+/−20 nm, 125-400, 125-2000 nm+/−20 nm, 150-200 nm+/−20 nm, 150-300 nm+/−20 nm, 150-400, 150-2000 nm+/−20 nm, 175-200 nm+/−20 nm, 175-300 nm+/−20 nm, 175-400, 175-2000 nm+/−20 nm, 200-300 nm+/−20 nm, 200-400, 200-2000 nm+/−20 nm, 300-400, 300-2000 nm+/−20 nm, or 400-2000 nm+/−20 nm.

In some embodiments, nanoparticles have a mean particle diameter of 25-30 nm+/−25 nm, 25-35 nm+/−25 nm, 25-40 nm+/−25 nm, 25-45 nm+/−25 nm, 25-250 nm+/−25 nm, 25-255 nm+/−25 nm, 25-60 nm+/−25 nm, 25-70 nm+/−25 nm, 25-75 nm+/−25 nm, 25-80 nm+/−25 nm, 25-90 nm+/−25 nm, 25-95 nm+/−25 nm, 25-100 nm+/−25 nm, 25-125 nm+/−25 nm, 25-150 nm+/−25 nm, 25-200 nm+/−25 nm, 25-300 nm+/−25 nm, 25-400 nm+/−25 nm, 30-35 nm+/−25 nm, 35-40 nm+/−25 nm, 35-45 nm+/−25 nm, 35-250 nm+/−25 nm, 35-255 nm+/−25 nm, 35-60 nm+/−25 nm, 35-70 nm+/−25 nm, 35-75 nm+/−25 nm, 35-80 nm+/−25 nm, 35-90 nm+/−25 nm, 35-95 nm+/−25 nm, 35-100 nm+/−25 nm, 35-125 nm+/−25 nm, 35-150 nm+/−25 nm, 35-200 nm+/−25 nm, 35-300 nm+/−25 nm, 35-400, 35-2500 nm+/−25 nm, 40-45 nm+/−25 nm, 35-250 nm+/−25 nm, 45-255 nm+/−25 nm, 45-60 nm+/−25 nm, 45-70 nm+/−25 nm, 45-75 nm+/−25 nm, 45-80 nm+/−25 nm, 45-90 nm+/−25 nm, 45-95 nm+/−25 nm, 45-100 nm+/−25 nm, 45-125 nm+/−25 nm, 45-150 nm+/−25 nm, 45-200 nm+/−25 nm, 45-300 nm+/−25 nm, 45-400, 45-2500 nm+/−25 nm, 50-255 nm+/−25 nm, 50-60 nm+/−25 nm, 50-70 nm+/−25 nm, 50-75 nm+/−25 nm, 50-80 nm+/−25 nm, 50-90 nm+/−25 nm, 50-95 nm+/−25 nm, 50-100 nm+/−25 nm, 50-125 nm+/−25 nm, 50-150 nm+/−25 nm, 50-200 nm+/−25 nm, 50-300 nm+/−25 nm, 50-400, 50-2500 nm+/−25 nm, 55-60 nm+/−25 nm, 55-70 nm+/−25 nm, 55-75 nm+/−25 nm, 55-80 nm+/−25 nm, 55-90 nm+/−25 nm, 55-95 nm+/−25 nm, 55-100 nm+/−25 nm, 55-125 nm+/−25 nm, 55-150 nm+/−25 nm, 55-200 nm+/−25 nm, 55-300 nm+/−25 nm, 55-400, 55-2500 nm+/−25 nm, 60-70 nm+/−25 nm, 60-75 nm+/−25 nm, 60-80 nm+/−25 nm, 60-90 nm+/−25 nm, 60-95 nm+/−25 nm, 60-100 nm+/−25 nm, 60-125 nm+/−25 nm, 60-150 nm+/−25 nm, 60-200 nm+/−25 nm, 60-300 nm+/−25 nm, 60-400, 60-2500 nm+/−25 nm, 65-70 nm+/−25 nm, 65-75 nm+/−25 nm, 65-80 nm+/−25 nm, 65-90 nm+/−25 nm, 65-95 nm+/−25 nm, 65-100 nm+/−25 nm, 65-125 nm+/−25 nm, 65-150 nm+/−25 nm, 65-200 nm+/−25 nm, 65-300 nm+/−25 nm, 65-400, 65-2500 nm+/−25 nm, 70-75 nm+/−25 nm, 70-80 nm+/−25 nm, 70-90 nm+/−25 nm, 70-95 nm+/−25 nm, 70-100 nm+/−25 nm, 70-125 nm+/−25 nm, 70-150 nm+/−25 nm, 70-200 nm+/−25 nm, 70-300 nm+/−25 nm, 70-400, 70-2500 nm+/−25 nm, 75-80 nm+/−25 nm, 75-90 nm+/−25 nm, 75-95 nm+/−25 nm, 75-100 nm+/−25 nm, 75-125 nm+/−25 nm, 75-150 nm+/−25 nm, 75-200 nm+/−25 nm, 75-300 nm+/−25 nm, 75-400, 75-2500 nm+/−25 nm, 80-90 nm+/−25 nm, 80-95 nm+/−25 nm, 80-100 nm+/−25 nm, 80-125 nm+/−25 nm, 80-150 nm+/−25 nm, 80-200 nm+/−25 nm, 80-300 nm+/−25 nm, 80-400, 80-2500 nm+/−25 nm, 85-90 nm+/−25 nm, 85-95 nm+/−25 nm, 85-100 nm+/−25 nm, 85-125 nm+/−25 nm, 85-150 nm+/−25 nm, 85-200 nm+/−25 nm, 85-300 nm+/−25 nm, 85-400, 85-2500 nm+/−25 nm, 90-95 nm+/−25 nm, 90-100 nm+/−25 nm, 90-125 nm+/−25 nm, 90-150 nm+/−25 nm, 90-200 nm+/−25 nm, 90-300 nm+/−25 nm, 90-400, 90-2500 nm+/−25 nm, 100-125 nm+/−25 nm, 100-150 nm+/−25 nm, 100-200 nm+/−25 nm, 100-300 nm+/−25 nm, 100-400, 100-2500 nm+/−25 nm, 125-150 nm+/−25 nm, 125-200 nm+/−25 nm, 125-300 nm+/−25 nm, 125-400, 125-2500 nm+/−25 nm, 150-200 nm+/−25 nm, 150-300 nm+/−25 nm, 150-400, 150-2500 nm+/−25 nm, 175-200 nm+/−25 nm, 175-300 nm+/−25 nm, 175-400, 175-2500 nm+/−25 nm, 200-300 nm+/−25 nm, 200-400, 200-2500 nm+/−25 nm, 300-400, 300-2500 nm+/−25 nm, or 400-2500 nm+/−25 nm.

In some embodiments, nanoparticles have a mean particle diameter of 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 125, 150, 175, 200, 224, 250, 275, 300, 325, 350, 375, 400, 425, 450, 475, or 500 nm.

In some embodiments, nanoparticles have a mean particle diameter of 50+/−5 nm, 75+/−5 nm, 100+/−5 nm, 125+/−5 nm, 150+/−5 nm, 175+/−5 nm, 200+/−5 nm, 225+/−5 nm, 250+/−5 nm, 275+/−5 nm, 300+/−5 nm, 325+/−5 nm, 350+/−5 nm, 375+/−5 nm, 400+/−5 nm, 425+/−5 nm, 450+/−5 nm, 475+/−5 nm, or 500+/−5 nm.

In some embodiments, nanoparticles have a mean particle diameter of 50+/−10 nm, 75+/−10 nm, 100+/−10 nm, 125+/−10 nm, 150+/−10 nm, 175+/−10 nm, 200+/−10 nm, 225+/−10 nm, 250+/−10 nm, 275+/−10 nm, 300+/−10 nm, 325+/−10 nm, 350+/−10 nm, 375+/−10 nm, 400+/−10 nm, 425+/−10 nm, 450+/−10 nm, 475+/−10 nm, or 500+/−10 nm.

In some embodiments, nanoparticles have a mean particle diameter of 50+/−15 nm, 75+/−15 nm, 100+/−15 nm, 125+/−15 nm, 150+/−15 nm, 175+/−15 nm, 200+/−15 nm, 225+/−15 nm, 250+/−15 nm, 275+/−15 nm, 300+/−15 nm, 325+/−15 nm, 350+/−15 nm, 375+/−15 nm, 400+/−15 nm, 425+/−15 nm, 450+/−15 nm, 475+/−15 nm, or 500+/−15 nm.

In some embodiments, nanoparticles have a mean particle diameter of 50+/−20 nm, 75+/−20 nm, 100+/−20 nm, 125+/−20 nm, 150+/−20 nm, 175+/−20 nm, 200+/−20 nm, 225+/−20 nm, 250+/−20 nm, 275+/−20 nm, 300+/−20 nm, 325+/−20 nm, 350+/−20 nm, 375+/−20 nm, 400+/−20 nm, 425+/−20 nm, 450+/−20 nm, 475+/−20 nm, or 500+/−20 nm.

In some embodiments, nanoparticles have a mean particle diameter of 50+/−25 nm, 75+/−25 nm, 100+/−25 nm, 125+/−25 nm, 150+/−25 nm, 175+/−25 nm, 200+/−25 nm, 225+/−25 nm, 250+/−25 nm, 275+/−25 nm, 300+/−25 nm, 325+/−25 nm, 350+/−25 nm, 375+/−25 nm, 400+/−25 nm, 425+/−25 nm, 450+/−25 nm, 475+/−25 nm, or 500+/−25 nm.

In some embodiments, nanoparticles have a mean particle diameter of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 nm.

Quantum Dots

In some embodiments, the nanoparticle is a quantum dot. Quantum dots are discrete nanoparticles that have properties similar to bulk semiconductors such that when exposed to electromagnetic energy they in turn emit energy. Quantum dots can be engineered to be sensitive to energy in the infrared region, the visible spectrum, and even ultraviolet range through changes in size and composition. Further, they can be designed to be either photoluminescent or photovoltaic, producing either light or energy, respectively.

Colloidal semiconductor quantum dots are typically synthesized from precursor compounds dissolved in solution and is often based on a three component system comprising precursors, organic surfactants, and solvents. In a typical process, on heating a reaction medium to the desired temperature, the precursors chemically transform into monomers. Once the monomers reach a high enough supersaturation level, the quantum dot growth commences via a nucleation process. The temperature during the growth process is one of the factors in determining optimal conditions for the quantum dot growth. Generally, the temperature must be sufficiently high to allow for rearrangement and annealing of the atoms during the synthesis process. However, the temperature should not be too high so as to inhibit crystal growth. An additional factor, which also is often controlled during the quantum dot growth process, is the monomer concentration. The growth process of quantum dot often occurs in two different regimes, those being "focusing" and "defocusing". At high monomer concentrations, the critical size (the size where quantum dots neither grow nor shrink) is very narrow, resulting in growth of nearly all particles. In this regime, the relative rates of growth favor the growth of smaller particles, which provides "focus" and provides a high degree of mono-dispersity with respect to particle size. The size focusing is considered to be optimal when the monomer concentration is kept such that the average quantum dot size present is always slightly larger than the critical size. When the monomer concentration is depleted during growth, the critical size becomes larger than the average size present, and the distribution "defocuses" as a result of a process known as Ostwald ripening.

There are colloidal methods to produce many different semiconductor binary and ternary quantum dots. Examples of quantum dots produced by colloidal methods include, but are not limited to, cadmium-selenide (CdSe), cadmium-sulfide (CdS), indium-arsenide (InAs), and indium-phosphide (InP) cadmium-tellurium-sulfide (CdTeS). The number of atoms that comprise a quantum dot can range from 100 to 100,000, typically with a diameter ranging from 2 to 20 nm (e.g., 2, 3, 4, 5, 6, 7, 8, 9, 10, 11, 12, 13, 14, 15, 16, 17, 18, 19, 20, 2.5, 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 2-3 nm, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20 nm).

In some embodiments, quantum dot materials include, but are not limited to, carbon, colloidal gold, germanium, indium arsenide, indium antimonide, gallium arsenide, gallium nitride, cadmium/selenium/telluride, lead, lead oxide, lead sulfide, lead selenide, indium gallium phosphide, silicon, colloidal silver, mercury cadmium telluride, iron, iron oxide, cobalt, graphene, lanthanum, cerium, strontium carbonate, manganese, manganese oxide, nickel oxide, platinum, lithium, lithium titanate, tantalum, copper, palladium, molybdenum, boron carbide, silicon carbide, titanium carbide, tungsten oxide, aluminum, niobium, thulium, aluminum nitride, tin, aluminum oxide, tin oxide, antimony, dysprosium, paseodynium, antinmony oxide, erbium, rhenium, barium, ruthenium, beryllium, samarium, bismuth oxide, boron, gadolinium, boron nitride, vanadium oxide, strontium, ytterbium, zirconium, diamond (C), Silicon (Si), germanium (Ge), silicon carbide (SiC), silicon-germanium (SiGe), aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), aluminium gallium arsenide (AlGaAs, $Al_xGa_{1-x}As$), indium gallium arsenide (InGaAs, $In_xGa_{1-x}As$), indium gallium phosphide (InGaP), aluminum indium arsenide (AlInAs), aluminum indium antimonide (AlInSb), gallium arsenide nitride (GaAsN), gallium arsenide phosphide (GaAsP), aluminum gallium nitride (AlGaN), aluminum gallium phosphide (AlGaP), indium gallium nitride (InGaN), indium arsenide antimonide (InAsSb), indium gallium antimonide (InGaSb), aluminum gallium indium phosphide (AlGaInP, also InAlGaP, InGaAlP, AlInGaP), aluminum gallium arsenide phosphide (AlGaAsP), indium gallium arsenide phosphide (InGaAsP), aluminum indium arsenide phosphide (AlInAsP), aluminum gallium arsenide nitride (AlGaAsN), indium gallium arsenide nitride (InGaAsN), indium aluminium arsenide nitride (InAlAsN), gallium arsenide antimonide nitride (GaAsSbN), gallium indium nitride arsenide antimonide (GaInNAsSb), gallium indium arsenide antimonide phosphide (GaInAsSbP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cadmium zinc telluride (CdZnTe, "CZT"), mercury cadmium telluride (HgCdTe), mercury zinc telluride (HgZnTe), mercury zinc selenide (HgZnSe), cuprous chloride (CuCl), lead selenide (PbSe), lead sulfide (PbS), lead telluride (PbTe), tin sulfide (SnS), tin telluride (SnTe), lead tin telluride (PbSnTe), thallium tin telluride ($Tl_2SnTe_5$), thallium germanium telluride ($Tl_2GeTe_5$), bismuth telluride ($Bi_2Te_3$), cadmium phosphide ($Cd_3P_2$), cadmium arsenide ($Cd_3As_2$), cadmium antimonide ($Cd_3Sb_2$), zinc phosphide ($Zn_3P_2$), zinc arsenide ($Zn_3As_2$), zinc antimonide ($Zn_3Sb_2$), lead(II) iodide ($PbI_2$), molybdenum disulfide ($MoS_2$), gallium selenide (GaSe), tin sulfide (SnS), bismuth sulfide ($Bi_2S_3$), copper indium gallium selenide (CIGS), platinum silicide (PtSi), bismuth(III) iodide (Bib), mercury(II) iodide ($HgI_2$), thallium(I) bromide (TlBr), titanium dioxide: anatase ($TiO_2$), copper(I) oxide ($Cu_2O$), copper(II) oxide (CuO), uranium dioxide ($UO_2$), uranium trioxide ($UO_3$), and the like.

In some embodiments, suitable materials for quantum dots of the invention include organic semiconductors comprising pentacene, anthracene and rubrene. In some embodiments, suitable materials for quantum dots of the invention include magnetic semiconductors such as manganese-doped indium arsenide and gallium arsenide, manganese-doped indium antimonide, manganese- and iron-doped indium oxide, manganese doped zinc oxide, and chromium doped aluminum nitride, iron-doped tin dioxide, n-type Cobalt-doped zinc oxide, cobalt-doped titanium dioxide (both rutile and anatase), chromium-doped rutile, Iron-doped rutile and iron-doped anatase, nickel-doped anatase, and manganese-doped tin dioxide.

Quantum dots can be formed using a variety of techniques. For example, the quantum dots can be formed by creating a region of a first material having a first band gap surrounded by a second material of a second band gap, wherein the second band gap is larger than the first band gap. Exemplary quantum dots produced by such a process include, but are not limited to, a cadmium selenide (CdSe) core surrounded by a zinc selenide (ZnS) shell.

Alternatively, self-assembled quantum dots nucleate spontaneously under certain conditions during molecular beam epitaxy (MBE) and metallorganic vapor phase epitaxy (MOVPE), when a material is grown on a substrate to which it is not lattice matched. The resulting strain between the grown layer and the substrate produces coherently strained islands on top of a two-dimensional "wetting-layer." The islands can be subsequently surrounded by a shell to form the quantum dot.

Individual quantum dots can also be created from two-dimensional electron or hole gases present in remotely doped quantum wells or semiconductor heterostructures. In this case, a surface is coated with a thin layer of photoresist. A lateral pattern is then defined in the resist by electron beam lithography. This pattern can then be transferred to the electron or hole gas by etching, or by depositing metal electrodes (lift-off process) that allow the application of external voltages between the electron gas and the electrodes.

Quantum dots can also be formed in quantum well structures due to monolayer fluctuations in the well's thickness. Alternatively, quantum dots can be produced by Ultrasonic Aerosol Pyrolysis (UAP).

In some embodiments, quantum dots include an inner semiconductor core formed of, for example, indium/gallium/phosphide, silicon, gallium arsenide, cadmium telluride, copper indium gallium selenide, indium gallium nitride, carbon, colloidal gold, colloidal silver, or organic materials such as polymer-fullerene heterojunctions (e.g., P3HT+C60), organic nanocrystal solar cells (e.g., cadmium selenide or cadmium telluride), dye sensitized cells (e.g., dye and titanium oxide or nobelium oxide), or a tandem cell (e.g., copper-phthalocyanin+C60); a shell, formed of, for example, zinc selenide or other suitable material; a coating, formed of, for example, PEG lipids or other suitable material; and biofunctional material, formed of, for example, biotin, streptavadin, adhesion proteins, vitamins, organic an inorganic compounds, carbohydrates, aptamers, amino acids, lipids, hyaluronic acid, or other suitable proteins.

Antigen Presenting Complexes

Antigen presenting complexes comprise an antigen binding cleft and can bind an antigen for presentation to a T cell or T cell precursor. Antigen presenting complexes can be, for example, MHC class I or class II molecules, fusion proteins comprising functional antigen binding clefts of MHC class I or class II molecules, MHC class I or class II "molecular complexes" (described below), or non-classical MHC-like molecules such as members of the CD1 family (e.g., CD1a, CD1b, CD1c, CD1d, and CD1e).

In some embodiments, the antigen presenting complexes are MHC class I and/or MHC class II molecular complexes. MHC class I and class II molecular complexes have a number of useful features. For example, they are extremely stable and easy to produce, based on the stability and secretion efficiency provided by the immunoglobulin backbone. Further, by altering the Fc portion of the immunoglobulin, different biological functions can be provided to the molecule based on biological functions afforded by the Fc portion. Substitution of the Fc portion of one type of immunoglobulin gene for another is within the skill of the art.

"MHC class I molecular complexes" are described in U.S. Pat. No. 6,268,411. MHC class I molecular complexes are formed in a conformationally intact fashion at the ends of the immunoglobulin heavy chains (see FIG. 1A of U.S. Pat. No. 6,268,411 for a schematic representation). MHC class I molecular complexes to which antigenic peptides are bound can stably bind to antigen-specific lymphocyte receptors (e.g., T cell receptors).

MHC class I molecular complexes comprise at least two fusion proteins. A first fusion protein comprises a first MHC class I α chain and a first immunoglobulin heavy chain, and a second fusion protein comprises a second MHC class I α chain and a second immunoglobulin heavy chain. The first and second immunoglobulin heavy chains associate to form the MHC class I molecular complex, which comprises two MHC class I peptide binding clefts. The immunoglobulin heavy chain can be the heavy chain of an IgM, IgD, IgG1, IgG3, $IgG2_β$, $IgG2_α$, IgE, or IgA. Preferably, an IgG heavy chain is used to form MHC class I molecular complexes. If multivalent MHC class I molecular complexes are desired, IgM or IgA heavy chains can be used to provide pentavalent or tetravalent molecules, respectively. MHC class I molecular complexes with other valencies can also be constructed, using multiple immunoglobulin heavy chains. Construction of MHC class I molecular complexes is described in detail in U.S. Pat. No. 6,268,411.

"MHC class II molecular complexes" are described in U.S. Pat. Nos. 6,458,354, 6,015,884, 6,140,113, and 6,448,071. MHC class II molecular complexes comprise at least four fusion proteins. Two first fusion proteins comprise (i) an immunoglobulin heavy chain and (ii) an extracellular domain of an MHC class IIβ chain. Two second fusion proteins comprise (i) an immunoglobulin κ or λ light chain and (ii) an extracellular domain of an MHC class IIα chain. The two first and the two second fusion proteins associate to form the MHC class II molecular complex. The extracellular domain of the MHC class 1113 chain of each first fusion protein and the extracellular domain of the MHC class IIa chain of each second fusion protein form an MHC class II peptide binding cleft.

The immunoglobulin heavy chain can be the heavy chain of an IgM, IgD, IgG3, IgG1, IgG2$_\beta$, IgG2$_\alpha$, IgE, or IgA. Preferably, an IgG1 heavy chain is used to form divalent molecular complexes comprising two antigen binding clefts. Optionally, a variable region of the heavy chain can be included. IgM or IgA heavy chains can be used to provide pentavalent or tetravalent molecular complexes, respectively. Molecular complexes with other valencies can also be constructed, using multiple immunoglobulin chains.

Fusion proteins of an MHC class II molecular complex can comprise a peptide linker inserted between an immunoglobulin chain and an extracellular domain of an MHC class II polypeptide. The length of the linker sequence can vary, depending upon the flexibility required to regulate the degree of antigen binding and receptor cross-linking. Constructs can also be designed such that the extracellular domains MHC class II polypeptides are directly and covalently attached to the immunoglobulin molecules without an additional linker region.

If a linker region is included, this region will preferably contain at least 3 and not more than 30 amino acids. More preferably, the linker is about 5 and not more than 20 amino acids; most preferably, the linker is less than 10 amino acids. Generally, the linker consists of short glycine/serine spacers, but any amino acid can be used. A preferred linker for connecting an immunoglobulin heavy chain to an extracellular domain of an MHC class II β chain is GLY-GLY-GLY-THR-SER-GLY (SEQ ID NO:1). A preferred linker for connecting an immunoglobulin light chain to an extracellular domain of an MHC class IIa chain is GLY-SER-LEU-GLY-GLY-SER (SEQ ID NO:2).

T Cell Affecting Molecules

"T cell affecting molecules" are molecules that have a biological effect on a precursor T cell or on an antigen-specific T cell. Such biological effects include, for example, differentiation of a precursor T cell into a CTL, helper T cell (e.g., Th1, Th2), or regulatory T cell; proliferation of T cells; and induction of T cell apoptosis. Thus, T cell affecting molecules include T cell costimulatory molecules, adhesion molecules, T cell growth factors, regulatory T cell inducer molecules, and apoptosis-inducing molecules. In some embodiments, a nano-aAPC comprises at least one such molecule; optionally, a nano-aAPC comprises at least two, three, or four such molecules, in any combination.

T cell costimulatory molecules contribute to the activation of antigen-specific T cells. Such molecules include, but are not limited to, molecules that specifically bind to CD28 (including antibodies), CD80 (B7-1), CD86 (B7-2), B7-H3, 4-1BBL, CD27, CD30, CD134 (OX-40L), B7h (B7RP-1), CD40, LIGHT, antibodies that specifically bind to HVEM, antibodies that specifically bind to CD40L, antibodies that specifically bind to OX40, and antibodies that specifically bind to 4-1BB.

Adhesion molecules useful for nano-aAPC can be used to mediate adhesion of the nano-aAPC to a T cell or to a T cell precursor. Useful adhesion molecules include, for example, ICAM-1 and LFA-3.

T cell growth factors affect proliferation and/or differentiation of T cells. Examples of T cell growth factors include cytokines (e.g., interleukins, interferons) and superantigens. If desired, cytokines can be present in molecular complexes comprising fusion proteins. In one embodiment, a cytokine molecular complex can comprise at least two fusion proteins: a first fusion protein comprises a first cytokine and an immunoglobulin heavy chain and a second fusion protein comprises a second cytokine and a second immunoglobulin heavy chain. The first and second immunoglobulin heavy chains associate to form the cytokine molecular complex. In another embodiment, a cytokine molecular complex comprises at least four fusion proteins: two first fusion proteins comprise (i) an immunoglobulin heavy chain and (ii) a first cytokine and two second fusion proteins comprise (i) an immunoglobulin light chain and (ii) a second cytokine. The two first and the two second fusion proteins associate to form the cytokine molecular complex. The first and second cytokines in either type of cytokine molecular complex can be the same or different. Particularly useful cytokines include IL-2, IL-4, IL-7, IL-10, IL-12, IL-15, and gamma interferon.

Superantigens are powerful T cell mitogens. Superantigens stimulate T cell mitogenesis by first binding to class II major histocompatibility (MHC) molecules and then as a binary complex bind in a Vβ-specific manner to the T cell antigen receptor (TCR). Superantigens include, but are not limited to, bacterial enterotoxins, such as staphylococcal enterotoxins (e.g., SEA and active portions thereof, disclosed in U.S. Pat. No. 5,859,207; SEB, SEC, SED and SEE retroviral superantigens (disclosed in U.S. Pat. No. 5,519, 114); *Streptococcus pyogenes* exotoxin (SPE), *Staphylococcus aureus* toxic shock-syndrome toxin (TSST-1), a streptococcal mitogenic exotoxin (SME) and a streptococcal superantigen (SSA) (disclosed in US 2003/0039655); and superantigens disclosed in US 2003/0036644 and US 2003/0009015.

Regulatory T cell inducer molecules are molecules that induce differentiation and/or maintenance of regulatory T cells. Such molecules include, but are not limited to, TGFβ, IL-10, interferon-α, and IL-15. See, e.g., US 2003/0049696, US 2002/0090724, US 2002/0090357, US 2002/0034500, and US 2003/0064067.

Apoptosis-inducing molecules cause cell death. Apoptosis-inducing molecules include toxins (e.g., ricin A chain, mutant *Pseudomonas* exotoxins, diphtheria toxoid, streptonigrin, boamycin, saporin, gelonin, and pokeweed antiviral protein), TNFα, and Fas ligand.

Antigens

A variety of antigens can be bound to antigen presenting complexes. The nature of the antigens depends on the type of antigen presenting complex that is used. For example, peptide antigens can be bound to MHC class I and class II peptide binding clefts. Non-classical MHC-like molecules can be used to present non-peptide antigens such as phospholipids, complex carbohydrates, and the like (e.g., bacterial membrane components such as mycolic acid and lipoarabinomannan). "Antigens" as used herein also includes "antigenic peptides."

Any peptide capable of inducing an immune response can be bound to an antigen presenting complex. Antigenic peptides include tumor-associated antigens, autoantigens, alloantigens, and antigens of infectious agents.

"Tumor-associated antigens" include unique tumor antigens expressed exclusively by the tumor from which they are derived, shared tumor antigens expressed in many tumors but not in normal adult tissues (oncofetal antigens), and tissue-specific antigens expressed also by the normal tissue from which the tumor arose. Tumor-associated antigens can be, for example, embryonic antigens, antigens with abnormal post-translational modifications, differentiation antigens, products of mutated oncogenes or tumor suppressors, fusion proteins, or oncoviral proteins.

A variety of tumor-associated antigens are known in the art, and many of these are commercially available. Oncofetal and embryonic antigens include carcinoembryonic antigen and alpha-fetoprotein (usually only highly expressed in developing embryos but frequently highly expressed by tumors of the liver and colon, respectively), MAGE-1 and MAGE-3 (expressed in melanoma, breast cancer, and glioma), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastric carcinoma), alphafetoprotein receptor (expressed in multiple tumor types, particularly mammary tumors), and M2A (expressed in germ cell neoplasia).

Tumor-associated differentiation antigens include tyrosinase (expressed in melanoma) and particular surface immunoglobulins (expressed in lymphomas).

Mutated oncogene or tumor-suppressor gene products include Ras and p53, both of which are expressed in many tumor types, Her-2/neu (expressed in breast and gynecological cancers), EGF-R, estrogen receptor, progesterone receptor, retinoblastoma gene product, myc (associated with lung cancer), ras, p53, nonmutant associated with breast tumors, MAGE-1, and MAGE-3 (associated with melanoma, lung, and other cancers).

Fusion proteins include BCR-ABL, which is expressed in chromic myeloid leukemia.

Oncoviral proteins include HPV type 16, E6, and E7, which are found in cervical carcinoma.

Tissue-specific antigens include melanotransferrin and MUC1 (expressed in pancreatic and breast cancers); CD10 (previously known as common acute lymphoblastic leukemia antigen, or CALLA) or surface immunoglobulin (expressed in B cell leukemias and lymphomas); the a chain of the IL-2 receptor, T cell receptor, CD45R, CD4$^+$/CD8$^+$ (expressed in T cell leukemias and lymphomas); prostate-specific antigen and prostatic acid-phosphatase (expressed in prostate carcinoma); GP 100, MelanA/Mart-1, tyrosinase, gp75/brown, BAGE, and S-100 (expressed in melanoma); cytokeratins (expressed in various carcinomas); and CD19, CD20, and CD37 (expressed in lymphoma).

Tumor-associated antigens also include altered glycolipid and glycoprotein antigens, such as neuraminic acid-containing glycosphingolipids (e.g., $GM_2$ and $GD_2$, expressed in melanomas and some brain tumors); blood group antigens, particularly T and sialylated Tn antigens, which can be aberrantly expressed in carcinomas; and mucins, such as CA-125 and CA-19-9 (expressed on ovarian carcinomas) or the underglycosylated MUC-1 (expressed on breast and pancreatic carcinomas).

Tissue-specific antigens include epithelial membrane antigen (expressed in multiple epithelial carcinomas), CYFRA 21-1 (expressed in lung cancer), Ep-CAM (expressed in pan-carcinoma), CA125 (expressed in ovarian cancer), intact monoclonal immunoglobulin or light chain fragments (expressed in myeloma), and the beta subunit of An "autoantigen" is an organism's own "self antigen" to which the organism produces an immune response. Autoantigens are involved in autoimmune diseases such as Goodpasture's syndrome, multiple sclerosis, Graves' disease, myasthenia gravis, systemic lupus erythematosus, insulin-dependent diabetes mellitus, rheumatoid arthritis, pemphigus vulgaris, Addison's disease, dermatitis herpetiformis, celiac disease, and Hashimoto's thyroiditis.

Diabetes-related autoantigens include insulin, glutamic acid decarboxylase (GAD) and other islet cell autoantigens, e.g., ICA 512/IA-2 protein tyrosine phosphatase, ICA12, ICA69, preproinsulin or an immunologically active fragment thereof (e.g., insulin B-chain, A chain, C peptide or an immunologically active fragment thereof), HSP60, carboxypeptidase H, peripherin, gangliosides (e.g., GM1-2, GM3) or immunologically active fragments thereof.

Macular degeneration-associated autoantigens include complement pathway molecules and various autoantigens from RPE, choroid, and retina, vitronectin, β crystallin, calreticulin, serotransferrin, keratin, pyruvate carboxylase, C1, and villin 2.

Other autoantigens include nucleosomes (particles containing histones and DNA); ribonucleoprotein (RNP) particles (containing RNA and proteins that mediate specialized functions in the RNP particle), and double stranded DNA. Still other autoantigens include myelin oligodendrocyte glycoprotein (MOG), myelin associated glycoprotein (MAG), myelin/oligodendrocyte basic protein (MOBP), Oligodendrocyte specific protein (Osp), myelin basic protein (MBP), proteolipid apoprotein (PLP), galactose cerebroside (GalC), glycolipids, sphingolipids, phospholipids, gangliosides and other neuronal antigens.

An "alloantigen" is a direct or indirect product of an allele that is detected as an antigen by another member of the same species. Direct products of such alleles include encoded polypeptides; indirect products include polysaccharides and lipids synthesized by allele-encoded enzymes. Alloantigens include major and minor histocompatibility antigens (known as HLA in humans), including class I and class II antigens, blood group antigens such as the ABO, Lewis group, antigens on T and B cells, and monocyte/endothelial cell antigens. HLA specificities include A (e.g. A1-A74, particularly A1, A2, A3, A11, A23, A24, A28, A30, A33), B (e.g., B1-B77, particularly B7, B8, B35, B44, B53, B60, B62), C (e.g., C1-C11), D (e.g., D1-D26), DR (e.g., DR1, DR2, DR3, DR4, DR7, DR8, and DR11), DQ (e.g., DQ1-DQ9), and DP (e.g., DP1-DP6).

"Antigens of infectious agents" include components of protozoa, bacteria, fungi (both unicellular and multicellular), viruses, prions, intracellular parasites, helminths, and other infectious agents that can induce an immune response.

Bacterial antigens include antigens of gram-positive cocci, gram positive bacilli, gram-negative bacteria, anaerobic bacteria, such as organisms of the families Actinomycetaceae, Bacillaceae, Bartonellaceae, Bordetellae, Captophagaceae, Corynebacteriaceae, Enterobacteriaceae, Legionellaceae, Micrococcaceae, Mycobacteriaceae, Nocardiaceae, Pasteurellaceae, Pseudomonadaceae, Spirochaetaceae, Vibrionaceae and organisms of the genera *Acinetobacter, Brucella, Campylobacter, Erysipelothrix, Ewingella, Francisella, Gardnerella, Helicobacter, Levinea, Listeria, Streptobacillus* and *Tropheryma*.

Antigens of protozoan infectious agents include antigens of malarial plasmodia, *Leishmania* species, *Trypanosoma* species and *Schistosoma* species.

Fungal antigens include antigens of *Aspergillus, Blastomyces, Candida, Coccidioides, Cryptococcus, Histoplasma, Paracoccicioides, Sporothrix*, organisms of the order Mucorales, organisms inducing choromycosis and mycetoma and organisms of the genera *Trichophyton, Microsporum, Epidermophyton*, and *Malassezia*.

Antigens of prions include the sialoglycoprotein PrP 27-30 of the prions that cause scrapie, bovine spongiform encephalopathies (BSE), feline spongiform encephalopathies, kuru, Creutzfeldt-Jakob Disease (CJD), Gerstmann-Strassler-Scheinker Disease (GSS), and fatal familial insomnia (FFI).

Intracellular parasites from which antigenic peptides can be obtained include, but are not limited to, Chlamydiaceae, Mycoplasmataceae, Acholeplasmataceae, Rickettsiae, and organisms of the genera *Coxiella* and *Ehrlichia*.

Antigenic peptides can be obtained from helminths, such as nematodes, trematodes, or cestodes.

Viral peptide antigens include, but are not limited to, those of adenovirus, herpes simplex virus, papilloma virus, respiratory syncytial virus, poxviruses, HIV, influenza viruses, and CMV. Particularly useful viral peptide antigens include HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like.

Binding Antigens to Antigen Presenting Complexes

Antigens, including antigenic peptides, can be bound to an antigen binding cleft of an antigen presenting complex either actively or passively, as described in U.S. Pat. No. 6,268,411. Optionally, an antigenic peptide can be covalently bound to a peptide binding cleft.

If desired, a peptide tether can be used to link an antigenic peptide to a peptide binding cleft. For example, crystallographic analyses of multiple class I MHC molecules indicate that the amino terminus of β2M is very close, approximately 20.5 Angstroms away, from the carboxyl terminus of an antigenic peptide resident in the MHC peptide binding cleft. Thus, using a relatively short linker sequence, approximately 13 amino acids in length, one can tether a peptide to the amino terminus of β2M. If the sequence is appropriate, that peptide will bind to the MHC binding groove (see U.S. Pat. No. 6,268,411).

B Cell Affecting Molecules

"B cell affecting molecules" are molecules that have a biological effect on a B cell or a B cell precursor, such as inducing proliferation or antibody formation. Such molecules include CD40 ligand, as well as cytokines and cytokine molecular complexes as described above. Depending on the type of cytokine molecule used, B cells can be encouraged to produce particular types of antibodies. For example, IL-4 induces the production of IgE, whereas IL-5 induces the production of IgA.

Molecular Complexes for Use on Antibody-Inducing Nano-aAPC

Molecular complexes for use on antibody inducing nano-aAPC are complexes that engage B cell surface immunoglobulins or that engage MHC-antigen complexes on the surface of a B cell. Molecular complexes that engage B cell surface immunoglobulins include antigens complexed to the nano-aAPC surface. Molecular complexes that engage MHC-antigen complexes on the surface of a B cell include T cell receptors (TCRs) and TCR molecular complexes. Antibody inducing nano-aAPC can include one or both forms (i.e., B cell surface immunoglobulin engaging or MHC-antigen engaging) of such molecular complexes.

TCRs specific for any particular antigen can be cloned using methods well known in the art. See, e.g., US 2002/0064521. Cloned antigen-specific TCRs can be used as such or can be used to form TCR molecular complexes, described below.

"TCR molecular complexes" are disclosed in U.S. Pat. Nos. 6,458,354, 6,015,884, 6,140,113, and 6,448,071. TCR molecular complexes comprise at least four fusion proteins. Two first fusion proteins comprise (i) an immunoglobulin heavy chain and (ii) an extracellular domain of a TCR α chain. Two second fusion proteins comprise (i) an immunoglobulin κ or λ light chain and (ii) an extracellular domain of TCR β chain. Alternatively, two first fusion proteins comprise (i) an immunoglobulin heavy chain and (ii) an extracellular domain of a TCR γ chain, and two second fusion proteins comprise (i) an immunoglobulin κ or λ light chain and (ii) an extracellular domain of TCR δ chain. The two first and the two second fusion proteins associate to form the TCR molecular complex. The extracellular domain of the TCR chain of each first fusion protein and the extracellular domain of the TCR chain of each second fusion protein form an antigen recognition cleft.

The immunoglobulin heavy chain can be the heavy chain of an IgM, IgD, IgG3, IgG1, IgG2$_\beta$, IgG2$_\alpha$, IgE, or IgA. Preferably, an IgG1 heavy chain is used to form divalent TCR molecular complexes comprising two antigen recognition clefts. Optionally, a variable region of the heavy chain can be included. IgM or IgA heavy chains can be used to provide pentavalent or tetravalent TCR molecular complexes, respectively. TCR molecular complexes with other valencies can also be constructed, using multiple immunoglobulin chains.

Fusion proteins of a TCR molecular complex can comprise a peptide linker inserted between an immunoglobulin chain and an extracellular domain of a TCR polypeptide. The length of the linker sequence can vary, depending upon the flexibility required to regulate the degree of antigen binding and cross-linking. Constructs can also be designed such that the extracellular domains of TCR polypeptides are directly and covalently attached to the immunoglobulin molecules without an additional linker region. If a linker region is included, this region will preferably contain at least 3 and not more than 30 amino acids. More preferably, the linker is about 5 and not more than 20 amino acids; most preferably, the linker is less than 10 amino acids. Generally, the linker consists of short glycine/serine spacers, but any amino acid can be used. A preferred linker for connecting an immunoglobulin heavy chain to an extracellular domain of a TCR α or γ chain is GLY-GLY-GLY-THR-SER-GLY (SEQ ID NO:1). A preferred linker for connecting an immunoglobulin light chain to an extracellular domain of a TCR or δ chain is GLY-SER-LEU-GLY-GLY-SER (SEQ ID NO:2).

Methods of Using Nano-aAPC to Induce and Expand Specific Cell Populations

Induction and expansion of antigen-specific T cells

This disclosure provides methods of inducing the formation and expansion of antigen-specific T cells, including CTLs, helper T cells, and regulatory T cells. These methods involve contacting an isolated preparation comprising a plurality of precursor T cells with nano-aAPC to which antigens are bound to the antigenic binding clefts. Incubation of the preparation with the nano-aAPC induces precursor cells in the population to form antigen-specific T cells that recognize the antigen. Antigen-specific T cells can be obtained by incubating precursor T cells with nano-aAPC, as described below, or can be obtained by conventional methods, e.g., incubation with dendritic cells, or by incubating with other types of artificial antigen presenting cells as are known in the art.

Typically, either the number or the percentage of antigen-specific T cells in the first cell population is greater than the number or percentage of antigen-specific T cells that are formed if precursor T cells are incubated with particles that comprise an antibody that specifically binds to CD3 but do not comprise an antigen presenting complex.

In any of the embodiments disclosed herein in which nano-aAPC are used, any combination of antigen presenting complexes, bound antigens, and T cell affecting molecules can be used. For example, a nano-aAPC can comprise one or more T cell costimulatory molecules (either the same or different), one or more regulatory T cell inducing molecules (either the same or different), one or more adhesion molecules (either the same or different), and/or one or more T cell growth factors (either the same or different). Similarly, a nano-aAPC can comprise one or more antigen presenting complexes, either the same or different, to which any combination of antigens can be bound. In one embodiment, for example, several different melanoma-associated antigens (e.g., any or all of tyrosinase, MAGE-1, MAGE-3, GP-100, Melan A/Mart-1, gp75/brown, BAGE, and S-100) can be bound to antigen presenting complexes on one or more a nano-aAPC.

Precursor T cells can be obtained from the patient or from a suitable donor. The donor need not be an identical twin or even related to the patient. Preferably, however, the donor and the patient share at least one HLA molecule. Precursor T cells can be obtained from a number of sources, including peripheral blood mononuclear cells, bone marrow, lymph node tissue, spleen tissue, and tumors. Alternatively, T cell lines available in the art can be used.

In one embodiment, precursor T cells are obtained from a unit of blood collected from a subject using any number of techniques known to the skilled artisan, such as Ficoll separation. For example, precursor T cells from the circulating blood of an individual can be obtained by apheresis or leukapheresis. The apheresis product typically contains lymphocytes, including T cells and precursor T cells, monocytes, granulocytes, B cells, other nucleated white blood cells, red blood cells, and platelets. Cells collected by apheresis can be washed to remove the plasma fraction and to place the cells in an appropriate buffer or media for subsequent processing steps. Washing steps can be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample can be removed and the cells directly resuspended in a culture medium. If desired, precursor T cells can be isolated from peripheral blood lymphocytes by lysing the red blood cells and depleting the monocytes, for example, by centrifugation through a PERCOLL™ gradient.

Optionally, a cell population comprising antigen-specific T cells can continue to be incubated with either the same nano-aAPC or a second nano-aAPC for a period of time sufficient to form a second cell population comprising an increased number of antigen-specific T cells relative to the number of antigen-specific T cells in the first cell population. Typically, such incubations are carried out for 3-21 days, preferably 7-10 days.

Suitable incubation conditions (culture medium, temperature, etc.) include those used to culture T cells or T cell precursors, as well as those known in the art for inducing formation of antigen-specific T cells using DC or artificial antigen presenting cells. See, e.g., Latouche & Sadelain, Nature Biotechnol. 18, 405-09, April 2000; Levine et al., J. Immunol. 159, 5921-30, 1997; Maus et al., Nature Biotechnol. 20, 143-48, February 2002. See also the specific examples, below.

To assess the magnitude of a proliferative signal, antigen-specific T cell populations can be labeled with CFSE and analyzed for the rate and number of cell divisions. T cells can be labeled with CFSE after one-two rounds of stimulation with nano-aAPC to which an antigen is bound. At that point, antigen-specific T cells should represent 2-10% of the total cell population. The antigen-specific T cells can be detected using antigen-specific staining so that the rate and number of divisions of antigen-specific T cells can be followed by CFSE loss. At varying times (for example, 12, 24, 36, 48, and 72 hours) after stimulation, the cells can be analyzed for both antigen presenting complex staining and CFSE. Stimulation with nano-aAPC to which an antigen has not been bound can be used to determine baseline levels of proliferation. Optionally, proliferation can be detected by monitoring incorporation of $^3$H-thymidine, as is known in the art.

Cultures can stimulated for variable amounts of time (e.g., 0.5, 2, 6, 12, 36 hours as well as continuous stimulation) with nano-aAPC. The effect of stimulation time in highly enriched antigen-specific T cell cultures can be assessed, and conditions can be identified under which a large percentage (e.g., 50, 70, 75, 80, 85, 90, 95, or 98%) of nano-aAPC can be recovered with little cell loss. Antigen-specific T cell can then be placed back in culture and analyzed for cell growth, proliferation rates, effects on apoptosis, various effector functions, and the like, as is known in the art. Such conditions may vary depending on the antigen-specific T cell response desired.

Detection of Antigen-Specific T Cells

The effect of nano-aAPC on expansion, activation and differentiation of T cell precursors can be assayed in any number of ways known to those of skill in the art. A rapid determination of function can be achieved using a proliferation assay, by determining the increase of CTL, helper T cells, or regulatory T cells in a culture by detecting markers specific to each type of T cell. Such markers are known in the art. CTL can be detected by assaying for cytokine production or for cytolytic activity using chromium release assays.

Analysis of Homing Receptors on Nano-aAPC-Induced/Expanded Antigen-Specific T Cells In addition to generating antigen-specific T cells with appropriate effector functions, another parameter for antigen-specific T cell efficacy is expression of homing receptors that allow the T cells to traffic to sites of pathology (Sallusto et al., Nature 401, 708-12, 1999; Lanzavecchia & Sallusto, Science 290, 92-97, 2000). The absence of appropriate homing receptors has been implicated in the setting of chronic CMV and EBV infection (Chen et al., Blood 98, 156-64, 2001). In addition, one difference noted between the use of professional APC and nonprofessional APC to expand antigen-specific T cells is expression of appropriate homing receptors, which may account for the presence of in vivo dysfunctional CTL (Salio et al., J. Immunol. 167, 1188-97, 2001).

For example, effector CTL efficacy has been linked to the following phenotype of homing receptors, CD62L+, CD45RO+, and CCR7−. Thus, a nano-aAPC-induced and/or expanded CTL population can be characterized for expression of these homing receptors. Homing receptor expression is a complex trait linked to initial stimulation conditions. Presumably, this is controlled both by the co-stimulatory complexes as well as cytokine milieu. One important cytokine that has been implicated is IL-12 (Salio et al., 2001). As discussed below, nano-aAPC offer the potential to vary individually separate components (e.g., T cell effector molecules and antigen presenting complexes) to optimize biological outcome parameters. Optionally, cytokines such as IL-12 can be included in the initial induction cultures to affect homing receptor profiles in an antigen-specific T cell population.

Analysis of Off-Rate in Induced and/or Expanded Antigen-Specific T Cell Populations Evolution of secondary immune responses are associated with focusing of the affinities, as determined by analysis of TCR "off-rates" (Savage et al., Immunity 10, 485-92, 1999; Busch et al., *J. Exp. Med.* 188, 61-70, 1998; Busch & Pamer, *J. Exp. Med.* 189, 701-09, 1999). A decrease in TCR-off rates (i.e., resulting in increased TCR affinity) is a parameter that correlates well with increased ability to recognize low amounts of antigen and biological efficacy of a T cell population of interest. Off-rates can be optimized by varying the magnitude and/or duration of nano-aAPC-mediated stimulation.

Separation of Antigen-Specific T Cells from Other Cells

Antigen-specific T cells which are bound to antigens can be separated from cells which are not bound. Any method known in the art can be used to achieve this separation, including magnetic enrichment, plasmapheresis, flow cytometry, or differential centrifugation. In one embodiment T cells are isolated by incubation with beads, for example, anti-CD3/anti-CD28-conjugated beads, such as DYNABEADS® M-450 CD3/CD28 T, for a time period sufficient for positive selection of the desired T cells.

If desired, subpopulations of antigen-specific T cells can be separated from other cells that may be present. For example, specific subpopulations of T cells, such as CD28$^+$, CD4$^+$, CD8$^+$, CD45RA$^+$, and CD45RO$^+$T cells, can be further isolated by positive or negative selection techniques. One method is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11 b, CD16, HLA-DR, and CD8.

Antigen-specific regulatory T cells can be detected and/or separated from other cells using the marker Foxp3. The time period can range from 30 minutes to 36 hours or 10 to 24 hours or can be at least 1, 2, 3, 4, 5, or 6 hours or at least 24 hours. Longer incubation times can be used to isolate T cells in any situation where there are few T cells as compared to other cell types, such in isolating tumor infiltrating lymphocytes (TIL) from tumor tissue or from immunocompromised individuals.

Induction and Expansion of Antibody-Producing B Cells

The disclosure also provides methods of inducing the formation of antibody-producing B cells. These methods involve contacting an isolated preparation comprising a plurality of precursor B cells with antibody inducing nano-aAPC. Incubation of the preparation with the antibody inducing nano-aAPC induces precursor cells in the population to form antibody producing B cells that produce antibodies that specifically recognize the antigen. Typically, either the number or the percentage of antibody-producing B cells in the first cell population is greater than the number or percentage of antibody-producing cells that are formed if precursor B cells are incubated with a non-specific stimulus, e.g., phytohemagglutinin (PHA), lipopolysaccharide (LPS), or pokeweed. In any of the embodiments disclosed herein in which antibody inducing nano-aAPC are used, any combination of B cell affecting molecules and complexes that engage B cell surface immunoglobulins or MHC-antigen complexes on a B cell surface can be used.

Precursor B cells can be obtained from the patient or from a suitable donor. The donor and the patient need not be related, but preferably share at least one HLA molecule. Alternatively, B cell lines available in the art can be used. In one embodiment, precursor B cells are obtained from a unit of blood collected from a subject using any number of techniques known to the skilled artisan, such as Ficoll separation. For example, precursor B cells from the circulating blood of an individual can be obtained by apheresis or leukapheresis, as discussed above.

B cells or their precursors can be cultured using methods known in the art. See, e.g., Schultze et al., *J. Clin. Invest.* 100, 2757-65, 1997; von Bergwelt-Baildon et al., *Blood* 99, 3319-25, 2002. Such conditions also are suitable for incubating B cell precursors with antibody inducing nano-aAPC.

Optionally, a cell population comprising antibody-producing B cells can continue to be incubated with either the same antibody inducing nano-aAPC or a second antibody inducing nano-aAPC for a period of time sufficient to form a second cell population comprising an increased number of antibody-producing B cells relative to the number of antibody-producing B cells in the first cell population. Typically, such incubations are carried out for 3-21 days, preferably 7-10 days.

Optimizing the Duration of Interaction Between Antibody Inducing Nano-aAPC and B Cells As with T cells stimulation discussed above, the duration of stimulation required to induce or expand populations of antibody-producing B cells may differ from that occurring normally, particularly if an artificial, non-biodegradable surface is used for the nano-aAPC. Thus, stimulation by the nano-aAPC could potentially go on for hours if not days. The duration of interaction between various antibody inducing nano-aAPC and precursor or antibody-producing B cells can be determined using methods similar to those discussed above for antigen-specific T cells.

Detection of Antibody-Producing B Cells

The effect of antibody-producing nano-aAPC on expansion, activation and differentiation of B cell precursors can be assayed in any number of ways known to those of skill in the art. A rapid determination of function can be achieved using a proliferation assay, by detecting B cell-specific markers, or by assaying for specific antibody production.

Methods of Using Magnetic Fields and Nano-aAPCs to Induce and Expand Specific T Cell Populations This disclosure provides methods of inducing the formation and expansion of antigen-specific T cells, including CTLs, helper T cells, and regulatory T cells in a magnetic field. Nanoparticle platforms are well-suited to in vivo administration and cellular therapy, as they are less likely than micro-particles to induce tissue infarction or inflammation when co-infused with cells,[37] and iron-dextran nanoparticles, for example, are available in GMP-grade formulations.

Some variations of these methods involve contacting an isolated population of polyclonal T cells with a plurality of nano-aAPC. The nano-aAPCs are paramagnetic and comprise on their surface (1) at least one T cell affecting molecule and (ii) at least one antigen presenting complex. The antigen presenting complex comprises an antigen binding cleft, and the antigen binding cleft comprises an antigen. The isolated population of polyclonal T cells is contacted with the nano-aAPCs in a magnetic field of sufficient strength and for a sufficient time to generate a population of antigen-specific T cells, i.e., T cells specific for the antigen bound to the antigen binding cleft. The population of antigen-specific T cells bound to nano-aAPCs can then be isolated using, e.g., a magnetic enrichment column, flow cytometry or differential centrifugation, and administered to a patient. Methods of isolating cells using magnetic enrichment, followed by infusion, are well known in the art,[38,39] and any of these methods can be used in the practice of the disclosed methods.

Other variations of the disclosed methods involve administering a plurality of nano-aAPCs to a patient and then applying a magnetic field to the patient or to a desired target area of the patient (e.g., a tumor or a localized infection). Use of magnetic fields to direct trafficking of paramagnetic particles and particle-labeled cells in vivo are known in the art[40-42], and any of these methods can be used to direct nano-aAPCs to the desired target area.

Methods of Using Magnetic Fields and Nanoparticles to Preferentially Stimulate Cells in a Particular Physiological State This disclosure provides methods of using nanoparticles, such as magnetic nanoparticles, to target cells in different physiological states (e.g., naive vs previously activated T cells) and stimulate the target cell population. For example, as shown in FIG. 9C and discussed in more detail in the specific examples below, nano-aAPCs providing a dose of 32 ng of MHC stimulates both naive and previously activated T cells between 20- and 30-fold in a week's time. However, at 8 ng or 3.2 ng of MHC, only the activated T cells were stimulated. Thus, a dose of nano-aAPC comprising, for example, 3.2-8 ng of MHC can be used to stimulate previously activated T cells in a T cell population without affecting naive T cells in the population.

The differential effect of nano-aAPC comprising 3.2-8 ng MHC vs 32 ng MHC can be used to separate nano-aAPC binding and isolation of T cells from the activation of the T cells. For example, a population of T cells can be substantially depleted of previously active T cells using, e.g., an antibody to CD44, leaving a population enriched for naive T cells. Binding nano-aAPCs comprising 3.2-8 ng MHC to this population would not activate the naïve T cells, but would permit their purification. The naive T cells comprising the bound nano-aAPCs can then be activated by a variety of techniques known in the art for aggregating nanoparticles. In the case of magnetic nanoparticles, this can be accomplished, for example, by exposing the T cell-nano-aAPC complexes to a magnetic field.

The same approach can be used to separate, characterize and uses as a therapeutic for other cells including by way of example but not limited to, e.g., B cells and stem cells. The optimum ligand density on the surface of a nanoparticle (or, alternatively, the dose of nanoparticles comprising such ligands) which will differentially activate cells of a population in different physiological states can be determined using methods such as those described below in Example 9. Depending on the cell population, the ligand can comprise, e.g., an antibody or a portion of an antibody, a peptide, a nucleotide, a carbohydrate, a lipid, all or portion of a natural ligand for a given receptor (e.g., EGF, PDGF), a chemical (e.g., a chromium salt or a monovalent synthetic ligand that binds immunophilin molecule receptors such as FKBP binding domain), single anti-integrin Fab fragments, RGD peptides, and the like.

Pharmaceutical Preparations

Pharmaceutical preparations comprising nano-aAPC, as well as antigen-specific T cells or antibody-specific B cells obtained using such nano-aAPC, can be formulated for direct injection into patients. Such pharmaceutical preparations contain a pharmaceutically acceptable carrier suitable for delivering the compositions to a patient, such as saline, buffered saline (e.g., phosphate buffered saline), or phosphate buffered saline glucose solution.

Immunotherapeutic Methods

Routes of Administration

Nano-aAPC, as well as antigen-specific T cells or antibody-specific B cells obtained using nano-aAPC, can be administered to patients by any appropriate routes, including intravenous administration, intra-arterial administration, subcutaneous administration, intradermal administration, intralymphatic administration, and intra-tumoral administration. Patients include both human and veterinary patients.

Therapeutic Methods

Nano-aAPC can be used to generate therapeutically useful numbers of antigen-specific T cells or antibody-producing B cells that can be used in diagnostic and therapeutic methods known in the art. See, e.g., WO 01/94944; US 2002/0004041; U.S. Pat. No. 5,583,031; US 2002/0119121; US 2002/0122818; U.S. Pat. No. 5,635,363; US 2002/0090357; U.S. Pat. No. 6,458,354; US 2002/0034500.

In particular, antigen-specific T cells or antibody-producing B cells can be used to treat patients with infectious diseases, cancer, or autoimmune diseases, or to provide prophylactic protection to immunosuppressed patients.

Infectious diseases that can be treated include those caused by bacteria, viruses, prions, fungi, parasites, helminths, etc. Such diseases include AIDS, hepatitis, CMV infection, and post-transplant lymphoproliferative disorder (PTLD). CMV, for example, is the most common viral pathogen found in organ transplant patients and is a major cause of morbidity and mortality in patients undergoing bone marrow or peripheral blood stem cell transplants (Zaia, *Hematol. Oncol. Clin. North Am.* 4, 603-23, 1990). This is due to the immunocompromised status of these patients, which permits reactivation of latent virus in seropositive patients or opportunistic infection in seronegative individuals. Current treatment focuses on the use of antiviral compounds such as gancyclovir, which have drawbacks, the most significant being the development of drug-resistant CMV. A useful alternative to these treatments is a prophylactic immunotherapeutic regimen involving the generation of virus-specific CTL derived from the patient or from an appropriate donor before initiation of the transplant procedure.

PTLD occurs in a significant fraction of transplant patients and results from Epstein-Barr virus (EBV) infection. EBV infection is believed to be present in approximately 90% of the adult population in the United States (Anagnostopoulos & Hummel, *Histopathology* 29, 297-315, 1996). Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers. There is also a strong association between EBV and nasopharyngeal carcinomas. Thus a prophylactic treatment with EBV-specific T cells offers an excellent alternative to current therapies.

Cancers that can be treated include melanoma, carcinomas, e.g., colon, duodenal, prostate, breast, ovarian, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g., neuroblastoma, gliomas, etc.; hematological malignancies, e.g., chronic myelogenous leukemia, childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. See, e.g., Mackensen et al., *Int. J. Cancer* 86, 385-92, 2000; Jonuleit et al., *Int. J. Cancer* 93, 243-51, 2001; Lan et al., *J. Immunotherapy* 24, 66-78, 2001; Meidenbauer et al., *J. Immunol.* 170(4), 2161-69, 2003.

Autoimmune diseases that can be treated include asthma, systemic lupus erythematosus, rheumatoid arthritis, type I diabetes, multiple sclerosis, Crohn's disease, ulcerative colitis, psoriasis, myasthenia gravis, Goodpasture's syndrome, Graves' disease, pemphigus vulgaris, Addison's disease, dermatitis herpetiformis, celiac disease, and Hashimoto's thyroiditis.

Antigen-specific helper T cells can be used to activate macrophages or to activate B cells to produce specific antibodies that can be used, for example, to treat infectious diseases and cancer. Antibody-producing B cells themselves also can be used for this purpose.

Antigen-specific regulatory T cells can be used to achieve an immunosuppressive effect, for example, to treat or prevent graft versus host disease in transplant patients, or to treat or prevent autoimmune diseases, such as those listed above, or allergies. Uses of regulatory T cells are disclosed, for example, in US 2003/0049696, US 2002/0090724, US 2002/0090357, US 2002/0034500, and US 2003/0064067. Nano-aAPC in which the T cell affecting molecule is an apoptosis-inducing molecule can be used to suppress immune responses.

Doses

Antigen-specific T cells can be administered to patients in doses ranging from about $5\text{-}10\times10^6$ CTL/kg of body weight (~$7\times10^8$ CTL/treatment) up to about $3.3\times10^9$ CTL/m$^2$ (~$6\times 10^9$ CTL/treatment) (Walter et al., *New England Journal of Medicine* 333, 1038-44, 1995; Yee et al., *J Exp Med* 192, 1637-44, 2000). In other embodiments, patients can receive $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, or $10^{10}$ cells per dose administered intravenously. In still other embodiments, patients can receive intranodal injections of, e.g., $8\times10^6$ or $12\times10^6$ cells in a 200 µl bolus. Doses of nano-aAPC include $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, or $10^{10}$ nano-aAPC per dose.

Animal Models

A number of murine models are available to assess adoptive immunotherapy protocols for tumor treatment. Two models are particularly suitable for assessing melanoma treatment. One model uses human/SCID mice bearing a subcutaneous implanted human melanoma line, such as BML. In such models, transfer of ex vivo expanded Mart-1-specific CTL delays the onset and/or growth of the tumor. A second model uses the murine A2-transgenic mice and the murine B16 melanoma that has been transfected with an HLA-A2-like molecule, called AAD. This molecule, which is also the basis of the A2-transgenic, is human HLA-A2 in alpha 1-2 domains fused to the murine alpha3 domain. Using these transgenic mice, the murine B16-AAD melanoma is sensitive to rejection across well-defined A2-restricted melanoma epitopes derived from tyrosinase and gp100.

Kits

Nano-aAPC can be provided in kits. Suitable containers for nano-aAPC include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). Optionally, one or more different antigens can be bound to the nano-aAPC or can be supplied separately.

A kit can further comprise a second container comprising a pharmaceutically-acceptable buffer, such as phosphate-buffered saline, Ringer's solution, or dextrose solution. It can also contain other materials useful to an end user, including other buffers, diluents, filters, needles, and syringes. A kit can also comprise a second or third container with another active agent, for example a chemotherapeutic agent or an anti-infective agent, or containing particular antigens that can be bound to antigen presenting complexes of a nano-aAPC by an end user.

Kits also can contain reagents for assessing the extent and efficacy of antigen-specific T cell or antibody-producing B cell induction or expansion, such as antibodies against specific marker proteins, MHC class I or class II molecular complexes, TCR molecular complexes, anticlonotypic antibodies, and the like.

A kit can also comprise a package insert containing written instructions for methods of inducing antigen-specific T cells, expanding antigen-specific T cells, using nano-aAPC in the kit in various treatment protocols. The package insert can be an unapproved draft package insert or can be a package insert approved by the Food and Drug Administration (FDA) or other regulatory body.

Those skilled in the art will appreciate that there are numerous variations and permutations of the above described embodiments that fall within the scope of the appended claims.

EXAMPLE 1

Materials and Methods for Examples 2-7

Mice and reagents. 2C TCR Rag$^{-/-}$ transgenic mice were maintained as heterozygotes by breeding on a C57/BL6 background. pMEL TCR/Thy1$^a$ Rag$^{-/-}$ transgenic mice were a gift from Nicholas Restifo (National Institutes of Health, Bethesda, MD) and maintained as homozygotes. C57BL/6j mice were purchased from Jackson Laboratories (Bar Harbor, ME). All mice were maintained according to Johns Hopkins University's Institutional Review Board. Fluorescently labeled monoclonal antibodies were purchased from BioLegend (San Diego, CA).

Preparation of MHC-Ig Dimers. Soluble MHC-Ig dimers, K$^b$-Ig and D$^b$-Ig, were prepared and loaded with peptide as described (48). Briefly, K$^b$-Ig molecules were loaded with peptide by stripping at alkaline condition (pH 11.5), and then refolded in the presence of 50 fold excess peptide. D$^b$-Ig molecules were stripped under mildly acidic conditions (pH 6.5) and refolded in the presence of 50 fold molar excess peptide and 2-fold molar excess of human β$_2$-microglobulin. Human A2-Ig was passively loaded in the presence of excess M1 peptide (49). Peptides "SIY" (SIYRYYGL, SEQ ID NO:3; synthetic), "SIIN" (SIINFEKL, SEQ ID NO:4;

derived from ovalbumin protein), "GP100" (KVPRNquantum dotWL, SEQ ID NO:5; from melanocyte GP100 protein) "ASN" (ASNENMETH, SEQ ID NO:6; from Influenza A nucleoprotein), and "M1" (GILGFVFTL, SEQ ID NO: 7, from Influenza A M1 protein) were purchased from Genscript (Piscataway, NJ). Protein concentration was determined after labeling by size exclusion High Performance Liquid Chromatography.

Particle Manufacture and Characterization. Nanoscale iron-dextran aAPC were manufactured in one of two ways. 2 μM biotinylated MHC-Ig dimer and an equimolar concentration of biotinylated anti-CD28 antibody were incubated with 100 μL of anti-biotin Miltenyi Microparticles (Miltenyi Biotec) for at least 1 hour with gentle agitation at 4° C. Unbound protein was washed using a MS magnetic enrichment column (Miltenyi Biotec). Particle concentration was measured by absorbance at 405 nm using a Beckman Coulter AD340 plate reader.

Alternatively, MHC-Ig dimer and B7.1-Ig were directly chemically coupled to biodegradable particles (Miltenyi Biotec). Total protein content was assessed by Bradford Assay. Unless otherwise stated, "iron-dextran aAPC" refers to particles directly chemically coupled to MHC and B7.1, rather than anti-biotin coupling.

Nanoscale quantum dot aAPC were manufactured by incubating 5 μM biotinylated MHC-Ig dimer and an equimolar concentration of biotinylated anti-CD28 antibody with 100 μL of 1 μM streptavidin coated quantum dots (Life Technologies) for 2 hours at at 4° C. Quantum dots were washed and concentrated using a Sartorius Vivaspin Membrane with a 300,000 molecular weight cutoff. Quantum dot concentration was measured by absorbance at 405 nm using a Beckman Coulter AD340 plate reader.

Nanoparticle Tracking Analysis. A Nanosight™ LM10 equipped with a sensitive CCD camera was used for characterizing iron-oxide aAPC by NTA. 50 μL of diluted nanoparticle solution was loaded into the sample chamber, which was connected to a 405 nm laser source. A 60 s movie containing the Brownian motion tracking of the scattering centroids (particles) was recorded using NTA software (Version 2.0). The movie was processed using the manufacturer recommended auto settings with manual adjustment of the gain, blur and brightness as recommended. The nanoparticle solution was diluted in phosphate buffered saline to adjust the sample concentration to $5 \times 10^{12}$ particles $mL^{-1}$.

In Vitro Cell Expansion. For mouse cell culture, cells were obtained from homogenized mouse spleens followed by depletion of RBC by hypotonic lysis. Cytotoxic lymphocytes were isolated using a CD8 no-touch isolation kit and magnetic enrichment column from Miltenyi Biotec (Cologne, Germany) and if necessary labeled with carboxyfluorescein succinimidyl ester (CFSE) for 15 minutes at 37° C., then washed extensively. One million CD8+ T cells and particles at the indicated dosages were mixed and cultured in 96 well round bottom plates for 4-7 days in complete RPMI media supplemented with T cell factor, a cytokine cocktail harvested from human plasma(5). CFSE fluorescence was measured on Day 4 using a BD FacsCalibur flow cytometer and analyzed in FlowJo™ (TreeStar).

For human cell culture, PBMCs from healthy HLA*0201 positive donors were isolated by Ficoll-Paque PLUS gradient centrifugation following the manufacturer's protocol (GE Healthcare). CD8+ T cells were further purified from fresh PBMC using the CD8+ T cell negative selection kit (Miltenyi Biotec). The purity of CD8+ T cells was higher than 95%, as determined by flow cytometry. Three million CD8+ T cells and particles at the indicated dosages were mixed and cultured in 96-well round bottom plates for up to 14 days in complete RPMI media supplemented with T cell factor. On day 7 after stimulation, T cells were harvested, counted and replated at the same T cell:nano-aAPC density. Antigen specificity was determined using HLA-M1-specific, A*0201 PE or APC tetramers (Beckman Coulter) according to manufacturer's protocol.

Intracellular Cytokine Staining. Seven days after primary stimulation, T cell functional activity was assessed by re-challenge with peptide-pulsed C57Bl/6j splenocytes. Splenocytes were pulsed with the indicated concentration of peptide for 2 hours at 37° C., then washed. 200,000 T cells were incubated in complete RPMI with 200,000 splenocytes for 4 hours in a round bottom 96 well plate in the presence of 0.2 μl GolgiPlug, 0.2 uL GolgiStop, and anti-CD107a-fitC (BD Biosciences, Mountain View, CA). Cells were washed and fixed using a BD Cytofix/Cytoperm kit (BD Biosciences) according to the manufacturer's instructions, then stained with anti-IFNγ PE (BioLegend). Cytokine staining was assessed by flow cytometry and frequency of cytokine functional cells was assessed by comparison with an unstimulated control in FlowJo™.

Effect of Nano-aAPC on Subcutaneous Tumor Growth In Vivo. For quantum dot aAPC experiment, $2 \times 10^6$ naive CD8+ pMEL T cells were adoptively transferred into 8 week old C57BL/6 male mice by tail vein injection, except for control mice which received no T cells or aAPC treatment. The same day, B16 melanoma cells ($2 \times 10^5$) were injected subcutaneously into the right flank. The following day, mice were treated with either 20 μL cognate quantum dot aAPC, 20 μL non-cognate quantum dot aAPC, or 20 μL PBS, with 5 mice per group. Mice were treated days 3, 4, and 5 with 30,000 units intraperitoneal IL-2. Tumor growth was monitored at 2 day intervals, using digital calipers, until tumor size was ~200 mm² at which point animals were euthanized.

For iron-dextran aAPC experiment, $2 \times 10^6$ naive CD8+ pMEL T cells were adoptively transferred as before. Four days later, mice in the treatment group received 25 μL, cognate HD nano-aAPC either iv or sc, with eight mice per group. Three days later, aAPC were injected either subcutaneously (sc) or intravenously (iv). B16 melanoma cells ($2 \times 10^5$) were injected subcutaneously four days later, and a second injection of aAPC were given four days after tumor, either iv or sc on the ipsilateral flank. Tumor tracking and animal euthanasia proceeded as above.

EXAMPLE 2

Iron-Dextran Nano-aAPC Induce T Cell Expansion

Nanosized iron-oxide core, dextran coated particles produced by the Miltenyi Corporation were selected as a nanoscale particle platform due to their extensive characterization and biocompatibility(21-23). To produce nanoscale aAPC, soluble dimeric MHC-Ig loaded with an appropriate peptide (Signal 1) and chimeric B7.1-Ig fusion protein (Signal 2) were covalently coupled in a 1:1 ratio to the particle surface (FIG. 1A). Alternatively, particles were manufactured by coupling biotinylated MHC-Ig and anti-CD28 to an anti-biotin coated iron-dextran particle (FIG. 1B).

Iron-dextran aAPC were confirmed to be monodisperse and 50-100 nm in diameter using Nanoparticle Tracking Analysis (NTA, FIG. 1C). Particles were suspended at a concentration of 8.3 nM (equivalent to $5 \times 10^{12}$ particles $mL^{-1}$), and all subsequent volumes refer to particles at this concentration. By titrating the amount of protein present during the coupling reaction, we synthesized particles presenting a high density (HD, 65 ug protein/mL of particles) or low density (LD, 16 ug protein/mL of particles) of protein as measured by Bradford Assay.

Figure 2B:
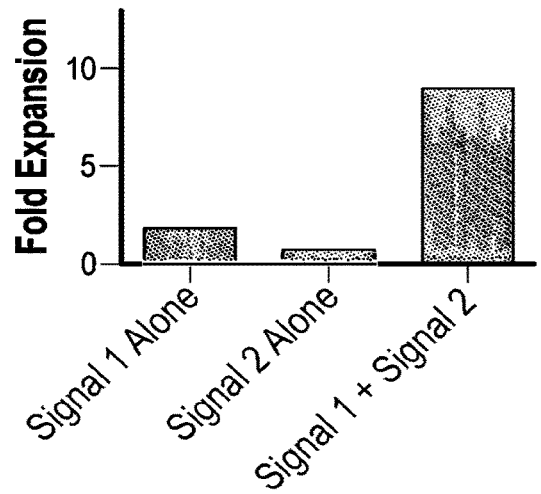

To evaluate aAPC-induced T cell expansion, we utilized two TCR transgenic mouse models: 2C mice, which carry receptors recognizing the SIY peptide presented in the context of MHC Class I H2-$K^b$, and pMEL mice, which recognize a peptide derived from melanoma differentiation antigen GP100 presented in the context of MHC Class I H2-$D^b$. Four types of anti-biotin coupled iron-dextran particles were manufactured, presenting either $K^b$ or $D^b$ loaded with either the cognate peptide described above or a non-cognate peptide (SIIN for $K^b$, ASN for $D^b$). T cells were incubated with particles and proliferation was evaluated seven days later. Particle based expansion was antigen-specific, as 2C cells only proliferated in the presence of $K^b$-SIY particles, and pMEL cells only proliferated in the presence of $D^b$-GP100 particles (FIG. 2A). Furthermore, both Signal 1 and Signal 2 were required for optimal expansion, and anti-biotin particles carrying either MHC-Ig or CD28 alone were not as effective at inducing robust T cell proliferation (FIG. 2B).

Both the amount (24, 25) and density (26, 27) of antigen presented by APC influence downstream T cell behavior such as proliferation and cell death, and may thus be important parameters for aAPC stimulation. HD and LD particles were used to evaluate the effect of antigen density on T cell expansion, and both sets of particles were titrated to evaluate the effect of antigen dose. Proliferation was specifically characterized three days after stimulation using the vital dye carboxyfluorescein succinimidyl ester (CFSE). CFSE is diluted with each round of T cell division, and division thus manifests as a one half-fold decrease in CFSE fluorescence. Seven days after stimulation, T cells were counted to characterize the overall balance between proliferation and death.

Figure 2C:
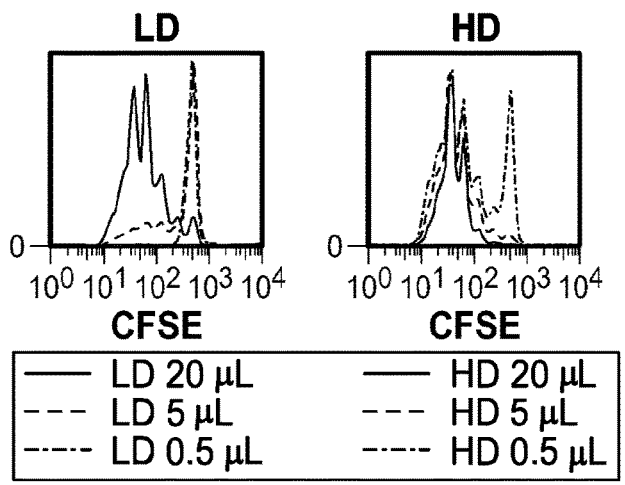
Figure 2D:
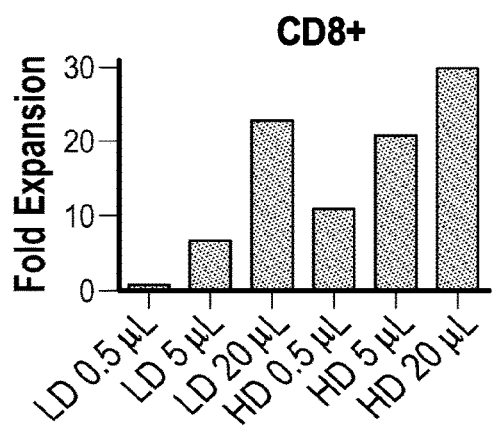

Both HD and LD particles were able to induce pMEL T cell proliferation in a dose-dependent fashion (FIG. 2C). As measured by CFSE dilution, HD particles induced proliferation in 79%, 98%, and 99% of cells for 1, 5, and 20 μLs of particles, respectively, per 1 million cells, while identical amounts of LD particles induced proliferation in 4%, 40%, and 93% of cells. By day 7, HD and LD particles had induced an overall expansion of T cells on the order of 5-30 fold, with a minimum threshold of approximately 5 μL of LD particles and less than 0.5 μL of HD particles required to induce expansion (FIG. 2D). Both CFSE proliferation and cell counts demonstrated that at any given quantity of particles, HD nano-aAPC induced greater expansion than LD. For example, at 5 μL of particles, HD particles induced 21-fold expansion, while LD particles induced only 7-fold expansion.

Figure 2E:
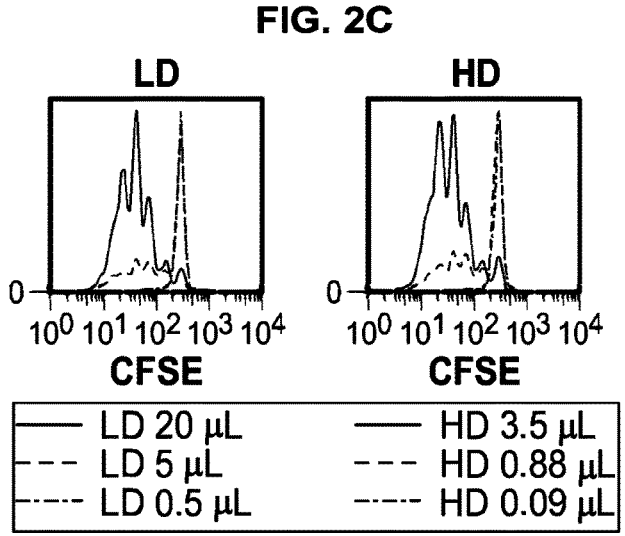
Figure 2F:
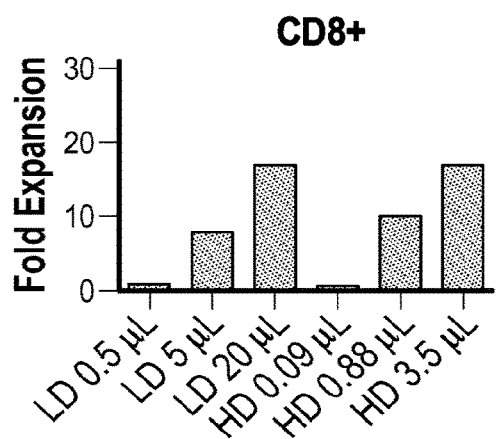

To assess whether the increased amount of protein on HD particles fully accounted for the proliferation advantage, LD and HD particles were incubated with T cells at equal protein concentrations (that is, approximately 5-fold more LD particles at a given concentration of HD). Once aAPC were normalized for protein concentration, HD and LD particles induced similar expansion as measured by CFSE dilution on Day 3 (FIG. 2E) or overall expansion on Day 7 (FIG. 2F). For example, 20 uL of LD particles or 3.5 uL of HD particles both induced proliferation in 94% of cells by Day 3, and approximately 17-fold expansion after 7 days of growth. Thus, at the antigen doses and densities evaluated, expansion was driven by total protein presented on aAPC, and not particle dose or protein density.

EXAMPLE 3

Nano-aAPC Induce a Robust T Cell Effector Phenotype

Generating sufficient numbers of antigenic-specific T cells is a critical goal of immunotherapy. However, CTL can become anergic or even suppressive under certain stimulation conditions(28), so expanded lymphocytes must also be evaluated for their ability to produce critical effector cytokines, such as IFNγ, and to secrete cytotoxic granules, as indicated by surface expression of the degranulation marker CD107a. To assess CTL function after nano-aAPC induced stimulation, whole CD8+ CTL were stimulated with three different particle concentrations: 3.5 uL of HD and 20 uL of LD particles, which present equivalent amounts of protein and thus induce equivalent approximately 10-fold expansion, and 20 uL of HD particles, which induce approximately 17-fold proliferation (FIG. 3A). Seven days after particle-based stimulation, CTL were harvested and re-challenged with peptide-pulsed splenocytes, and assessed for functional response by intracellular cytokine assay.

Functional responses were robust and equivalent for all three particle doses. CTL of all groups expressed high levels of CD107a, with up to 90% of cells degranulating when re-challenged with a high dose of peptide (FIG. 3B). Similarly, all three groups displayed high levels of IFNγ responsiveness (FIG. 3C). Thus, while particle to T cell ratio and protein density on particles influence the degree of CTL expansion, the resulting T cells display a similar, strong effector phenotype regardless of particle dose.

Effector phenotype was also assessed by measuring CD44 and CD62L expression. After activation, T cells upregulate CD44. A subset of cells, which retain high CD62L expression, are termed "Central Memory" T cells ($T_{cm}$) and have high proliferative capacity. The remaining cells, which downregulate CD62L, are termed "Effector Memory" ($T_{em}$), traffic to tissues, and are primed for robust effector responses but have less capacity for proliferation upon re-challenge. These T cell phenotypes have been validated for memory development in vivo, but in vitro activated cells show similar phenotypes and may serve as a model for in vivo memory formation. A representative staining pattern for a nano-aAPC stimulated T cell culture is shown in FIG. 3E. Both HD and LD particles induced robust CD44 upregulation (FIG. 3F). Lower doses of particles generated a higher proportion of CD62Llo CD44hi $T_{em}$ cells, with 2 uL of LD and 2 uL of HD generating 51% and 36% $T_{em}$, respectively. Proportion of Tem cells decreased in a dose-dependent fashion, but all cultures examined contained naive, $T_{cm}$, and $T_{em}$ cells.

EXAMPLE 4

Nano-aAPC Expansion of Endogenous Human T Cell Responses

Antigen-specific precursors T cells exist as low-frequency, heterogenous populations of peripheral blood mononuclear cells (PBMC). Thus immunotherapy ultimately depends on the expansion of antigen-reactive CTL from a polyclonal pool of endogenous precursors.

Anti-biotin iron-dextran aAPC were synthesized bearing the human HLA allele A2 loaded with the immunodominant T cell epitope derived from influenza protein M1 (Signal 1) and anti-CD28 (Signal 2). PBMC were incubated with increasing doses of nano-aAPC and antigen-specific T cell expansion was assessed by tetramer staining after two consecutive stimulations (FIG. 4).

Figure 4A:
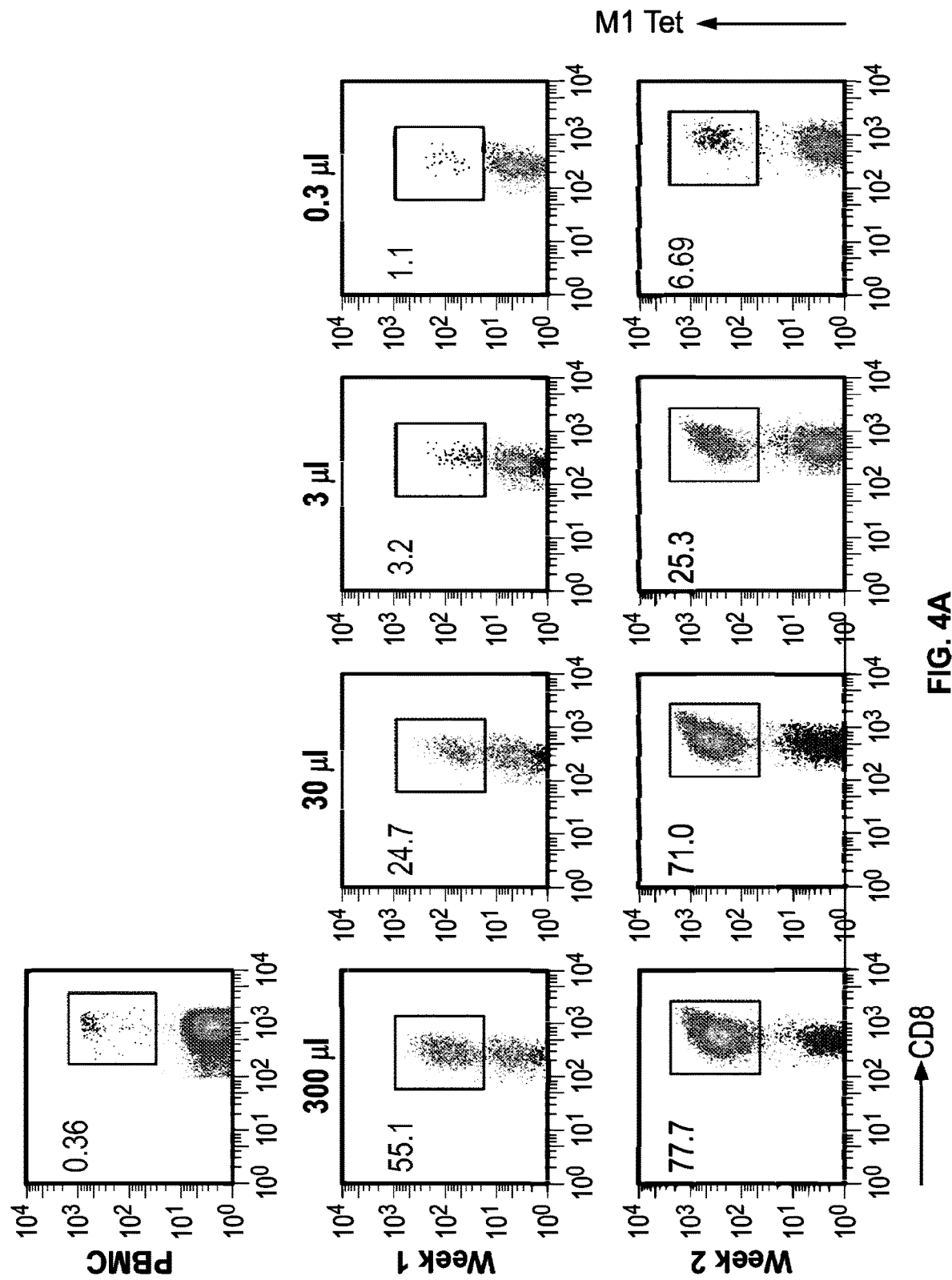
FIGS. 4A-B. Antigen-specific Human T cell Expansion From Endogenous Precursors.
Figure 4B:
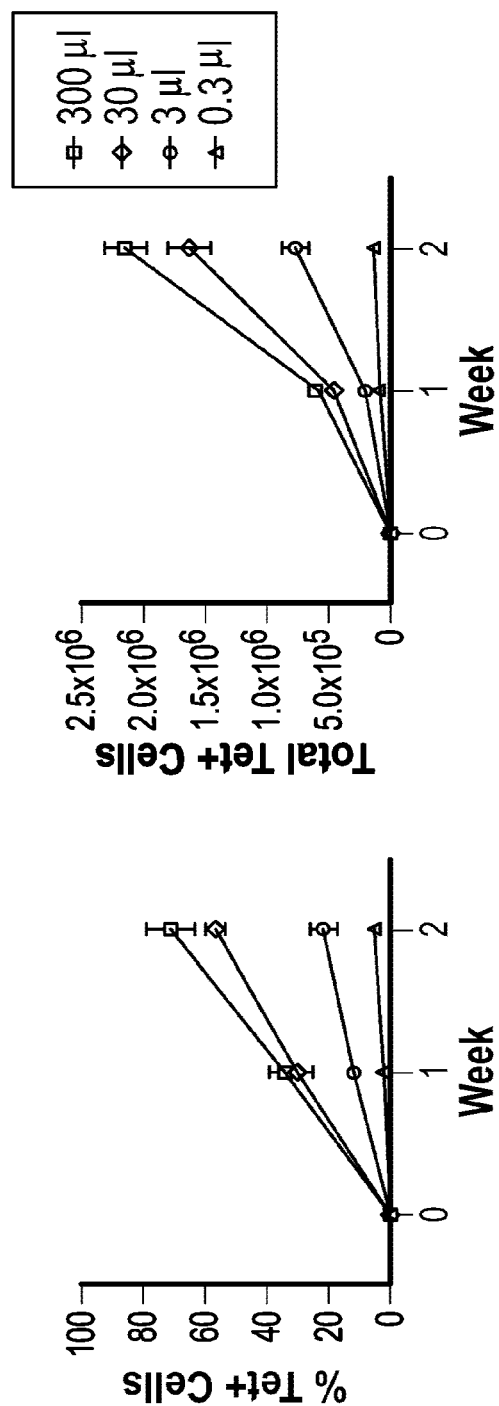

Before stimulation, M1 specific precursor frequency in the peripheral blood was low, with 0.4% specific CD8+ PBMC (FIG. 4A, top row). Incubation with nano-aAPC for one (middle row) or two (bottom row) weeks resulted in a dose-dependent increase in the percentage of antigen specific T cells. These data are summarized in FIG. 4B. The highest dose (300 uL) of nano-aAPC induced up to 44% of antigen specific T cells after one week or 80% after two weeks (left panel). This was associated with a dose-dependent increase in the total amount of antigen-specific T cells (right panel), with up to 150-fold expansion after one week and 800-fold expansion after two weeks at the highest particle dose. Nano-aAPC thus induced large populations of antigen-specific T cells from small endogenous precursor populations.

EXAMPLE 5

Quantum Dot Nano-aAPC

To evaluate nano-aAPC based stimulation at an even smaller scale, and to demonstrate that nano-aAPC are not platform-exclusive, we obtained commercially available quantum dot core, avidin coated nanocrystals less than 20 nm in diameter from Life Technologies. Biotin labeled dimeric $D_b$-GP100 (Signal 1) and anti-CD28 antibody (Signal 2) were bound in a 1:1 molar ratio to the nanocrystal surface to form a Quantum Dot (quantum dot) nano-aAPC (FIG. 5A).

quantum dot aAPC induced dose-dependent, antigen specific T cell expansion in vitro (FIG. 5B). At the highest dose evaluated, T cells expanded 14.6 fold after 7 days, while T cells stimulated with non-cognate control quantum dot aAPC did not expand.

EXAMPLE 6

Nano-aAPC Prime Tumor Rejection In Vivo

Figures 6A, 6B:
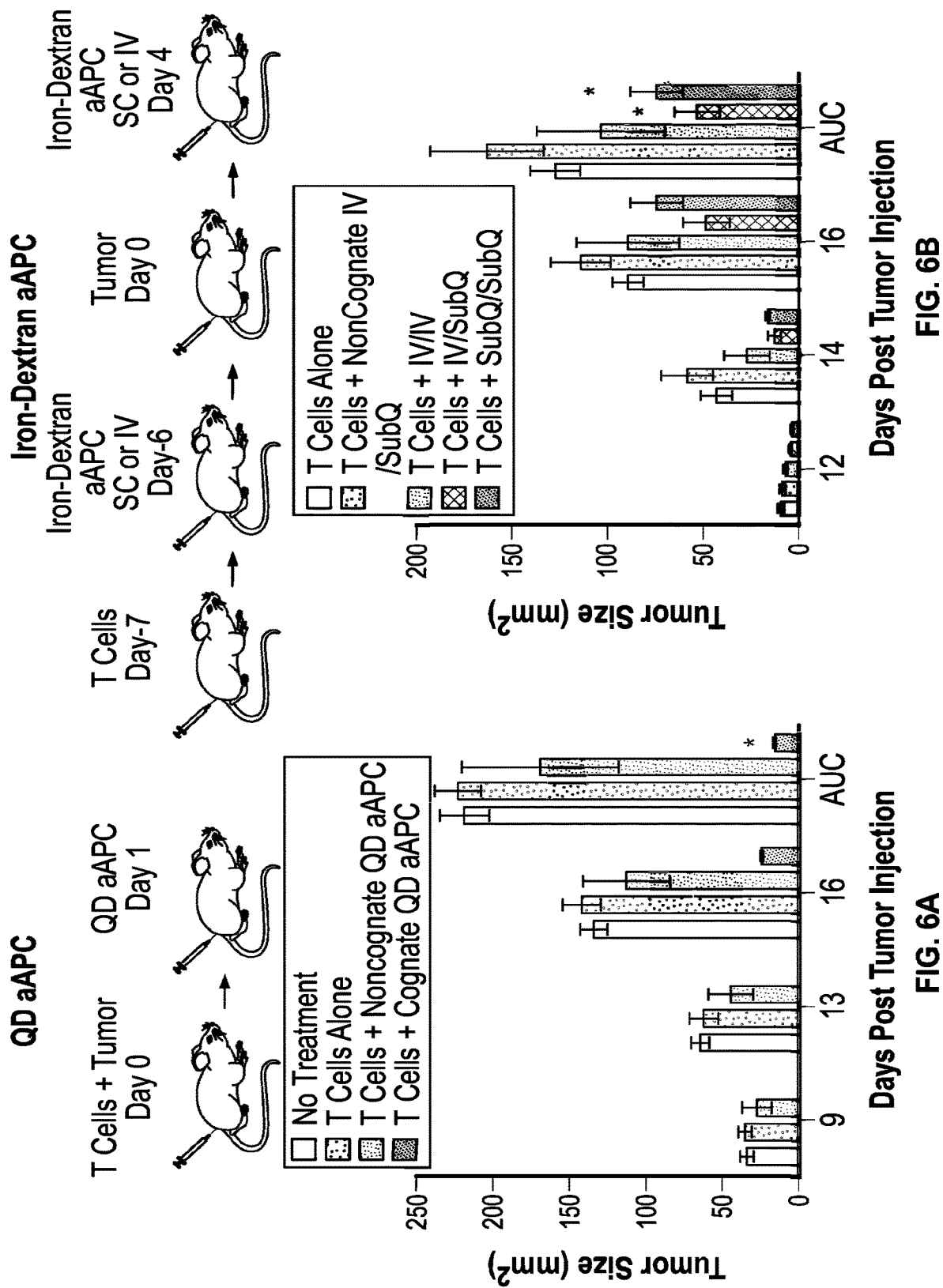
FIGS. 6A-B. Nano-aAPC Mediate Tumor Rejection In Vivo.

A subcutaneous mouse model of melanoma was chosen to demonstrate the efficacy of nanoscale aAPC for immunotherapy when injected directly in vivo. To evaluate quantum dot-aAPC, naive TCR transgenic pMEL CTL were adoptively transferred into wild type B6 mice, and mice were challenged the same day with B16 melanoma cells injected subcutaneously on the right flank (FIG. 6A, top). The following day, mice were injected with either 20 uL of cognate quantum dot aAPC or 20 uL of non-cognate quantum dot aAPC or PBS as control. A single injection of quantum dot aAPC significantly attenuated tumor growth (FIG. 6A, bottom). After 16 days, mice treated with T cells and cognate quantum dot aAPC had the smallest tumor burden, with an average tumor size of 22.1 mm$^2$ 2.3, compared to 111.1 mm$^2$+/−29.4 for T cell+noncognate aAPC treated mice, 141.1 mm 2+/−9.6 for T cells alone, and 133.1 mm$^2$+/−7.6 for untreated mice. Total tumor growth over the course of the experiment was summarized as Area Under the Curve (AUC). Mice treated with cognate quantum dot-aAPC had significantly less (p=0.028) overall tumor growth by AUC (33.1 mm$^2$+/−7.8) than mice treated with control, non-cognate aAPC (373.6 mm 2+/−227.0).

As described previously, the ability of nano-aAPC to traffic to the tumor or T cell pools in lymph nodes may be an important advantage of nano-aAPC immunotherapy. The route of particle administration is likely to affect bead trafficking; for example, subcutaneously deposited beads may drain via lymphatics to lymph nodes (30). To test the impact of route of aAPC administration as well as the in vivo efficacy of iron-dextran aAPC, particles were injected either intravenously or subcutaneously three days after pMEL adoptive transfer. B16 Tumors were injected subcutaneously on right flank four days later, and a second injection of aAPC was given four days after tumor, either iv or sc on ipsilateral flank. Thus, there were three treatment groups: mice receiving two iv bead injections, mice receiving one iv and one sc injection, and mice receiving two sc injections (FIG. 6B, top). Control mice injected with non-cognate aAPC received one iv and one sc injection.

All three treatment groups had less tumor growth than mice injected with control bead (FIG. 6B, bottom). After 16 days, mice treated with one sc and one iv injection (sc/iv) showed the least tumor growth (48.0 mm$^2$+/−31.16), followed by sc/sc treated (73.7 mm$^2$+/−37.44), iv/iv treated (89.4 mm$^2$+/−69.5), no treat (88.4 mm$^2$+/−17.8) and non-cognate treated (113 mm$^2$+/−39.4). Over the entire course of the experiment, sc/iv treated mice (AUC 52.6 mm$^2$+/−29.7) and sc/sc mice (AUC 73.1 mm$^2$+/−36.1) showed significantly less (p<0.02) tumor growth than control mice (AUC 162.7 mm$^2$+/−77.6). Mice treated with two IV injections had less tumor (AUC 103.0+/−86.1) than control, but did not reach the significance threshold (p=0.19). Thus, mice treated with at least one dose of nano-aAPC delivered subcutaneously had significantly less tumor than control.

EXAMPLE 7

Stimulation of Naïve T Cells

Figure 7B:
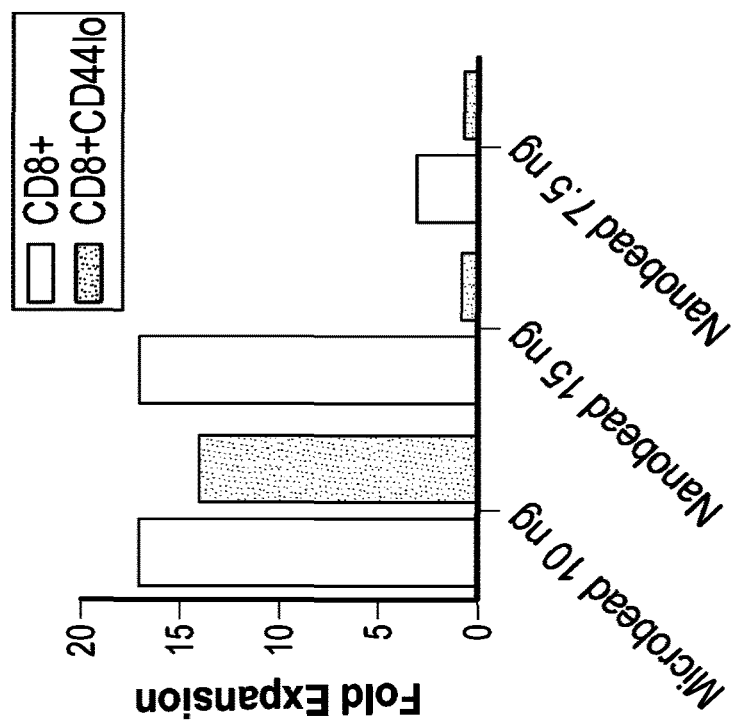
FIG. 7B. When micro- and nano-aAPC are titrated to doses that induce equivalent fold expansion (about 17-fold) in CD8+ (activated) cells, nano-aAPC cannot expand naive T cells.
Figure 7A:
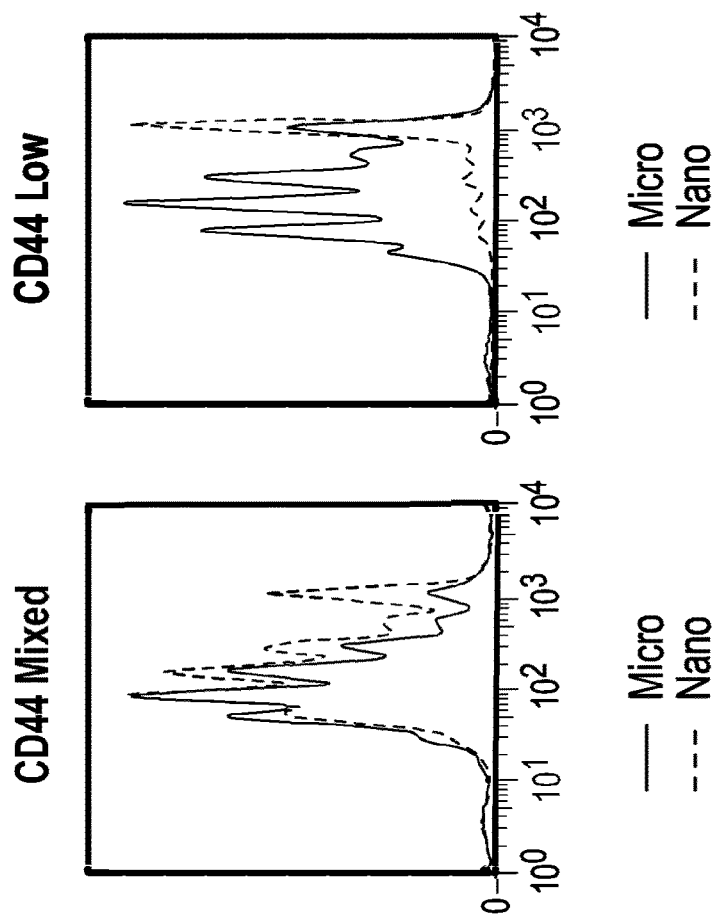
FIG. 7A. CFSE, a dye whose intensity is reduced after T cell proliferation, shows that T cell populations including activated cells (CD44 mixed) proliferate in response to 6 ng of micro- or nano-aAPC based stimulation, but naive CD44 low cells do not.

Using a biophysical MHC-Ig off-rate assay, nano-aAPC disassociate more readily from naive compared to active T cells, suggesting that nano-aAPC make fewer contacts (8-10) with naive cells than with activated cells (16-20). Because induced TCR clustering (Lillemeier et al., *Nature Immunology* 11, 90-96, 2010 and membrane reorganization (James et al., *Nature* 487, 64-69, 2012) are thought to drive T cell activation, it is therefore not surprising that nano-aAPC are less effective at stimulating naive T cells than micro-aAPC. At an equivalent dose of 6 ng MHC-Ig per 100,000 T cells, nano-aAPC stimulate mixed populations of naive and memory cells, not naive cells alone, whereas micro-aAPC can stimulate both populations equivalently (FIG. 7A). Nano-aAPC are able to induce naive T cell activation if the dose of nano-particles is increased six fold (data not shown). When the dose of nano- and micro-aAPC were titrated to induce equivalent 17-fold expansion in activated cells, micro- but not nano-aAPC induced expansion of naive cells at that dose (FIG. 7B).

Optimal T cell immunotherapy, however, may require the activation of naive T cells to avoid immune exhaustion (Besser, *Clinical Cancer Research* 16, 2646-55, 2010). We therefore used two approaches to enhance nano-aAPC mediated activation of naive cells. We first hypothesized that enrichment of antigen-specific precursors would increase the amount of immune-stimulatory cytokines such as IL-7 and IL-15 available to activated T cells, boosting aAPC mediated activation. Nano-aAPC, which are paramagnetic, were bound to wild type T cells at 4° C., then enriched using positive selection on a magnetic column (FIG. 8A). This led to expansion of an Kb-TRP2 specific T cell population seven days after activation (FIG. 8B). We believe this is the first description of an aAPC that can simultaneously enrich and activate T cells.

Secondly, we explored the use of magnet-induced bead clustering to enhance TCR clustering and trigger activation. At low doses of nano-aAPC that did not trigger expansion of naive T cells, T cell activation in a magnetic field conferred a significant proliferation advantage to PMEL T cells (FIG. 8C). Magnet-enhanced activation required at least 30 minutes of incubation in a magnetic field (data not shown), and was effective with both neodynium disk magnets and a magnetic enrichment column sold by Miltenyi Biotec. This suggests a novel method for enhancing T cell activation, and suggests the nano-aAPC can be used to not only activate T cells directly through TCR-MHC interactions, but also by controlling nano-aAPC via magnets. This relies on TCR-particle interactions at this scale, and is not feasible with larger aAPC. Importantly, the nano-aAPC must provide Signal 1, Signal 2, and a paramagnetic core for magnetic boosting, making this a unique and novel reagent for the expansion of previously naive T cells for adoptive immunotherapy.

REFERENCES

1. Zhang, N., and M. J. Bevan. 2011. CD8(+) T cells: foot soldiers of the immune system. Immunity. 35: 161-8.
2. Ahlers, J. D., and I. M. Belyakov. 2010. Memories that last forever: strategies for optimizing vaccine T-cell memory. Blood. 115: 1678-89.
3. Dudley, M. E., J. C. Yang, R. Sherry, M. S. Hughes, R. Royal, et al. 2008. Adoptive cell therapy for patients with metastatic melanoma: evaluation of intensive myeloablative chemoradiation preparative regimens. Journal of clinical oncology: official journal of the American Society of Clinical Oncology. 26: 5233-9.
4. Wrzesinski, C., C. M. Paulos, A. Kaiser, P. Muranski, D. C. Palmer, et al. 2010. Increased intensity lymphodepletion enhances tumor treatment efficacy of adoptively transferred tumor-specific T cells. Journal of Immunotherapy. 33: 1-7.
5. Durai, M., C. Krueger, Z. Ye, L. Cheng, A. Mackensen, et al. 2009. In vivo functional efficacy of tumor-specific T cells expanded using HLA-Ig based artificial antigen presenting cells (aAPC). Cancer immunology, immunotherapy: CII. 58: 209-20.
6. Oelke, M., and J. P. Schneck. 2010. Overview of a HLA-Ig based "Lego-like system" for T cell monitoring, modulation and expansion. Immunologic Research. 47: 248-56.
7. Smith-Garvin, J. E., G. a Koretzky, and M. S. Jordan. 2009. T cell activation. Annual review of immunology. 27: 591-619.
8. Manolova, V., A. Flace, M. Bauer, K. Schwarz, P. Saudan, et al. 2008. Nanoparticles target distinct dendritic cell populations according to their size. European Journal of Immunology. 38: 1404-13.
9. Fifis, T., A. Gamvrellis, B. Crimeen-Irwin, G. a Pietersz, J. Li, et al. 2004. Size-dependent immunogenicity: therapeutic and protective properties of nano-vaccines against tumors. Journal of Immunology. 173: 3148-54.
10. Champion, J. a, A. Walker, and S. Mitragotri. 2008. Role of particle size in phagocytosis of polymeric microspheres. Pharmaceutical research. 25: 1815-21.
11. Sharma, G., D. T. Valenta, Y. Altman, S. Harvey, H. Xie, et al. 2010. Polymer particle shape independently influences binding and internalization by macrophages. Journal of Controlled Release. 147: 408-412.
12. Astete, C. E., and C. M. Sabliov. 2006. Synthesis and characterization of PLGA nanoparticles. Journal of biomaterials science. Polymer edition. 17: 247-89.
13. Florence, A. T. 2004. Issues in oral nanoparticle drug carrier uptake and targeting. J. Drug Target. 12: 65-70.
14. Hubbell, J. a, S. N. Thomas, and M. a Swartz. 2009. Materials engineering for immunomodulation. Nature. 462: 449-60.
15. Anikeeva, N., T. Lebedeva, A. R. Clapp, E. R. Goldman, M. L. Dustin, et al. 2006. Quantum dot/peptide-MHC biosensors reveal strong CD8-dependent cooperation between self and viral antigens that augment the T cell response. Proceedings of the National Academy of Sciences of the United States of America. 103: 16846-51.
16. Mescher, M. F. 1992. Surface contact requirements for activation of cytotoxic T lymphocytes. Journal of Immunology. 149: 2402-5.
17. Steenblock, E. R., S. H. Wrzesinski, R. a Flavell, and T. M. Fahmy. 2009. Antigen presentation on artificial acellular substrates: modular systems for flexible, adaptable immunotherapy. Expert opinion on biological therapy. 9: 451-64.
18. Steenblock, E. R., and T. M. Fahmy. 2008. A comprehensive platform for ex vivo T-cell expansion based on biodegradable polymeric artificial antigen-presenting cells. Molecular therapy: the journal of the American Society of Gene Therapy. 16: 765-72.
19. Dal Porto, J., T. E. Johansen, B. Catipović, D. J. Parfiit, D. Tuveson, et al. 1993. A soluble divalent class I major histocompatibility complex molecule inhibits alloreactive T cells at nanomolar concentrations. Proceedings of the National Academy of Sciences of the United States of America. 90: 6671-5.
20. Lebowitz, M. S., S. M. O'Herrin, a R. Hamad, T. Fahmy, D. Marguet, et al. 1999. Soluble, high-affinity dimers of T-cell receptors and class II major histocompatibility complexes: biochemical probes for analysis and modulation of immune responses. Cellular Immunology. 192: 175-84.
21. Kunzmann, A., B. Andersson, T. Thurnherr, H. Krug, A. Scheynius, et al. 2010. Toxicology of engineered nanomaterials: Focus on biocompatibility, biodistribution and biodegradation. Biochimica et biophysica acta. 1810: 361-373.
22. Dobrovolskaia, M. a, and S. E. McNeil. 2007. Immunological properties of engineered nanomaterials. Nature nanotechnology. 2: 469-78.
23. Nune, S. K., P. Gunda, B. K. Majeti, P. K. Thallapally, and M. L. Forrest. 2011. Advances in lymphatic imaging and drug delivery. Advanced drug delivery reviews.
24. Hosken, N., K. Shibuya, A. Heath, and K M. 1995. The effect of antigen dose on CD4+ T helper cell phenotype development in a T cell receptor-alpha beta-transgenic model. The Journal of. 182: 20-22.
25. Alexander-Miller, M. a, G. R. Leggatt, A. Sarin, and J. a Berzofsky. 1996. Role of antigen, CD8, and cytotoxic T lymphocyte (CTL) avidity in high dose antigen induction of apoptosis of effector CTL. The Journal of experimental medicine. 184: 485-92.
26. Gonzalez, P. a, L. J. Carrefio, D. Coombs, J. E. Mora, E. Palmieri, et al. 2005. T cell receptor binding kinetics required for T cell activation depend on the density of cognate ligand on the antigen-presenting cell. Proceedings of the National Academy of Sciences of the United States of America. 102: 4824-9.
27. Bullock, T. N. J., D. W. Mullins, and V. H. Engelhard. 2003. Antigen density presented by dendritic cells in vivo differentially affects the number and avidity of primary, memory, and recall CD8+ T cells. Journal of Immunology. 170: 1822-9.
28. Mescher, M. F., F. E. Popescu, M. Gerner, C. D. Hammerback, and J. M. Curtsinger. 2007. Activation- 29. Newell, E. W., L. O. Klein, W. Yu, and M. M. Davis. 2009. Simultaneous detection of many T-cell specificities using combinatorial tetramer staining. 6.
30. Cai, S., Q. Yang, T. R. Bagby, and M. L. Forrest. 2011. Lymphatic drug delivery using engineered liposomes and solid lipid nanoparticles. Advanced drug delivery reviews. 63: 901-08.
31. Dustin, M. L. 2008. T-cell activation through immunological synapses and kinapses. Immunol. Rev. 221: 77-89.
32. Chang, J. T., V. R. Palanivel, I. Kinjyo, F. Schambach, A. M. Intlekofer, et al. 2007. Asymmetric T lymphocyte division in the initiation of adaptive immune responses. Science. 315: 1687-91.
33. Varma, R., G. Campi, T. Yokosuka, T. Saito, and M. L. Dustin. 2006. T cell receptor-proximal signals are sustained in peripheral microclusters and terminated in the central supramolecular activation cluster. Immunity. 25: 117-127.
34. Lillemeier, B. F., M. a Mortelmaier, M. B. Forstner, J. B. Huppa, J. T. Groves, et al. 2010. TCR and Lat are expressed on separate protein islands on T cell membranes and concatenate during activation. Nature Immunology. 11: 90-6.
35. Nel, A. E., L. Mädler, D. Velegol, T. Xia, E. M. V. Hoek, et al. 2009. Understanding biophysicochemical interactions at the nano-bio interface. Nature materials. 8: 543-57.
36. Fahmy, T. M., J. G. Bieler, M. Edidin, and J. P. Schneck. 2001. Increased TCR avidity after T cell activation: a mechanism for sensing low-density antigen. Immunity. 14: 135-43.
37. Kumar, R., M. Ferez, M. Swamy, I. Arechaga, M. T. Rejas, et al. 2011. Increased Sensitivity of Antigen-Experienced T cells through the Enrichment of Oligomeric T cell Receptor Complexes. Immunity. 35: 375-87.
38. Hillaireau, H., and P. Couvreur. 2009. Nanocarriers' entry into the cell: relevance to drug delivery. Cellular and Molecular 1Life Sciences. 66: 2873-96.
39. Kocbek, P., N. Obermajer, M. Cegnar, J. Kos, and J. Kristl. 2007. Targeting cancer cells using PLGA nanoparticles surface modified with monoclonal antibody. Journal of Controlled Release. 120: 18-26.
40. Martinez-Martin, N., E. Fernandez-Arenas, S. Cemerski, P. Delgado, M. Turner, et al. 2011. T cell receptor internalization from the immunological synapse is mediated by TC21 and RhoG GTPase-dependent phagocytosis. Immunity. 35: 208-22.
41. He, C., Y. Hu, L. Yin, C. Tang, and C. Yin. 2010. Effects of particle size and surface charge on cellular uptake and biodistribution of polymeric nanoparticles. Biomaterials. 31: 3657-66.
42. Chithrani, B. D., A. a Ghazani, and W. C. W. Chan. 2006. Determining the size and shape dependence of gold nanoparticle uptake into mammalian cells. Nano letters. 6: 662-8.
43. Chithrani, B. D., and W. C. W. Chan. 2007. Elucidating the mechanism of cellular uptake and removal of protein-coated gold nanoparticles of different sizes and shapes. Nano letters. 7: 1542-50.
44. Cho, E. C., L. Au, Q. Zhang, and Y. Xia. 2010. The effects of size, shape, and surface functional group of gold nanostructures on their adsorption and internalization by cells. Small (Weinheim an der Bergstrasse, Germany). 6: 517-22.
45. Maeda, H. 2001. The enhanced permeability and retention (EPR) effect in tumor vasculature: the key role of tumor-selective macromolecular drug targeting. Advances in enzyme regulation. 41: 189-207.
46. Greish, K. 2007. Enhanced permeability and retention of macromolecular drugs in solid tumors: a royal gate for targeted anticancer nanomedicines. Journal of drug targeting. 15: 457-64.
47. Rabinovich, G. a, D. Gabrilovich, and E. M. Sotomayor. 2007. Immunosuppressive strategies that are mediated by tumor cells. Annual review of immunology. 25: 267-96.
48. J. P. Schneck, J. E. Slansky, S. M. O'Herrin, T. F. Greten, Monitoring antigen-specific T cells using MHC-Ig dimers., Current protocols in immunology/edited by John E. Coligan . . . [et al.] Chapter 17, Unit 17.2 (2001).
49. Y.-L. Chiu, J. P. Schneck, M. Oelke, HLA-Ig based artificial antigen presenting cells for efficient ex vivo expansion of human CTL., Journal of visualized experiments: JoVE, 1-5 (2011).

EXAMPLE 8. MATERIALS AND METHODS FOR EXAMPLES 9-13

Mice and reagents. 2C TCR transgenic mice were maintained as heterozygotes by breeding on a C57/BL6 background. Pmel TCR/Thy1$^a$ Rag-/- transgenic mice were a gift from Nicholas Restifo (National Institutes of Health, Bethesda, MD) and maintained as homozygotes. C57BL/6j mice were purchased from Jackson Laboratories (Bar Harbor, ME). All mice were maintained according to Johns Hopkins University's Institutional Review Board. Fluorescently labeled monoclonal antibodies were purchased from BioLegend (San Diego, CA).

Preparation of MHC-Ig Dimers and Nano-aAPC. Soluble MHC-Ig dimers, $K^b$-Ig and $D^b$-Ig, were prepared and loaded with peptides as described,[8] see supplementary methods. Nano-aAPC were manufactured by direct conjugation of MHC-Ig dimer and anti-CD28 antibody (37.51; BioLegend) to MACS Microbeads (Miltenyi Biotec) as described.[3] Protein bound to nanoparticles was measured by fluorescence as described in supplementary methods.

In Vitro Cell Expansion. Cells were obtained from homogenized mouse spleens and lymph nodes followed by hypotonic lysis of RBC. Cytotoxic lymphocytes were isolated using a CD8 no-touch isolation kit and magnetic enrichment column from Miltenyi Biotec (Cologne, Germany). CD44-biotin antibody was added to primary cocktail to isolate CD44lo, naive cells. Where applicable, cells were labeled with carboxyfluorescein succinimidyl ester (CFSE) for 15 minutes at 37° C., then washed extensively.

CD8+ T cells and nano-aAPC, at the indicated dosages, were mixed and cultured in 24 well flat-bottom or 96 well round bottom plates for 4-7 days in complete RPMI media supplemented with T cell factor (TF), a cytokine enriched cocktail of conditioned media harvested from stimulated human PBMC. 46 Where indicated, culture plates were fixed between two Neodynium N52 disk magnets between ¼ and ¾ inches in length (K&J Magnetics, Jamison, PA). CFSE fluorescence was measured at indicated timepoints using a BD FacsCalibur flow cytometer and analyzed in FlowJo™ (TreeStar). Fold expansion was assessed by cell counts seven days after stimulation. Expansion of endogenous antigen-specific cells was assessed by staining with 400 nM fluorescently labeled MHC-Ig dimer seven days after activation.

Particle Binding Assays. For equilibrium particle binding assays, CD8$^+$ T cells were incubated at 4° C. at a concentration of $10^7$ cells/ml in FACS wash buffer (PBS+2% FCS+0.05% sodium azide). 30 µl aliquots of cells were mixed with varying concentrations of nanoparticles bearing fluorescently labeled MHC-Ig dimer for 60-90 min. After washing, cell-bound fluorescence was measured by flow cytometer and MCF (mean channel fluorescence) was calculated using FlowJo™.

For particle off-rate binding assays, cells and a saturating dose of nanoparticle or soluble MHC-Ig dimer were bound to steady-state as described above. MCF was measured at Time 0, followed by the addition of excess clonotypic 1B2 blocking antibody to prevent re-binding. MCF was measured at the indicated timepoints, and effective off-rate was calculated for exponential decay in GraphPad Prism (La Jolla, CA). Cell-particle contacts were estimated as described in Table 2.

Microscopy. T cells were bound to nano-aAPC for 60 minutes at 4° C. Cells were subsequently transferred to a 96-well plate at 37° C. in the presence or absence of a magnetic field generated by Neodymium N52 disk magnets. After 30 minutes, cells were washed and stained at 4° C. with Alexa488 anti-LFA1, monoclonal PE anti-mouse IgG1, and Alexa 647 anti-CD3ε. Samples were washed and fixed immediately with 2% paraformaldehyde. Images were acquired on a Zeiss LSM 510 META (Zeiss, Oberkochen, Germany) laser scanning confocal at 100× magnification at the Johns Hopkins School of Medicine Microscopy Facility. CD3ε cluster size was determined using a particle-detection algorithm written in ImageJ (National Institutes of Health) using the built-in Particle Analyzer.

Preparation of MHC-Ig Dimers. Soluble MHC-Ig dimers, $K^b$-Ig and $D^b$-Ig, were prepared and loaded with peptide as described (Schneck, J. P.; Slansky, J. E.; O'Herrin, S. M.; Greten, T. F. Monitoring Antigen-Specific T Cells Using MHC-Ig Dimers. Curr. Protoc. Immunol. 2001, Chapter 17, Unit 17.2). Briefly, $K^b$-Ig molecules were loaded with peptide by stripping at alkaline condition (pH 11.5), and then refolded in the presence of 50 fold excess peptide. $D^b$-Ig molecules were stripped under mildly acidic conditions (pH 6.5) and refolded in the presence of 50 fold molar excess peptide and 2-fold molar excess of human $\beta_2$-microglobulin (Chiu, Y.-L.; Schneck, J. P.; Oelke, M. HLA-Ig Based Artificial Antigen Presenting Cells for Efficient Ex Vivo Expansion of Human CTL. J. Vis. Exp. 2011, 1-5). Peptides SIY (SIYRYYGL, synthetic; SEQ ID NO:3), SIIN (SIINFEKL, derived from ovalbumin protein; SEQ ID NO:4), GP100 (KVPRNQDWL, from melanocyte GP100 protein; SEQ ID NO:5) and ASN (ASNENMETH, from influenza A nucleoprotein; SEQ ID NO: 6) were purchased from Genscript (Piscataway, NJ). Protein concentration was determined after labeling by size exclusion high performance liquid chromatography (HPLC).

Micro-aAPC Synthesis. Micro-aAPCs were fabricated as described previously (Oelke, M.; Schneck, J. P. Overview of a HLA-Ig Based "Lego-Like System" for T Cell Monitoring, Modulation and Expansion. Immunol. Res. 2010, 47, 248-56) by direct chemical coupling of protein to 4.5 µm Dynal™ Magnetic Microbeads (Life Technologies, Carlsbad, CA). For the initial coupling step, 25 µg anti-biotin antibody (Sigma, St. Louis, MO) was added to 100 million microbeads in 0.1 M sodium borate buffer. After washing in a magnetic column, biotin labeled MHC-Ig and CD28 were added in equimolar amounts to form aAPC.

Nanoparticle Tracking Analysis. A Nanosight™ LM 10 equipped with a sensitive CCD camera was used for characterizing the size distribution of nano-aAPC by NTA. 50 µL of diluted nanoparticle solution was loaded into the sample chamber, which was connected to a 405 nm laser source. A 60 s movie containing the Brownian motion tracking of the scattering centroids (particles) was recorded using NTA software (Version 2.0). The movie was processed using the manufacturer recommended auto settings with manual adjustment of the gain, blur and brightness as recommended. The nanoparticle solution was diluted in phosphate buffered saline to adjust the sample concentration to $5 \times 10^{12}$ particles $mL^{-1}$.

Micro-aAPC Microscopy. T cells were incubated with micro-aAPC, spun at 1000 RPM for 1 minute to pack cells and particles, and incubated for 60 minutes at 4° C. Cells were subsequently transferred to a 96-well plate at 37° C. in the presence or absence of a magnetic field generated by Neodymium N52 disk magnets. After 30 minutes, cells were washed and stained at 4° C. with Alexa488 anti-LFA1, monoclonal PE anti-mouse IgG1, and Alexa 647 anti-CD3ε. Samples were washed and fixed immediately with 2% paraformaldehyde. Images were acquired on a Zeiss LSM 510 META (Zeiss, Oberkochen, Germany) laser scanning confocal at 100× magnification at the Johns Hopkins School of Medicine Microscopy Facility. CD3ε cluster size was determined using a particle-detection algorithm written in ImageJ (National Institutes of Health) using the built-in Particle Analyzer. Particle auto-fluorescense for cells bound to particles was removed manually.

Effect of Nano-aAPC on In Vivo T cell Expansion and Inhibition of Subcutaneous Tumor Growth. CD44lo, CD8+ cells were isolated from pmel spleen and lymph nodes using a magnetic enrichment column and activated for 24 hours in the presence or absence of a magnetic field as described above. $1 \times 10^6$ Thy1.1+ pmel cells were adoptively transferred into B6 Thy1.2+ wild type hosts (n=6 mice per group). Mice were treated both the day of and the day after adoptive transfer with 30,000 units intraperitoneal IL-2. Seven and twenty-days after adoptive transfer, three mice per group were sacrificed and lymphocytes were isolated from peripheral blood, spleen, and inguinal, cervical, and axillary lymph nodes, and then stained with anti-Thy1.1 antibody.

Tumor rejection experiments were performed as above, except $3 \times 10^5$ B16 melanoma cells were injected subcutaneously ten days prior to T cell adoptive transfer. Transient lymphopenia was induced by sublethal irradiation (500 cGy) one day before adoptive transfer with a MSD Nordion Gammacell dual Cs137 source (Johns Hopkins Molecular Imaging Center) as irradiation induced lymphopenia is thought to remove immunosuppressive host cells and reduce competition for lymphotrophic cytokines, 35 and significantly enhances the effect of immunotherapy for melanoma in clinical trials.[36] Tumor growth was monitored at 2 day intervals using digital calipers, until tumor size was ~150 $mm^2$, at which point animals were euthanized.

EXAMPLE 9. NANO-AAPC PREFERENTIALLY STIMULATE ACTIVATED T CELLS

Figures 13A, 13B:
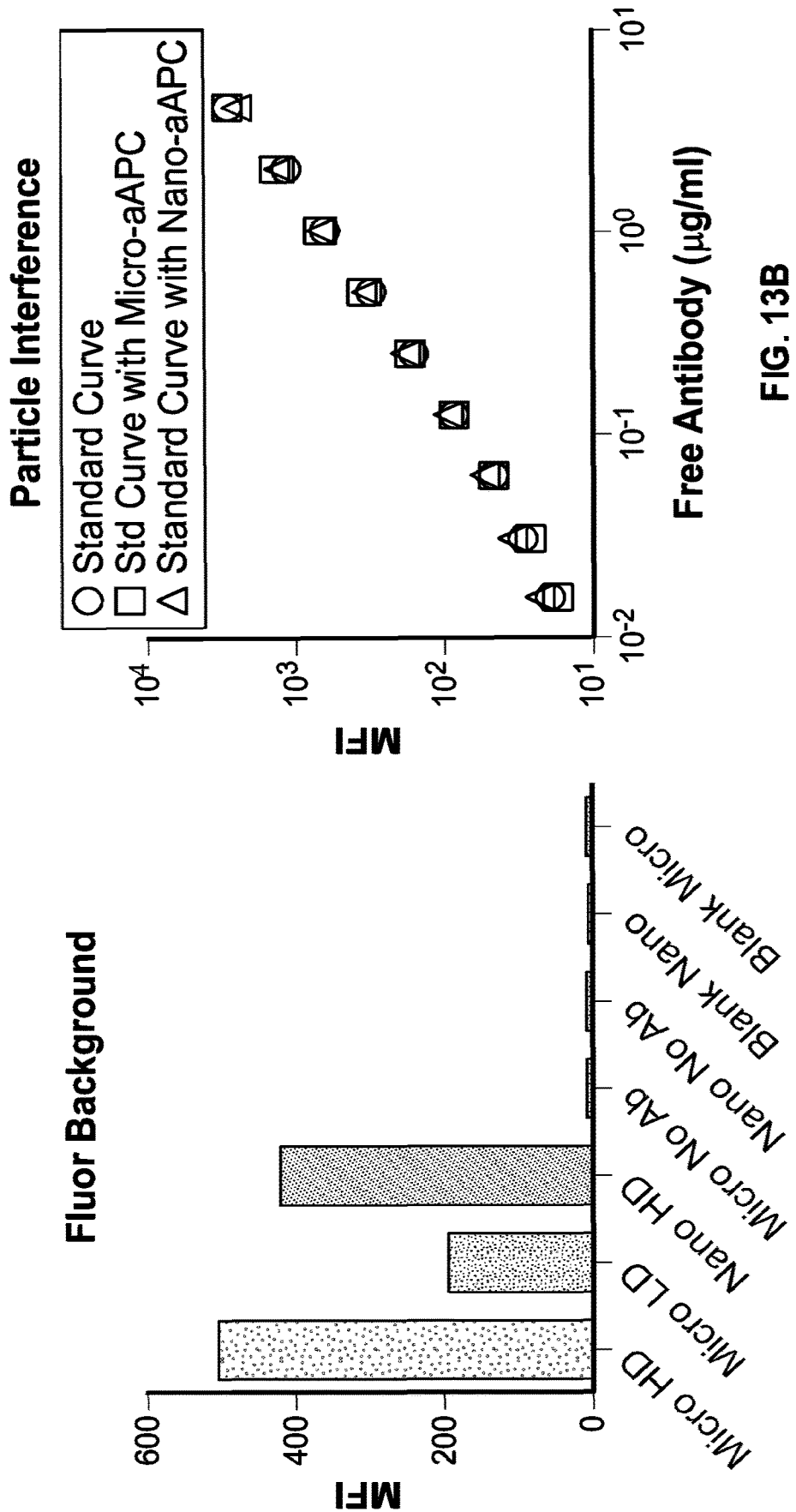
FIGS. 13A-D. Characterization of Protein Bound to Nano- and Micro-aAPC By Fluorescence.
Figures 13C, 13D:
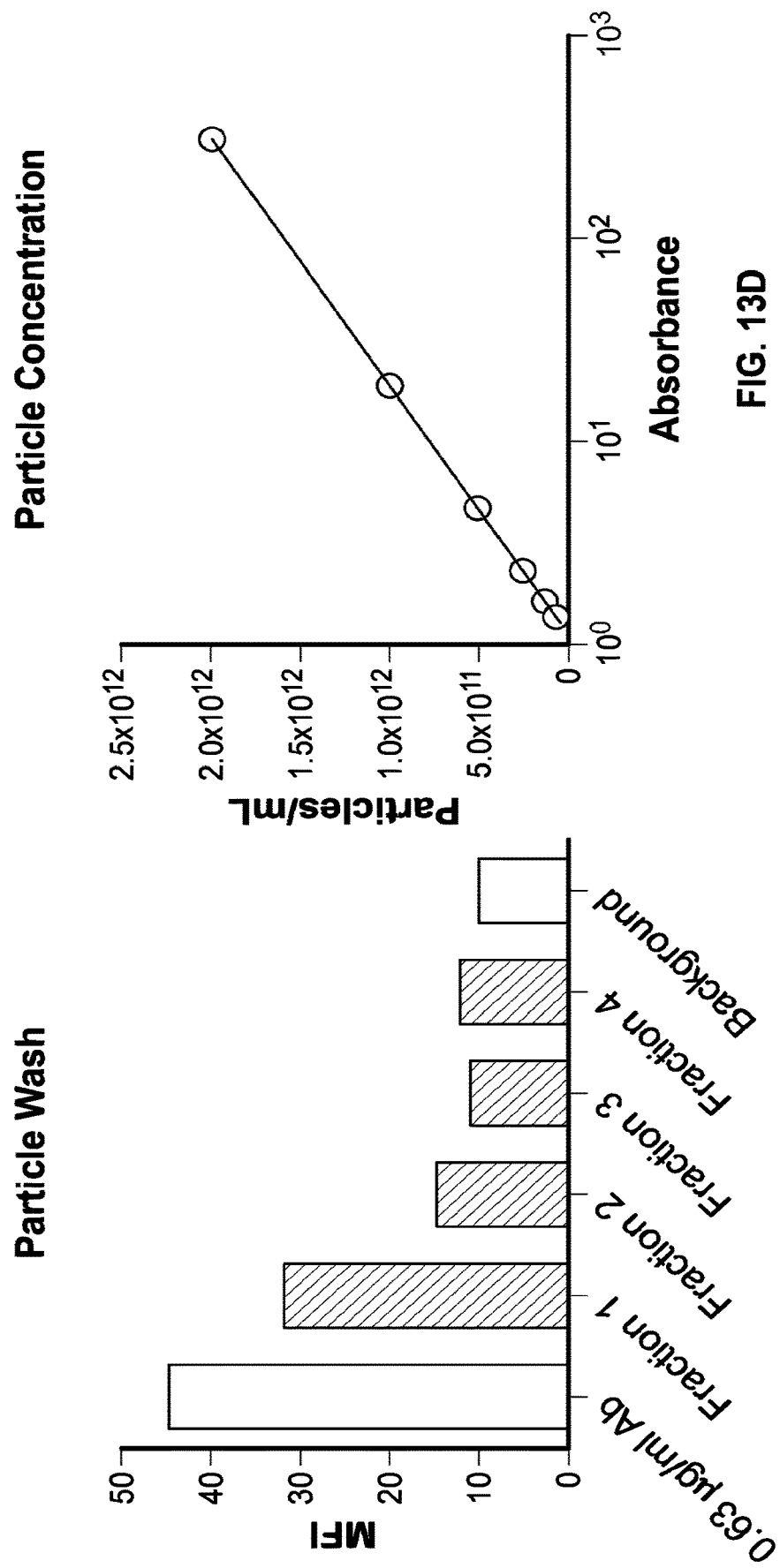

T cell stimulation requires two activating signals delivered by endogenous APC: signal 1, a cognate antigenic peptide presented in the context of MHC that binds the TCR, and signal 2, one of a number of co-stimulatory receptors that modulate T cell responses.22 Nano-aAPC are synthesized by coupling chimeric MHC-Ig dimer (signal 1) and anti-CD28 antibody (signal 2) to 50-100 nm paramagnetic iron-dextran nanoparticles (FIG. 9A), which were selected as a nanoscale particle platform due to their extensive characterization and biocompatibility.23 Protein coupling to particles was characterized by labeling with a fluorescent antibody against the protein of interest (FIG. 13). Nano-aAPC present 13±3 MHC-Ig dimers and 12±5 anti-CD28 antibodies per particle, for a protein density of 96±10 and 92±12 protein/μm2, respectively (Table 1).

TABLE 1

| Particle | Particle mean diameter (μm) | MHC-Ig dimers per particle | MHC-Ig density (protein/μm$^2$) | anti-CD28 per particle | anti-CD28 density (protein/μm$^2$) |
|---|---|---|---|---|---|
| nano-aAPC | 0.1 | 13 ± 3 | 96 ± 10 | 12 ± 5 | 92 ± 12 |
| Kb-SIY | 0.1 | 29 ± 6 | 214 ± 12 | — | — |
| Kb-SIY Alone Nanoparticle | 0.1 | 29 ± 6 | 214 ± 12 | — | — |
| Micro HD | 4.5 | 49,900 ± 2800 | 196 ± 11 | 27,200 ± 4600 | 107 ± 18 |
| Micro LD | 4.5 | 15,300 ± 1000 | 60 ± 11 | 14,400 ± 4500 | 56 ± 17 |

The amount and density of MHC-Ig and anti-CD28 on the surface of micro- (cell-sized) and nano-aAPC. Protein was quantified as described in in the description of FIG. 13, and particle concentration was determined by counts (micro-aAPC) or Nanoparticle Tracking Analysis (nano-aAPC). High (HD) and low (LD) density particles were synthesized by varying amount of protein per particle during synthesis. Signal 1 nanoparticles were synthesized without anti-CD28.

Figure 14A:
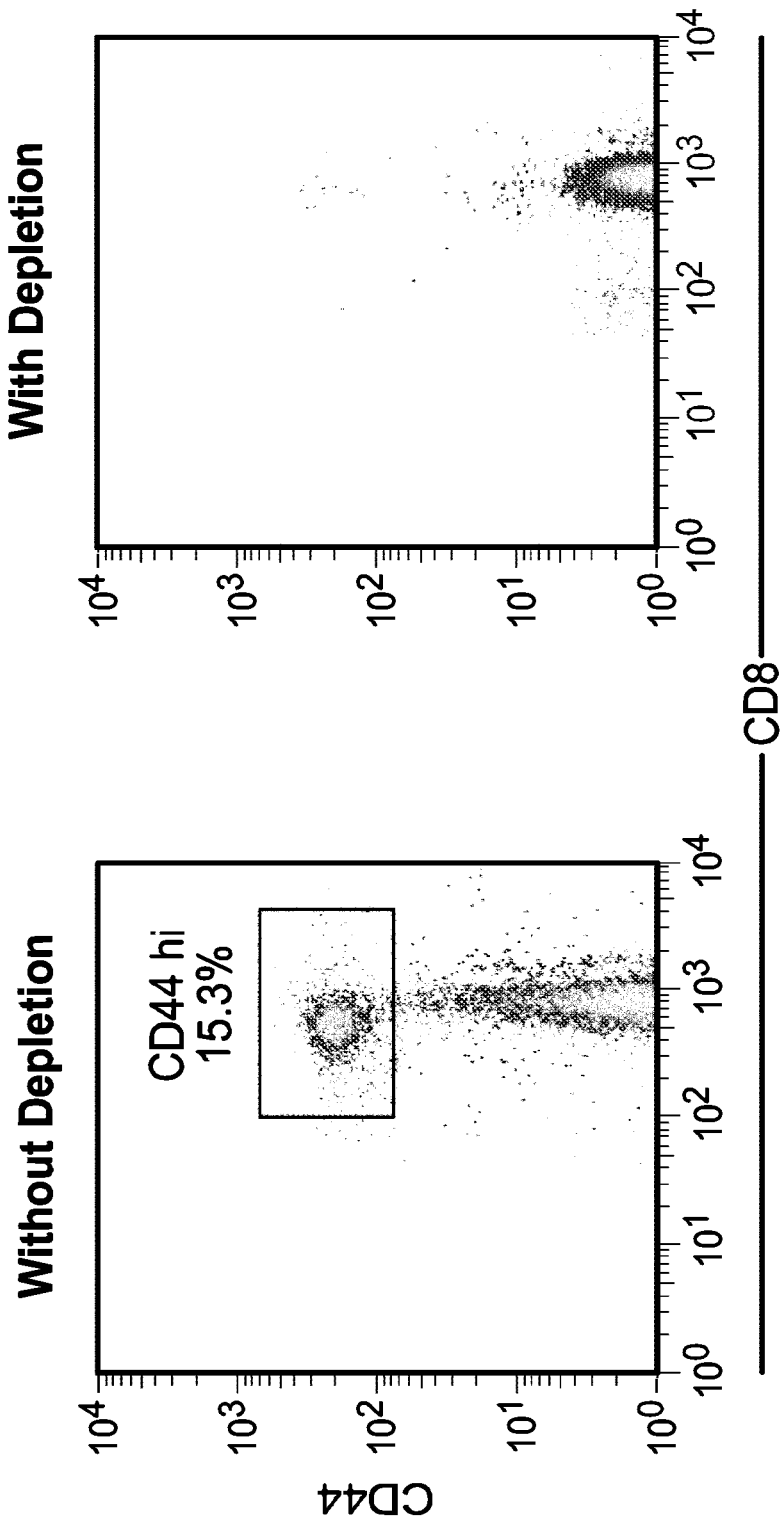
FIGS. 14A-E. pMEL T cell Proliferation Induced by Micro-aAPC.

To compare stimulation of naive versus previously activated T cells, we used CD44 depleted naive CD8+ splenocytes isolated from either pmel TCR or 2C TCR transgenic mice (FIG. 14A). This technique allowed us to isolate the truly naive T cells with defined antigenic specificities, whereas our previous work[3] and the work of others[24,25] relied on mixed populations of CD44 negative and CD44 high, naive and memory, cells found in transgenic mice. Activated cells were generated by stimulating CD8+ splenocytes for seven days with soluble peptide, GP100 for pmel T cells and SIY for 2C T cells.

Three days after stimulation with a low dose of nano-aAPC presenting 8 ng total MHC-Ig, naive pmel T cells had not proliferated as measured by CFSE (FIG. 9B, left), a vital dye that is diluted with each cell division. At the same dose, however, activated cells proliferated robustly (FIG. 9B, right). Nano-aAPC titration showed that naive cells had a higher threshold for nano-aAPC-induced proliferation (8-10 ng of total MHC-Ig) than activated cells (less than 1.5 ng of total MHC-Ig) (FIG. 9C).

Figure 14B:
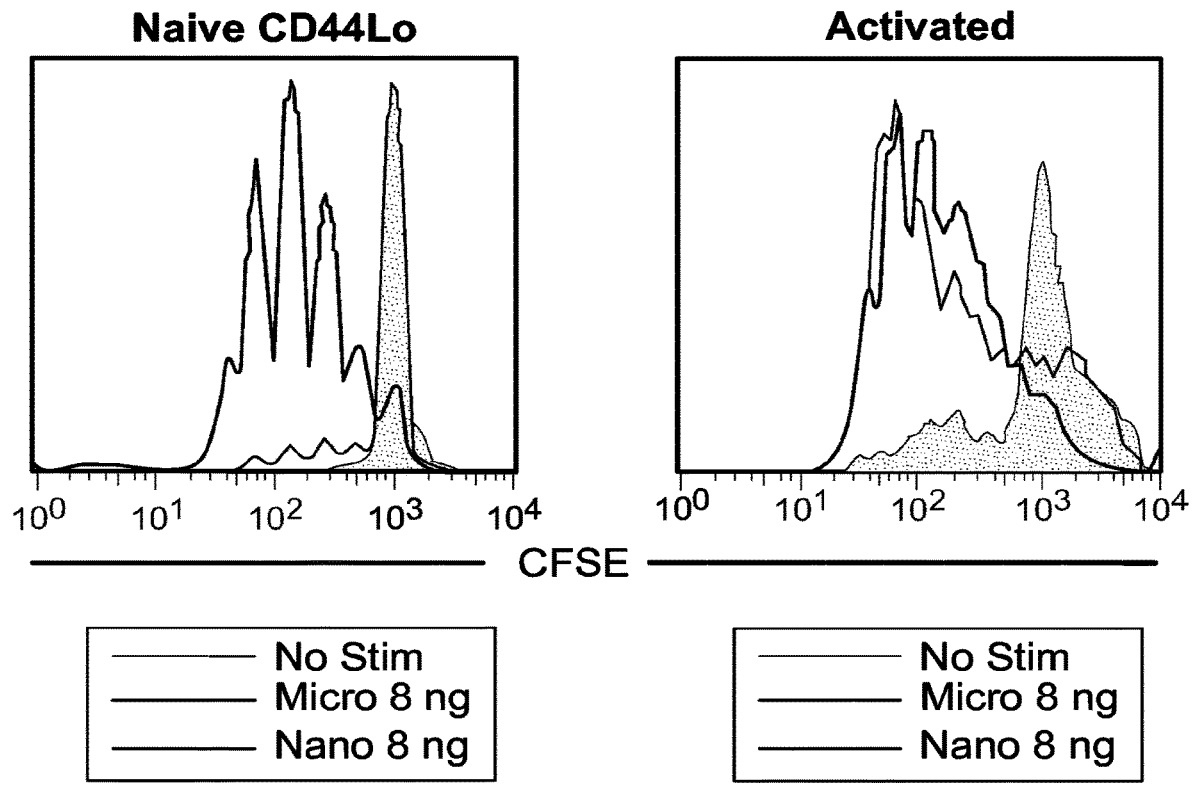
Figure 14C:
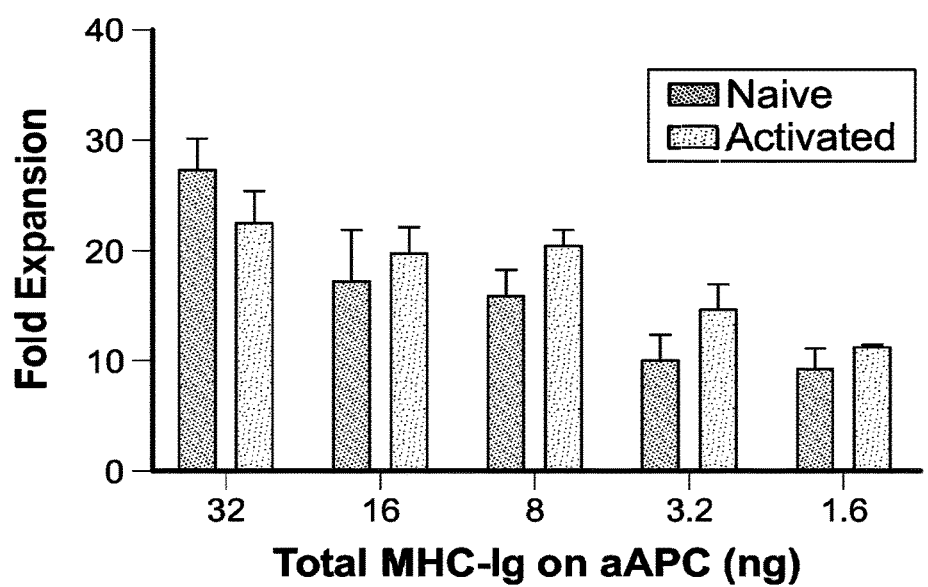

As control for aAPC size, we assessed T cell proliferation induced by cell-sized, 4.5 μm diameter iron-dextran micro-aAPCs. Micro-aAPC induced naive T cell proliferation at lower doses (1.5-8 ng MHC-Ig) than nano-aAPC as measured by CFSE dilution on day 3 (FIG. 14B), with approximately 10-20 fold expansion on day 7 (FIG. 14C).

Figure 14D:
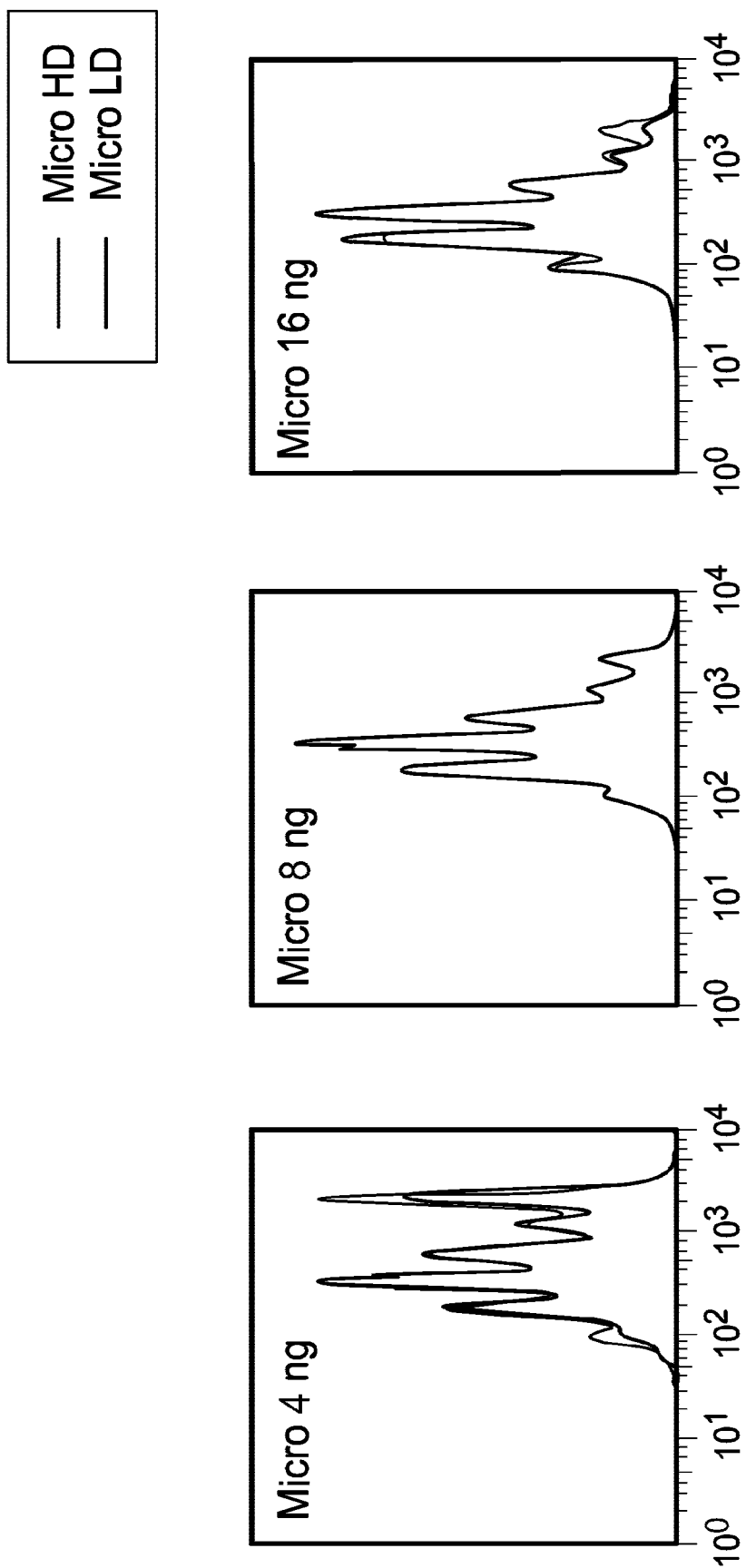
Figure 14E:
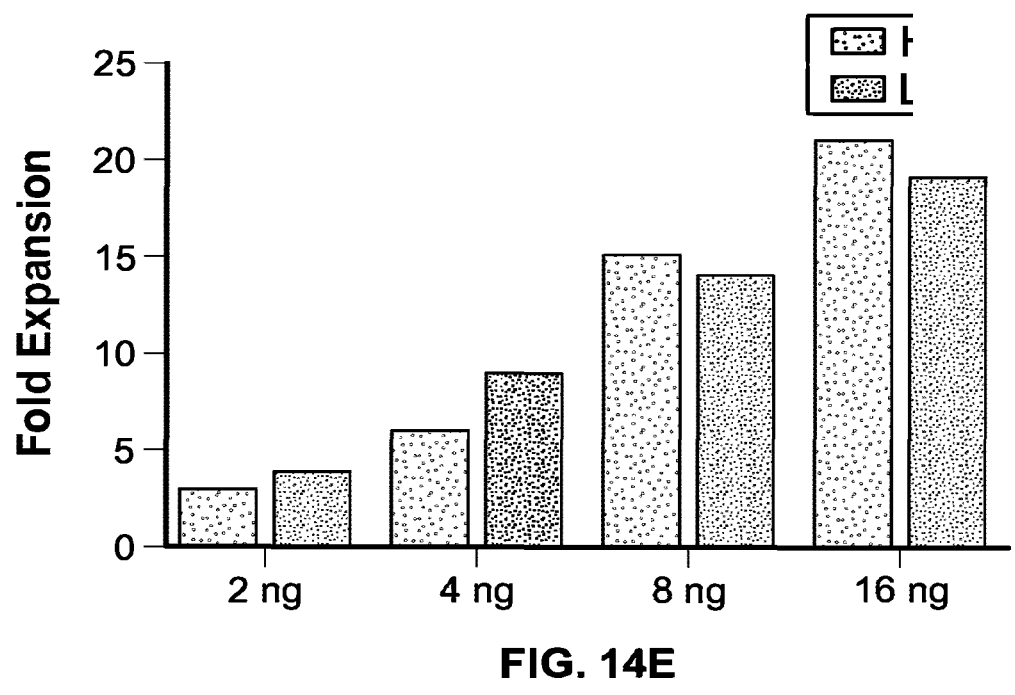
Figure 15B:
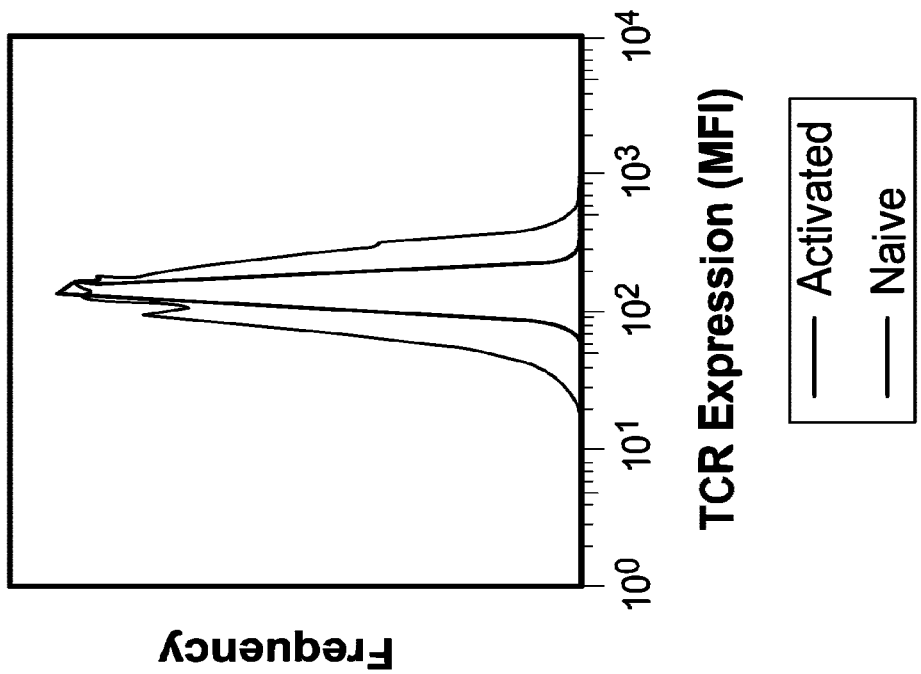
FIGS. 15A-D.
Figure 15A:
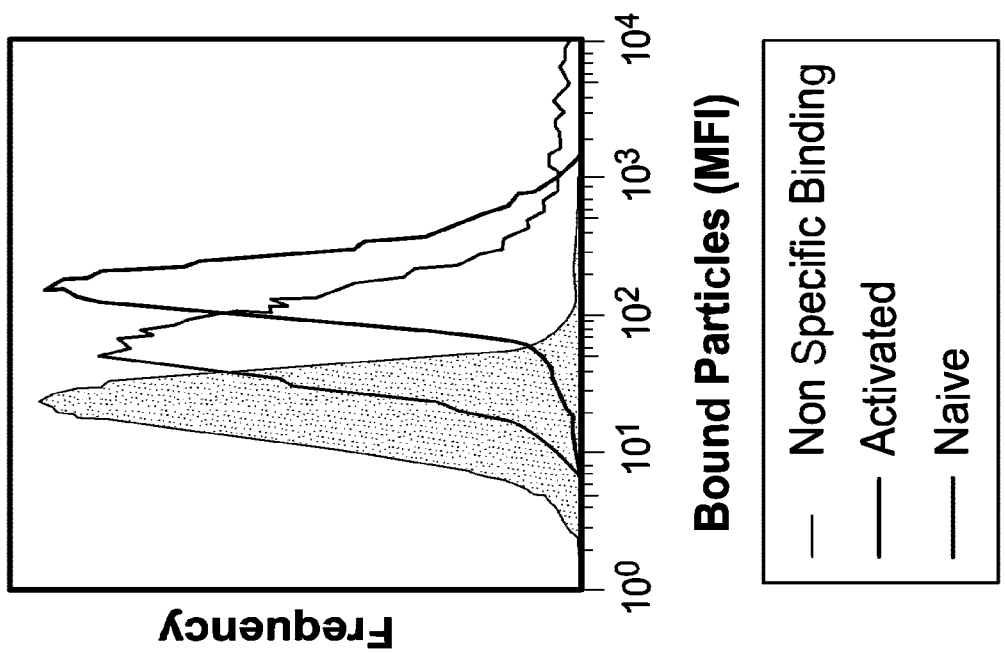
Figure 15C:
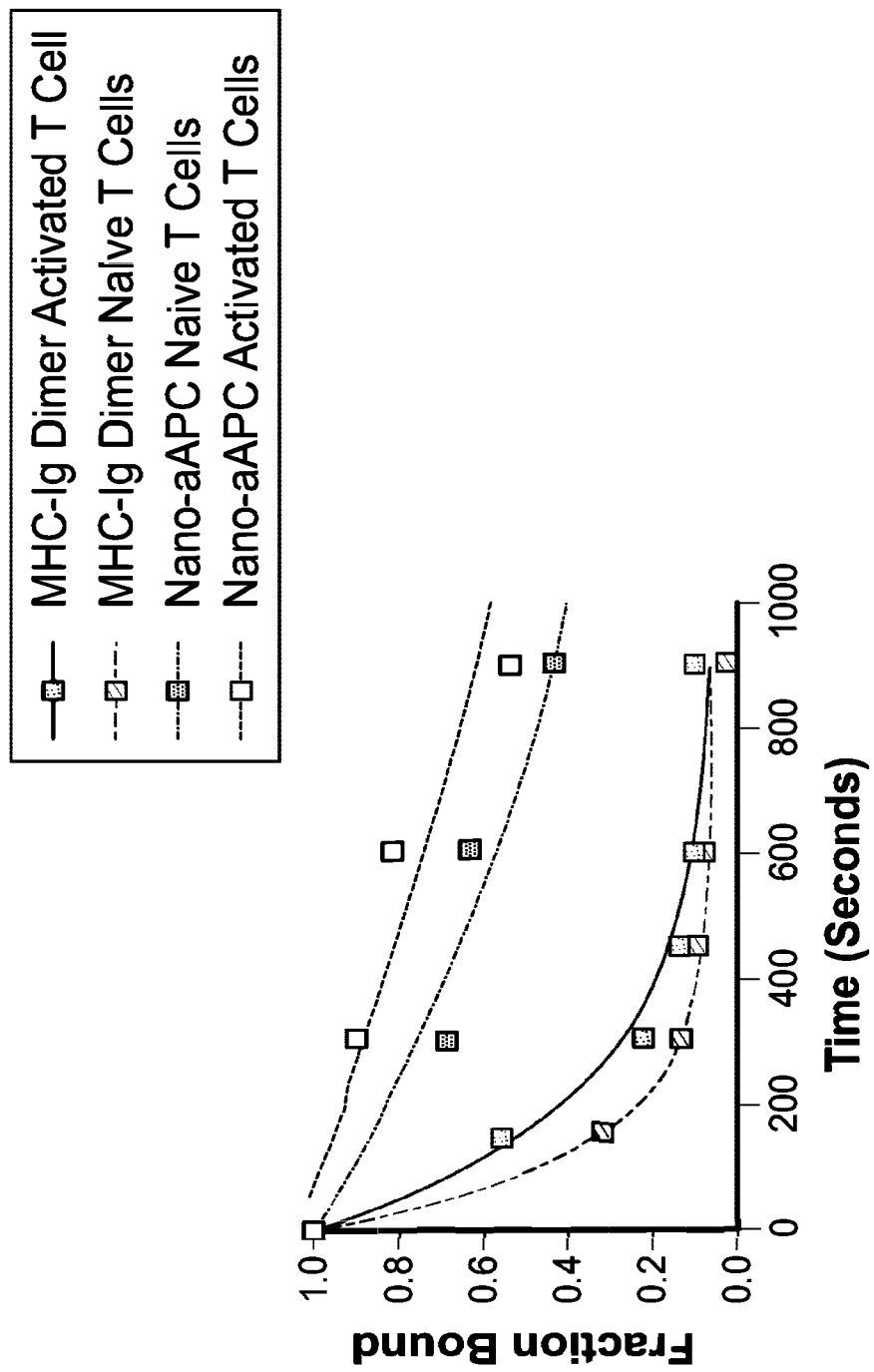
Figure 15D:
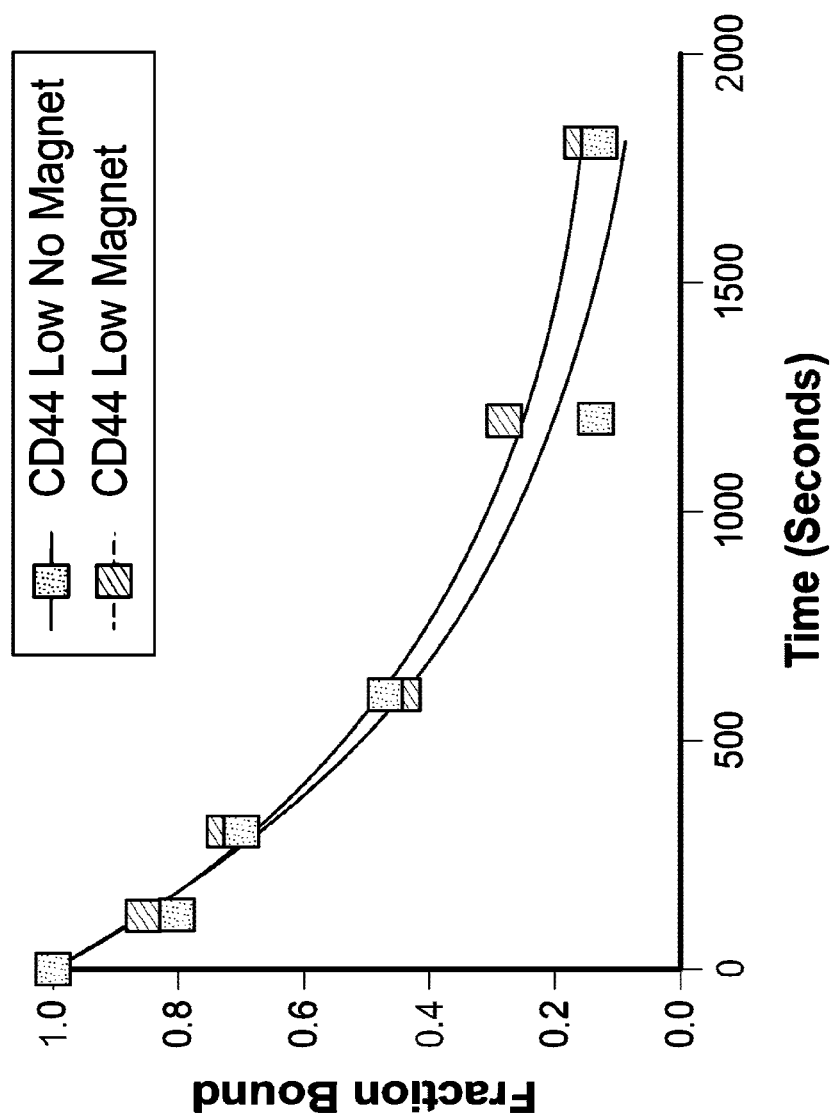
Figure 16C:
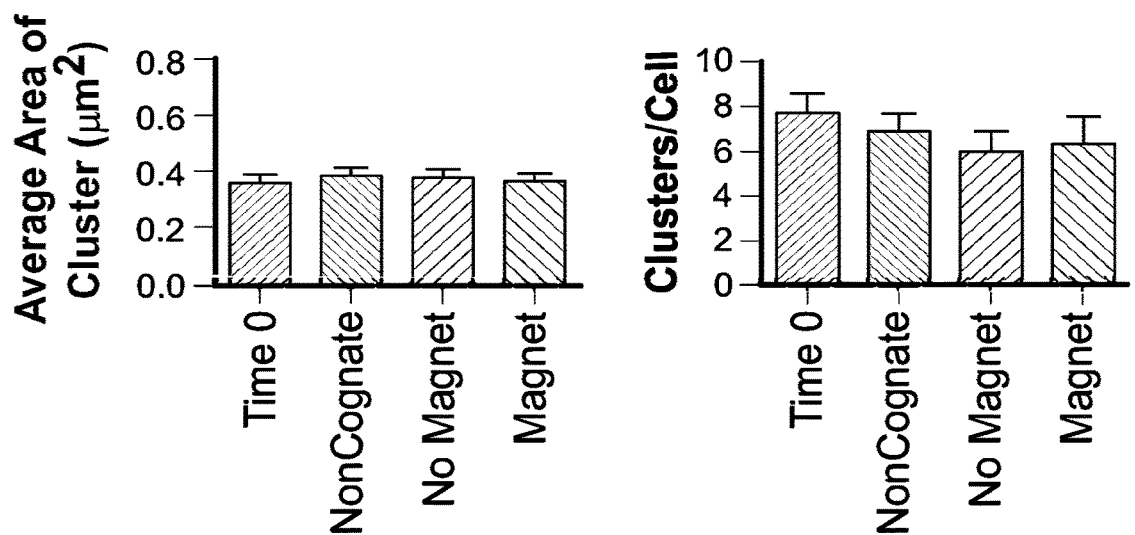
Figure 16D:
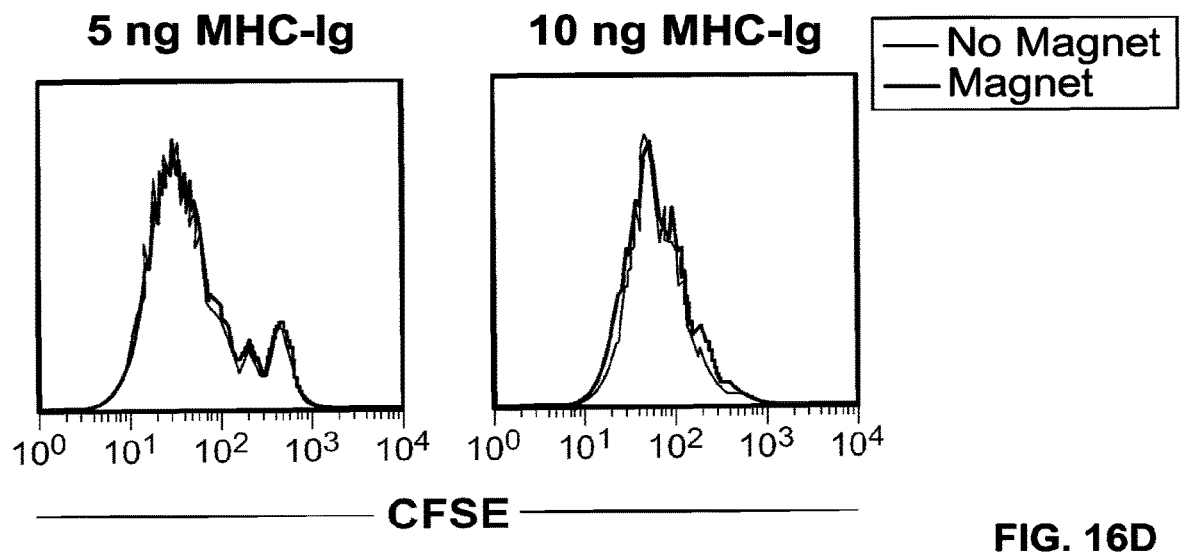
Figure 16E:
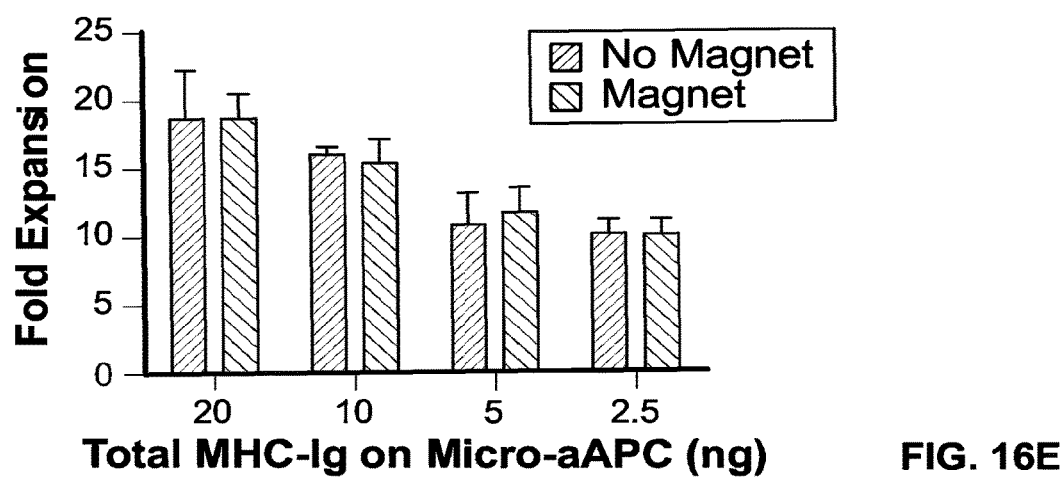
Figure 17:
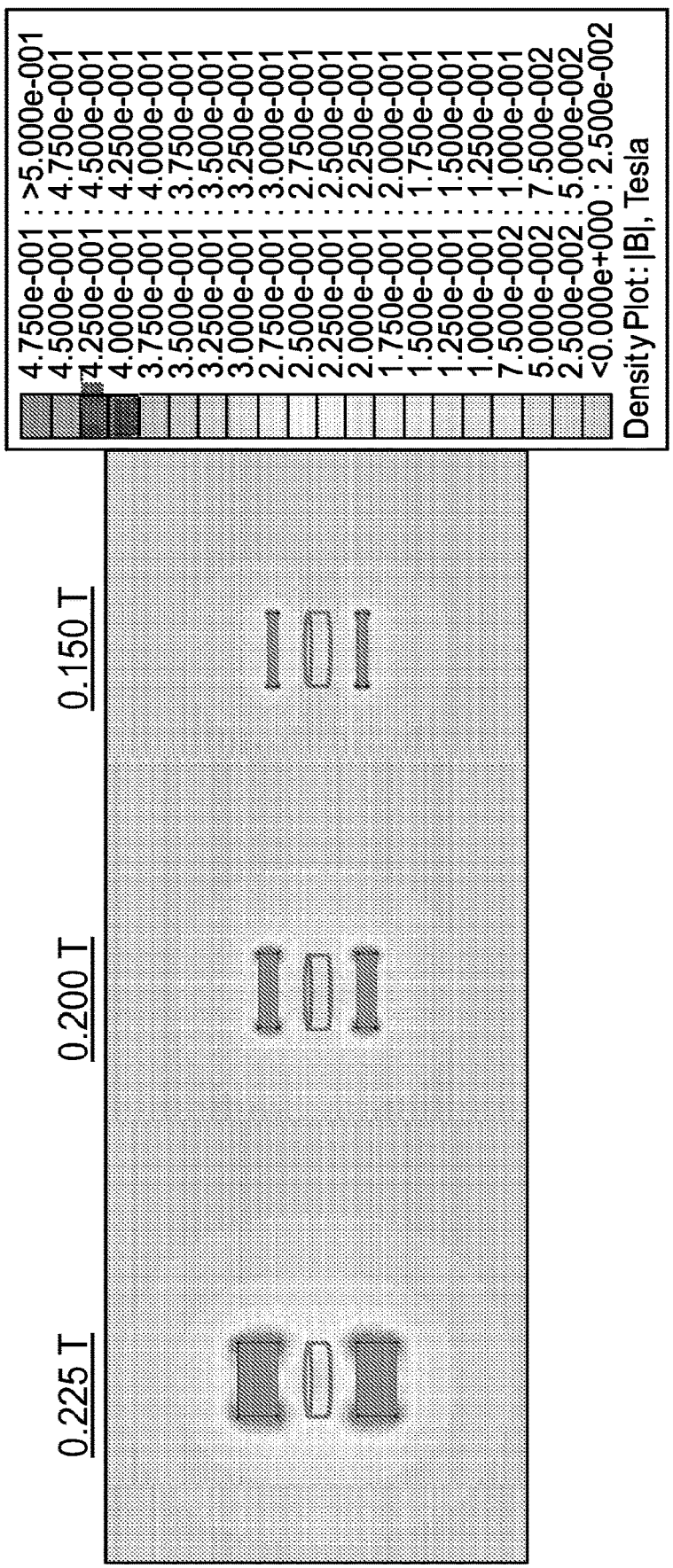
FIG. 17. Magnetic Field Strength Generated in Culture by Neodynium Disk Magnets. Density plots of field strength in culture as estimated by finite element analysis with FEMM (Finite Element Method Magnetics) software. Disk magnets (magenta) ¾", ¼", and ⅛" in thickness were used to generate fields of up to 0.225 T, 0.200 T, and 0.150 T, respectively.

Thus, while activated cells respond equivalently to nano- and micro-aAPC, naive cells have a higher threshold for nano-aAPC based stimulation. This difference was not driven by differences in protein density between micro- and nano-aAPCs, as micro-aAPCs with higher density (HD) and lower density (LD) than nanoparticles based aAPC induced identical proliferation when normalized for total MHC-Ig (FIG. 14D and FIG. 14E). Since response was sensitive to particle size, we hypothesized that the difference in responses were due to differences in nanoparticle interactions with TCR nanoclusters on naive versus activated cells.

EXAMPLE 10. NANO-AAPC BIND MORE TCR ON ACTIVATED THAN NAIVE CELLS

To examine nanoparticle binding to TCR, we synthesized nanoparticles bearing MHC-Ig alone, thus removing the binding contribution of anti-CD28. Binding experiments were performed on naive and activated T cells, which bound nanoparticles bearing cognate MHC-Ig specifically and with low background (FIG. 7A).

Figure 9D:
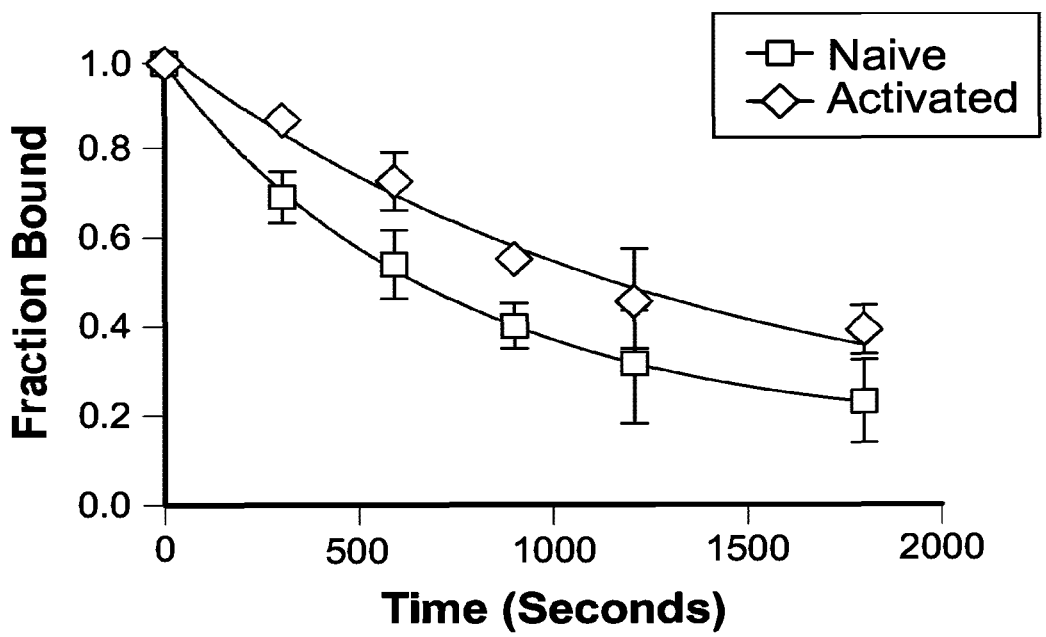

Nanoparticles were bound to naive and activated cells to equilibrium, followed by the addition of the anti-clonotypic 1B2 blocking antibody to prevent re-binding. Nanoparticles showed faster disassociation from naive cells (half-life of 531 seconds+149) than activated cells (984 s±221) (p<0.02 by paired Student's t-test) (FIG. 9D, Table 2).

TABLE 2

| Ligand | T Cells | Off-Rate (s$^{-1}$)[A] | Half-Life (s)[B] | TCR-MHC Contacts[C] |
|---|---|---|---|---|
| MHC-Ig Dimer | Naive | 8.9 × 10$^{-3}$ | 78 | 1 |
| | Activated | 5.2 × 10$^{-3}$ | 112 | 1.7 |
| Nanoparticle | Naive | (2.0 ± 0.5) × 10$^{-3}$ | 531 ± 149** | 6.8 |
| | Activated | (0.9 ± 0.2) × 10$^{-3}$ | 984 ± 221** | 12.6 |

[A]Off-rates experiments were performed by incubating naive or activated 2C TCR transgenic T cells with APC-labeled MHC-Ig or APC-labeled nanoparticles bearing Kb-SIY alone. After incubation for one hour at 4° C., cells were washed, a Time 0 fluorescence measurement was taken, and 1B2, an anti-clonotypic antibody, was added to prevent re-binding. Fluorescence measurements were then repeated at 2-10 minute intervals. Off-rates were calculated from a one-dimensional exponential fit in GraphPad Prism.
[B]Half-lives were derived from off-rates in column A. Particles bound to activated cells had a significantly longer half-life (**p < 0.02 by paired t-test, where measurements were paired by experiment) than particles bound to naive cells. Three experiments were performed for each condition.
[C]Unbinding of individual MHC-Ig on either dimer or particle can be stochastically modeled as a Poisson (aka memoryless or exponential) Process. For a Poisson Process with rate constant r, the departure time of the nth event is characterized by a gamma distribution with shape parameter n and single-event rate parameter r:

$$f_n(t) = r^n \frac{t^{n-1}}{(n-1)!} e^{-rt}, 0 \le t < \infty$$

The mean of this distribution E[t]=n/r. If MHC-Ig dimer is assumed to make one contact with a naive T cell (Fahmy, T. M.; Bieler, J. G.; Edidin, M.; Schneck, J. P. Increased TCR Avidity after T Cell Activation: a Mechanism for Sensing Low-Density Antigen. Immunity 2001, 14, 135-43), then r can be estimated from the off-rate of MHC-Ig on naive cells (8.9×10$^{-3}$). Thus, for any given condition, E[t] is derived from the half-life of MHC-Ig dimer or particle on naive or active cells ($t_{1/2}$), and r is assumed constant. The number of TCR-MHC contacts is estimated as n:

$$n = \frac{t_{\frac{1}{2}} * r}{\ln(2)}$$

The true number of contacts is likely to be higher than this estimate, as MHC-Ig are likely to make more than one contact with naive cells.

12721 Disassociation rates can be used to estimate the number of contacts between cells and multivalent ligands, with more contacts leading to slower disassociation. 26 Nanoparticle disassociation from cells was modeled as an exponential stochastic process, with disassociation of soluble MHC-Ig dimer used to derive parameters and validate the approach (see Table 2 for details). The off-rate of a single TCR-MHC contact was measured for soluble MHC-Ig dimer binding to naive cells (FIG. 7C), which is effectively monovalent.[13] As expected, MHC-Ig dimers disassociated more slowly from activated cells, leading to 1.7 estimated contacts (FIG. 9E), consistent with previous reports.[13,26]

Figure 9E:
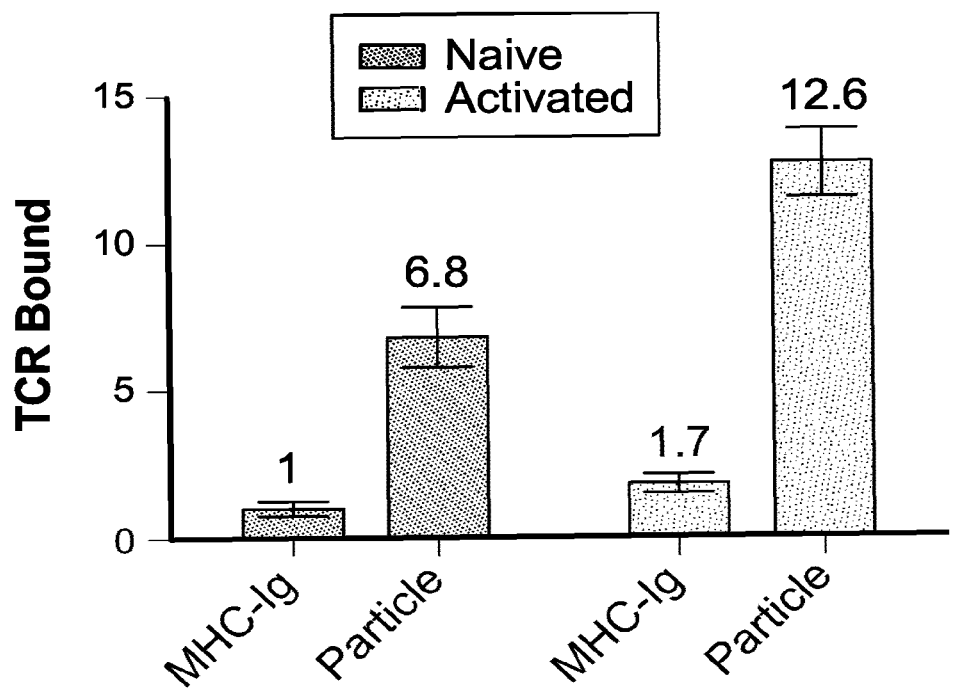

Nanoparticle disassociation from naive cells was significantly slower than free MHC-Ig (FIG. 7C), and 2-fold slower from activated cells than naive. Nano-aAPC thus made an estimated 6.8 contacts with naive cells, compared to approximately double (12.6) on activated cells (FIG. 9E, Table 2). These numbers represent 11% and 22% of MHC-Ig dimers, respectively, attached to the surface of nano-aAPC.

Figure 9F:
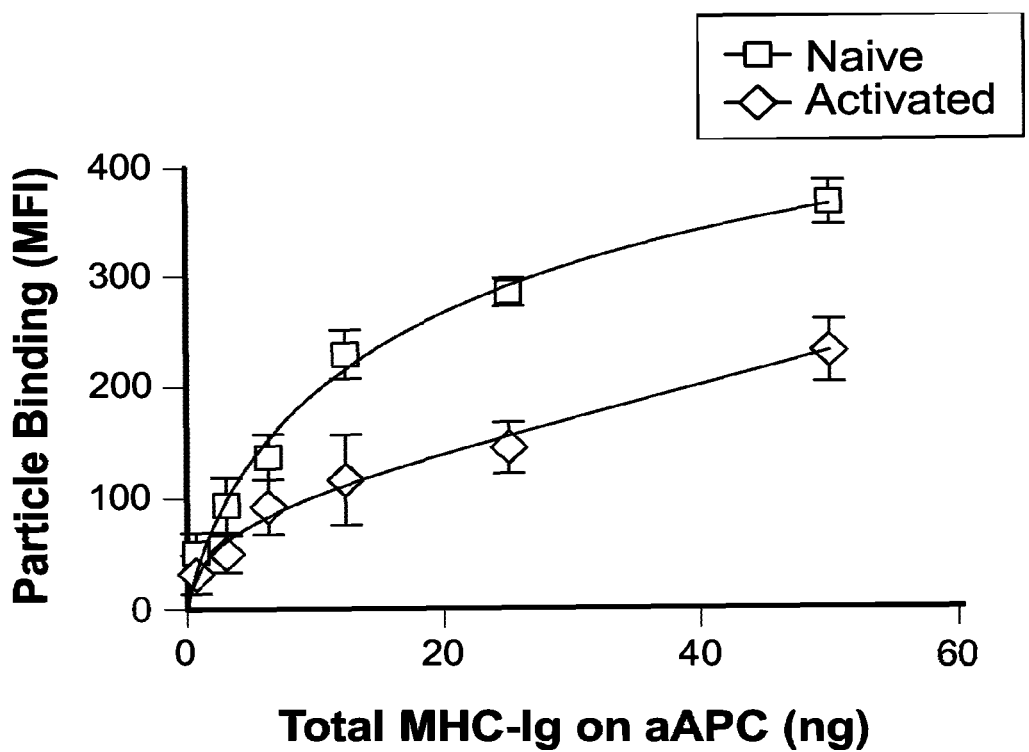

Activated cells bound two-fold fewer nanoparticles at equilibrium than naive cells across a wide range of particle concentrations (FIG. 9F). This difference was not due to T cell receptor expression, which was equivalent on naive and activated T cells (FIG. 7B), indicating that increased TCR-MHC contacts per particle leads to fewer available TCR, inhibiting binding and limiting the total amount of nanoparticles that bind to an individual cluster.

Figure 9G:
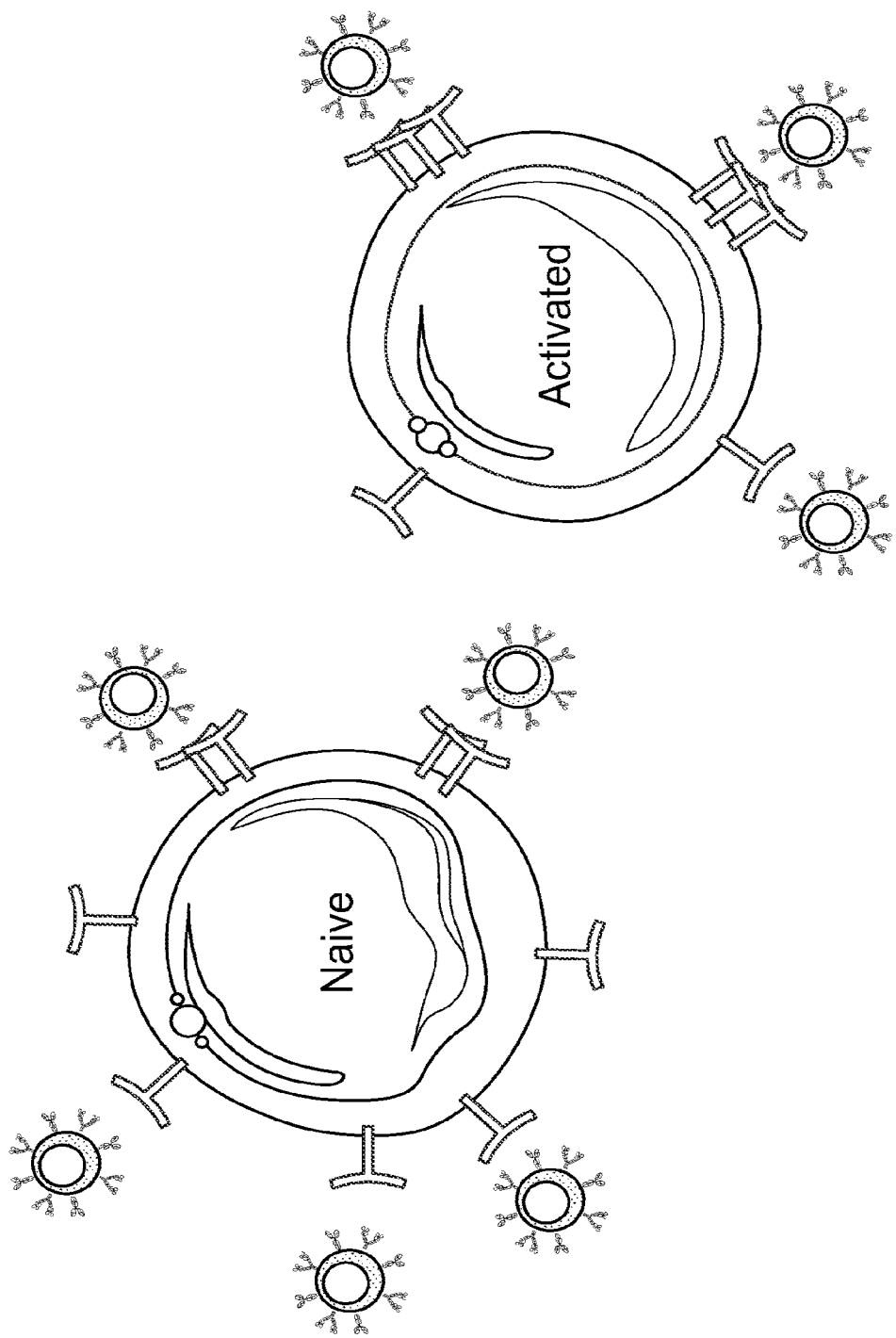

Together, the two-fold increase in total nano-aAPC bound and two-fold decrease of the TCR-MHC contacts engaged by naive cells suggest the binding model shown schematically in FIG. 9G. Naive cells bind more nano-aAPC utilizing fewer MHC contacts due to the small scale of TCR clusters prior to cell-nanoparticle contact. Activated cells, in contrast, bind fewer nanoparticles because each particle makes contact with more TCR.

EXAMPLE 11. MAGNETIC FIELDS DRIVE AGGREGATION OF AAPC AND TCR/CD3

Based on the hypothesis that nano-aAPC bound to nanoscale TCR clusters, we took advantage of nanoparticle binding to control TCR cluster aggregation, and thus T cell activation. An exogenous magnetic field was used to drive aggregation of paramagnetic nano-aAPC bound to naive cells. Nano-aAPC were bound to naive T cells at 4° C., then cultured at 37° C. between two neodymium disk magnets generating a maximum field strength of 0.2 T to determine whether, in an external magnetic field, paramagnetic iron-dextran aAPC would be magnetically polarized and attracted to each other,[27] driving aggregation of TCR (FIGS. 10A-C).

Cluster formation was assessed by confocal microscopy. After one hour of binding at 4° C., we either stained and fixed cells immediately (Time 0), or transferred cells to a 37° C. incubator for 30 minutes in the absence or presence of a magnetic field. Cells were then stained with antibodies against LFA-1 (green), an adhesion molecule used as a control; CD3ε (magenta), a signaling component associated with TCR; and MHC-Ig (red), to visualize the nano-aAPC. Finally, cells were fixed and imaged.

Prior to incubation at 37° C., aAPC and CD3E were distributed in a punctate pattern on the membrane, with small clusters diffusely distributed across the cell surface (Time 0, FIG. 10D top left). LFA-1 was uniformly distributed across the cell. The LFA-1 and CD3ε staining patterns were identical to those at Time 0 after thirty minutes of incubation with non-cognate Kb-SIINF particles (Non-Cognate, FIG. 10D top right). In the absence of a magnetic field, incubation with cognate nano-aAPC did not drastically alter the distribution of either LFA-1, aAPC, or CD3ε (No Magnet, FIG. 10D bottom left). However, after 30 minutes in a magnetic field, large aggregates of nano-aAPC formed on the membrane (Magnet, FIG. 10D bottom right). These clusters of nano-aAPC co-localized with similarly sized clusters of CD3ε. The control molecule LFA-1 maintained a diffuse pattern across the membrane, indicating that CD3ε aggregation was due to its association with aAPC.

To characterize the size and number of aggregates induced by aAPC, a particle-identification program was developed in ImageJ. The program was able to identify both diffuse, punctuate clusters from Time 0 cells (FIG. 10E left), and larger aggregates induced by magnetic fields (FIG. 10E right).

Figure 10G:
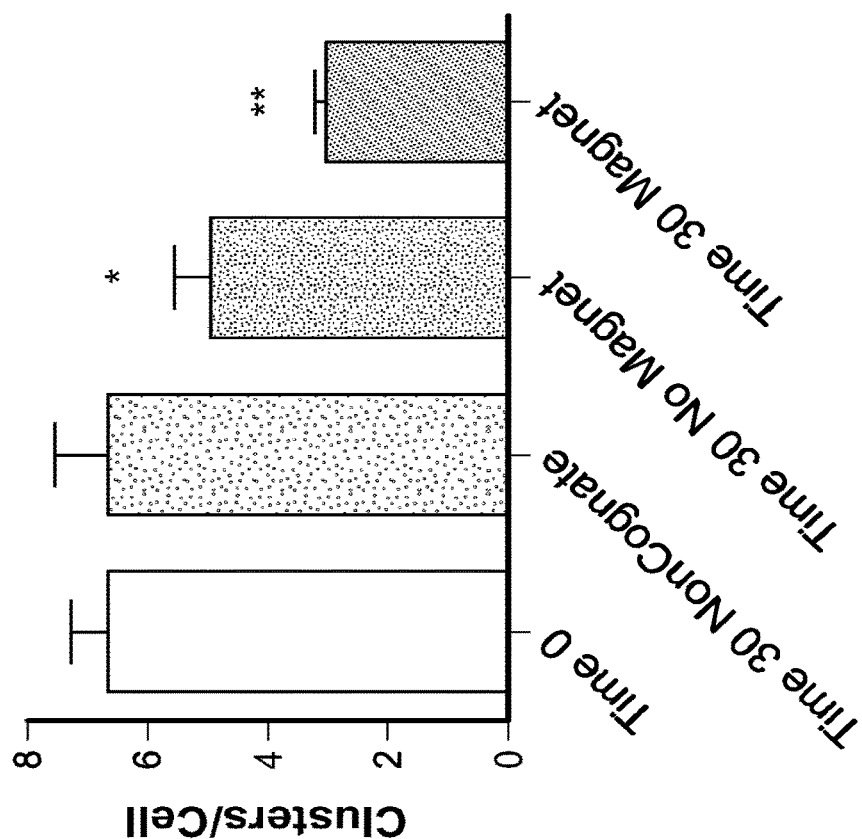
Figure 10F:
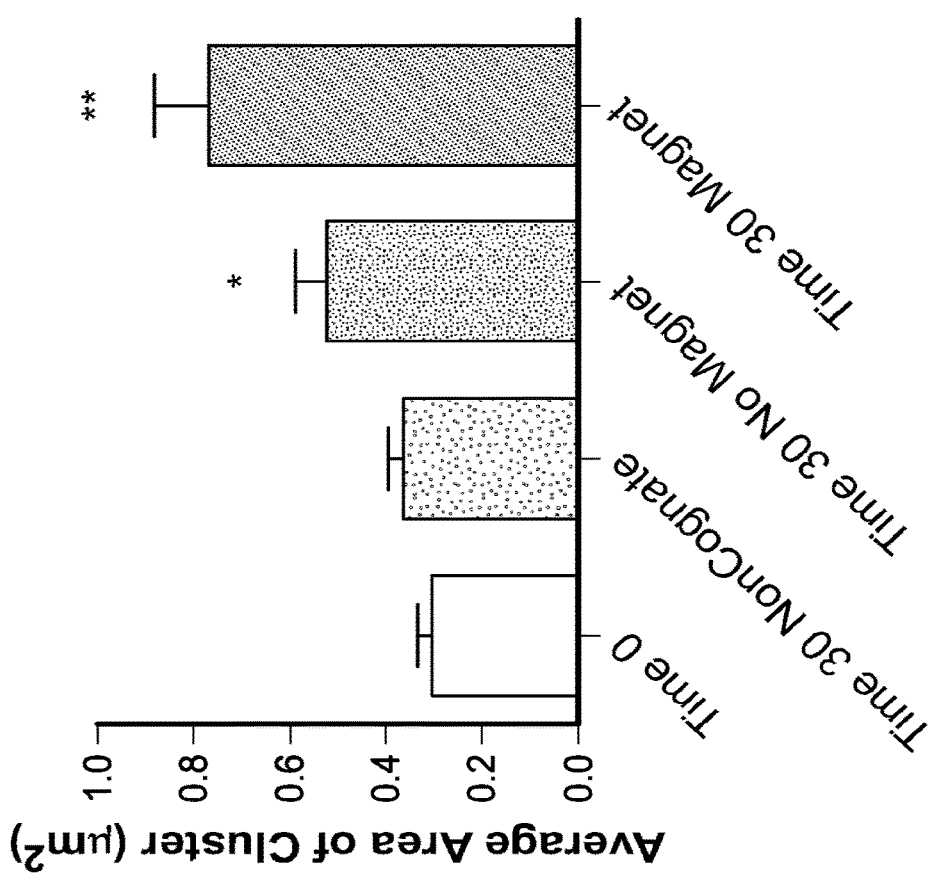

Incubation in a magnetic field significantly increased TCR aggregation, beyond that seen after incubation with nano-aAPC alone, and led to larger CD3 complex aggregates on cells. Mean cluster area prior to incubation at 37° C. was $0.30\pm0.03$ μm2, and this did not change after incubation with non-cognate nano-aAPC (FIG. 10F). aAPC alone increased cluster size to a mean of $0.52\pm0.06$ μm2 ($p<0.001$). Clustering was further enhanced in a magnetic field to a mean size of $0.73\pm0.11$ μm2 ($p<0.001$ compared to No Magnet). The mean number of clusters per cell decreased from $6.5\pm0.6$ at Time 0 to $3.0\pm0.2$ with a magnetic field (FIG. 10G). Nano-aAPC disassociation rate after culture in a magnetic field did not increase (FIG. 7F), suggesting aggregate formation was not associated with an increase in TCR/MHC contacts, but rather aggregation of TCR nanoclusters bound to aAPC.

The impact of external magnetic fields was also studied using micro-aAPC (FIG. 8A). While applying a magnetic field drove micro-aAPC aggregation, aggregation of micro-aAPC was not associated with aggregation of TCR/CD3 on cells. CD3 clusters on T cells were $0.39\pm0.03$ μm2 in area when incubated with micro-aAPC in the absence of a magnetic field, and $0.37\pm0.03$ μm2 with micro-aAPC in the presence of a magnetic field (FIGS. 8B-C), indicating that a magnetic field did not enhance CD3 clustering when T cells were stimulated with micro-aAPC. This is likely due to the large size of microparticles relative to TCR nanoclusters.

In summary, nano- but not micro-aAPC aggregation induced by a magnetic field led to a 2-fold increase in TCR/CD3 aggregate size and a 2-fold decrease in the number of aggregates per cell. Since receptor aggregation is known to be a strong and sufficient signal for T cell activation,[28] we examined the effect of magnet-induced TCR clustering on T cell proliferation.

EXAMPLE 12. ACTIVATION IN A MAGNETIC FIELD ENHANCES PROLIFERATION OF NAÏVE T CELLS

Figure 11E:
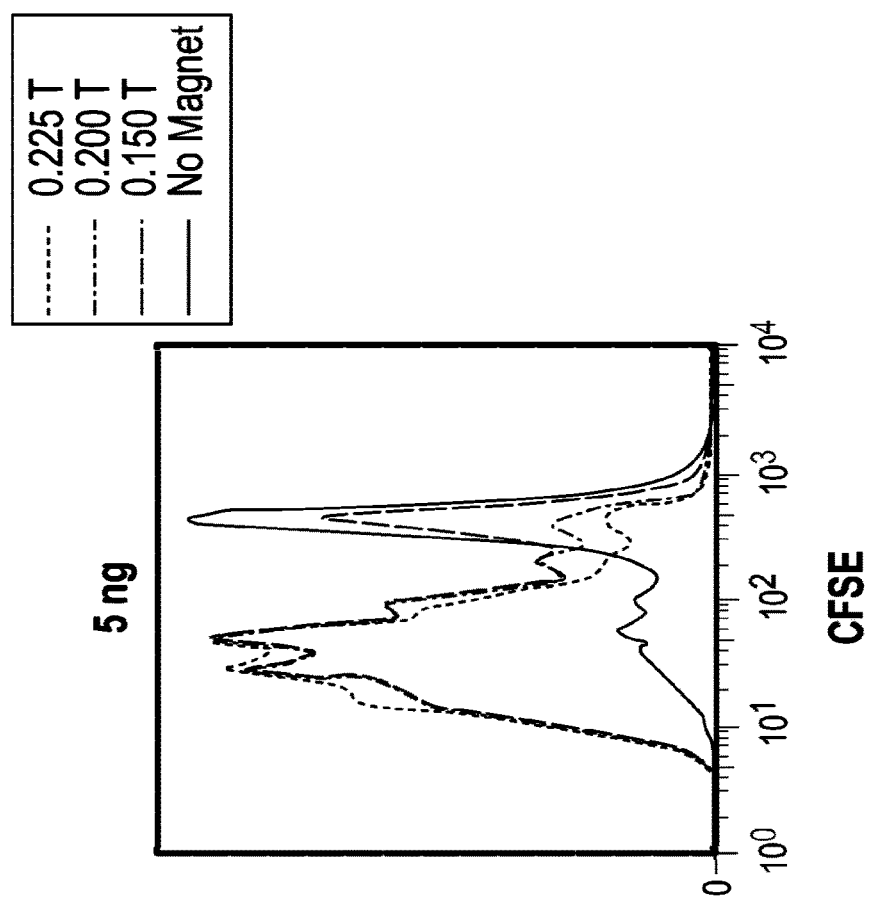

To assess whether activation of T cells by nano-aAPC was enhanced by culture in a magnetic field, CFSE-labeled pmel T cells were incubated with increasing doses of db-GP100 nano-aAPC and cultured with or without an external magnetic field. Naive T cells proliferated in a magnetic field at doses of nano-aAPC that induced minimal proliferation otherwise (FIG. 11A). After incubation with nano-aAPC bearing 5 ng MHC-Ig, 29% of cells in culture had proliferated, compared to 89% of cells in a magnetic field. Proliferation at day 7 was up to 4 fold greater compared to no magnet controls (FIG. 11B). Culture in a magnetic field without nano-aAPC did not lead to T cell proliferation.

Figure 8D:
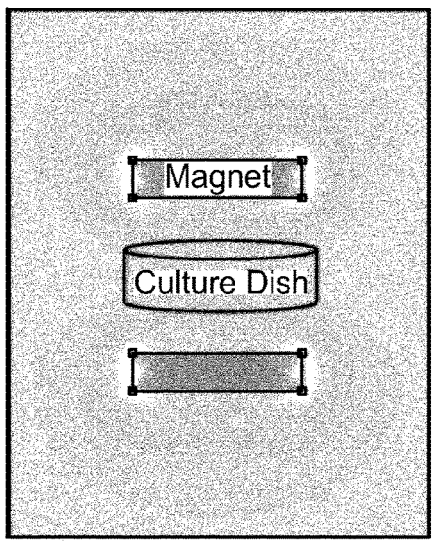
FIG. 8D. As a complementary approach, cells are activated in a magnetic field after pre-binding to nano-aAPC. Culture in a magnetic field boosts cell proliferation.
Figure 8E:
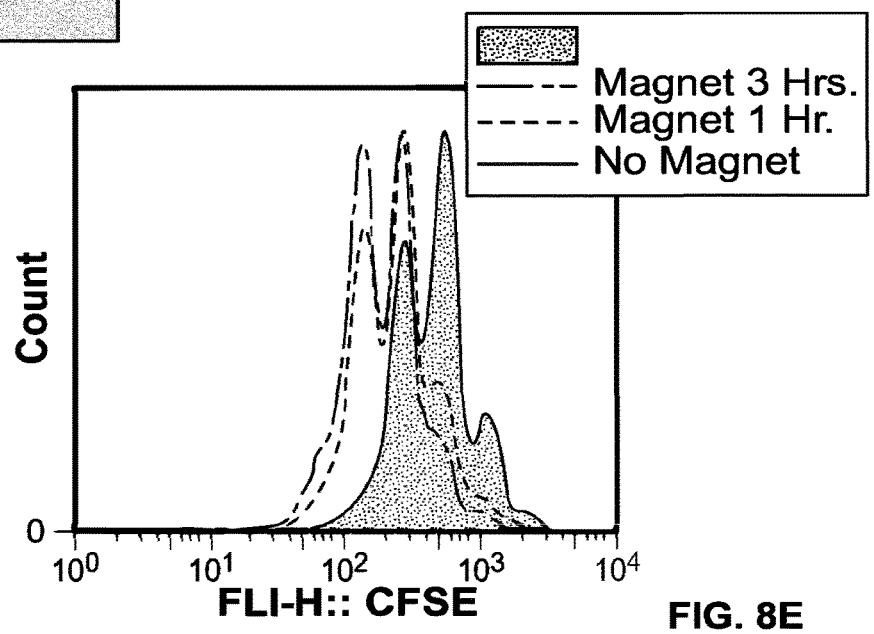
FIG. 8E. CFSE staining three days after activation shows magnet induced boosting after 1-3 hours of activation.
Figure 8F:
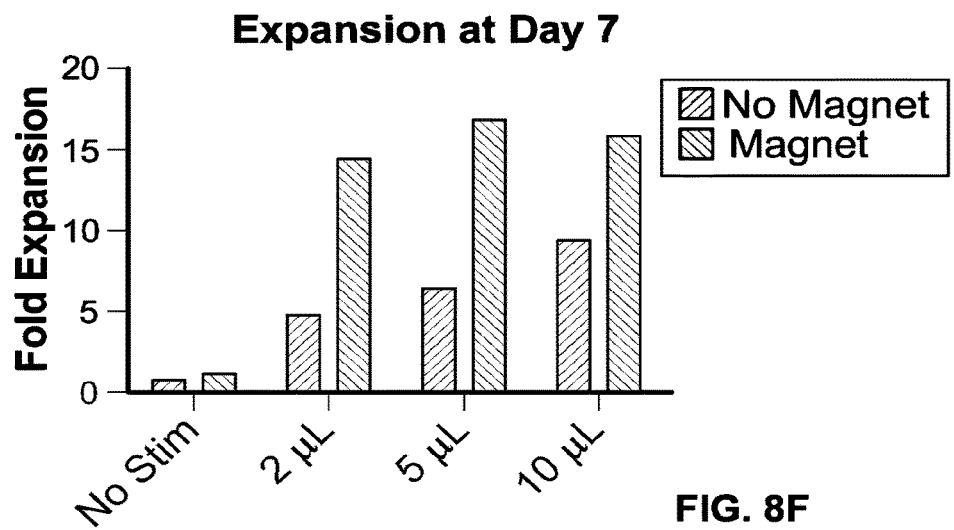
FIG. 8F, This leads to enhanced expansion measured seven days after activation, with magnetic stimulation providing a boost at all doses considered.

In contrast, culture with micro-aAPC in a magnetic field did not lead to enhanced T cell expansion compared to no magnet controls, as measured by both day 3 CFSE dilution and proliferation at day 7 (FIGS. 8D-E).

Magnetic bead clustering has previously been used to study effects of both mechanical stress[29] and receptor clustering[21,27] in other systems, and a role has been suggested for mechanical triggering of TCR.[30,31] However, since micro-aAPC in a magnetic field are likely to transmit greater mechanical forces than nano-aAPC but do not induce TCR aggregation or enhanced proliferation, the magnet-enhanced proliferation effect seen with nano-aAPC is likely due to receptor aggregation rather than mechanical receptor "pulling."

Figure 11D:
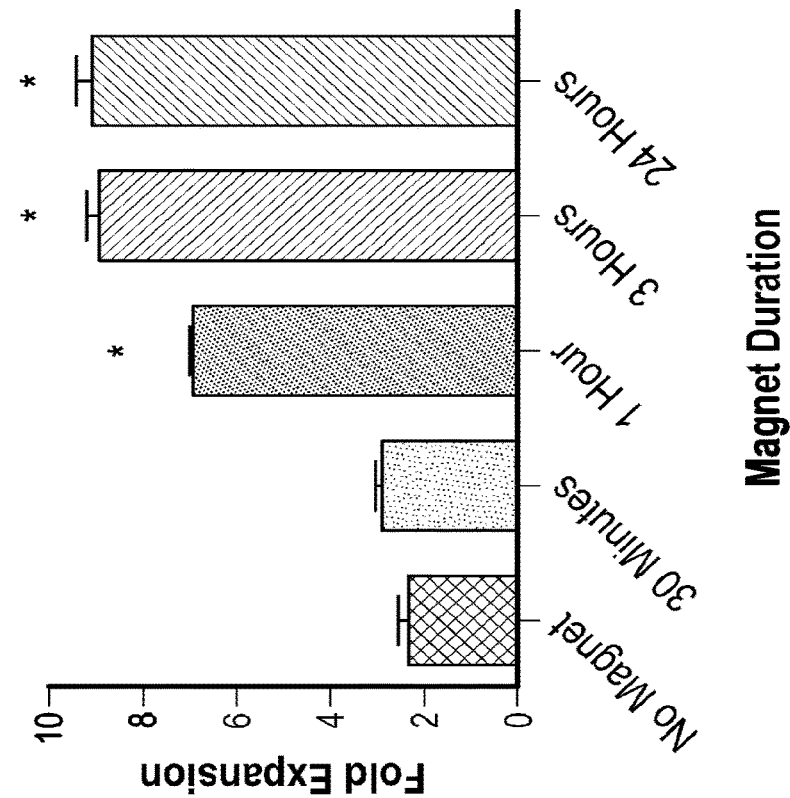
Figure 11F:
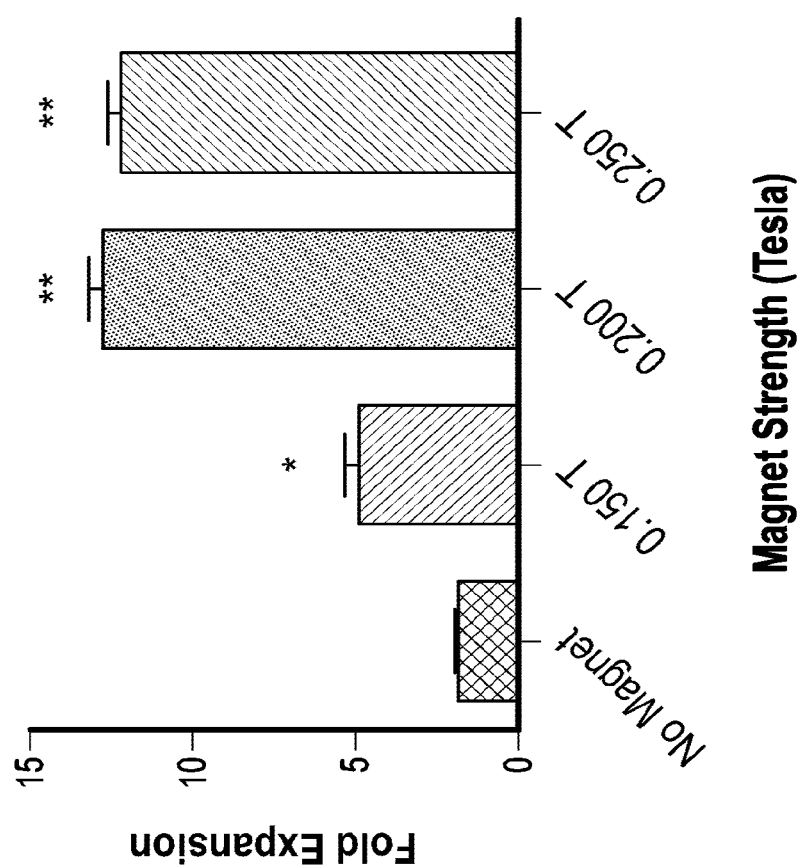

The duration and strength of magnetic field stimulation required for optimal expansion by nano-aAPC were assessed by the addition and removal of neodymium magnets of varying size. One to three hours in a magnetic field (FIGS. 11C-11D) and a field strength of 0.2 T or more (FIGS. 11E-3F; FIG. 13) drove 10-fold T cell expansion after one week.

Figure 11G:
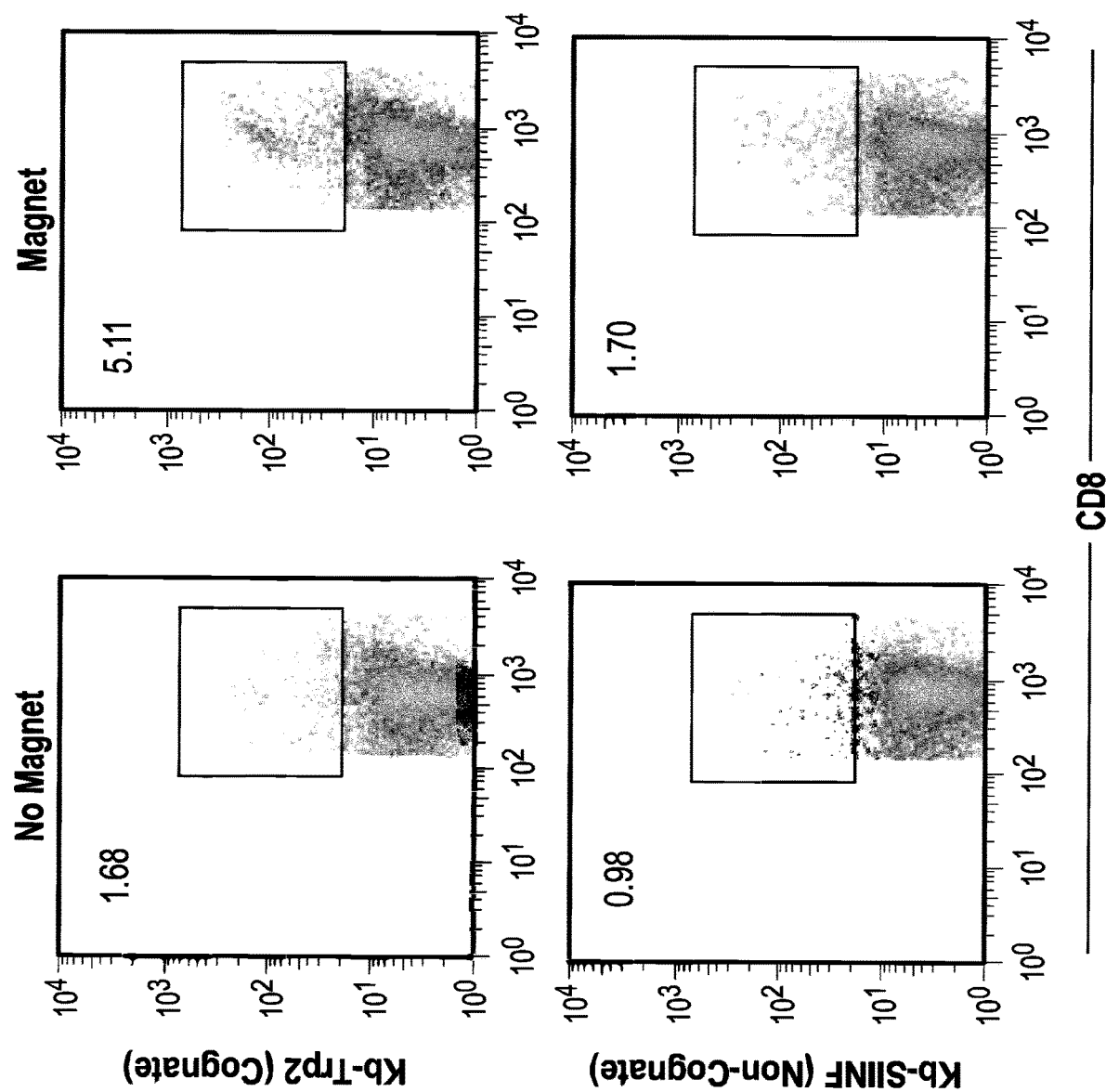

Magnetic field enhanced aAPC stimulation also enhanced expansion of antigen-specific T cells from endogenous, polyclonal T cell populations. We synthesized nano-aAPC bearing the Kb-Ig dimer loaded with the Trp2 peptide, which is specific for the Trp2 melanoma antigen. CD8+ splenocytes from wild type B6 mice were cultured with a limiting dose of aAPC and, after seven days, antigen-specific T cells were analyzed. Nano-aAPC alone expansion, at this dose, led to 0.70% Trp2-specific cells, as determined by comparing cognate Kb-Trp2 binding to non-cognate Kb-SIINF binding (FIG. 11G). When incubated with T cells in a magnetic field, however, aAPC generated approximately 3.4% antigen specific T cells after a single week (FIG. 11G). This resulted in approximately 37,000±3,900 Trp-2 specific cells generated from a pool of $10 \times 10^6$ precursor cells in a magnetic field, compared to 6700±630 without a magnetic field (approximately 5.5-fold difference, p<0.01 by Student's t-test). With CD8 precursor frequencies estimated to be on the order of 10-800 per 10 million,[32] this suggests 450 to 3,600-fold expansion in culture with a magnetic field, comparable to the 1000-fold precursor expansion seen with viral infection in vivo.[33]

EXAMPLE 13. MAGNETIC FIELD ENHANCED T CELL ACTIVATION FOR ADOPTIVE IMMUNOTHERAPY

Figure 12B:
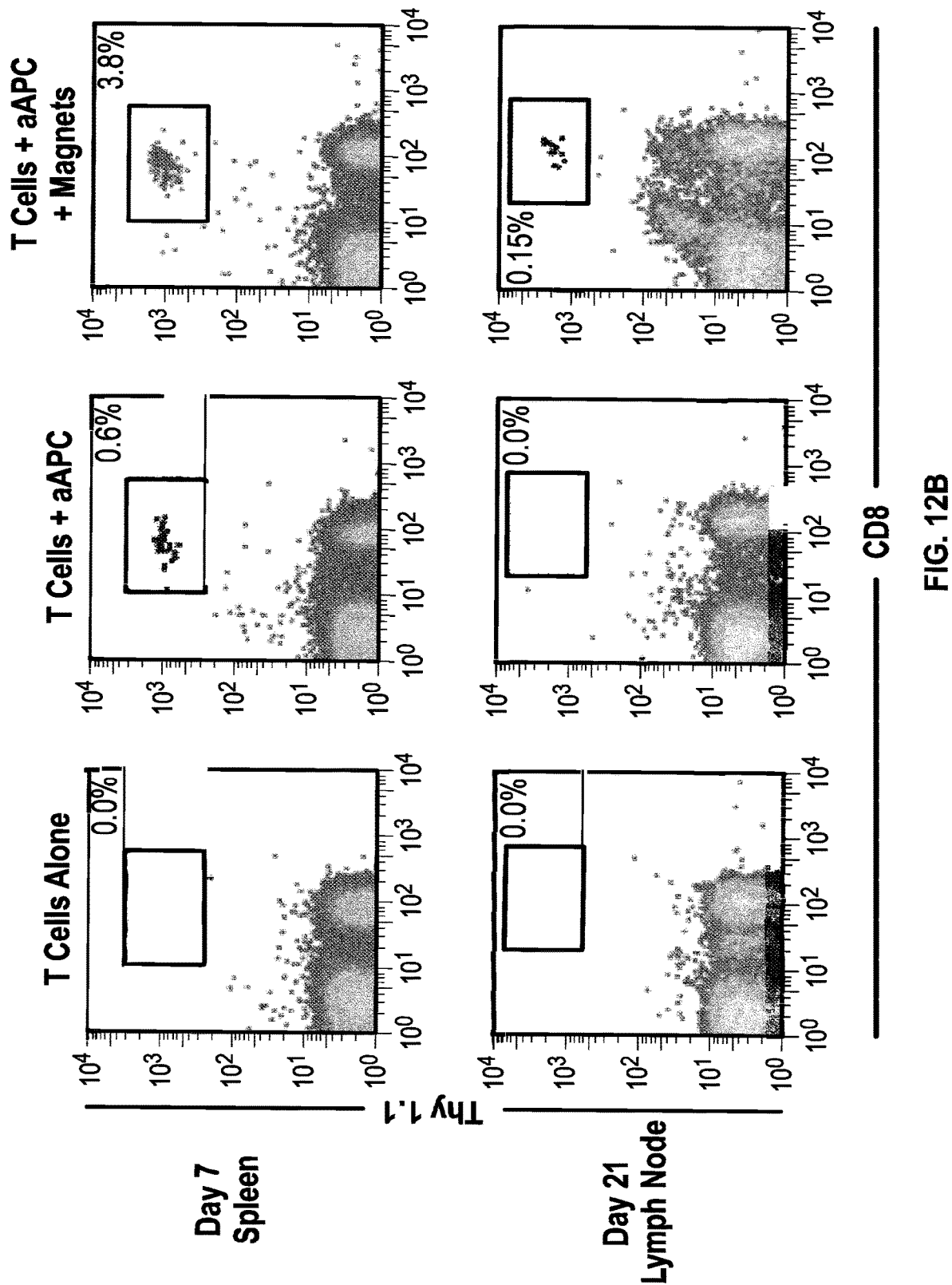

The potential for enhancing stimulation of antigen-specific cells led us to study magnetic field enhanced aAPC stimulation prior to adoptive transfer in vivo. Thy 1.1+ pmel T cells were activated in vitro with aAPC in the presence or absence of a magnetic field and adoptively transferred into wild type, Thy1.2+ recipient mice (see schematic FIG. 12A). Seven or twenty-one days after adoptive transfer, mice were sacrificed and assessed for adoptively transferred, Thy1.1+ cells.

Figure 12C:
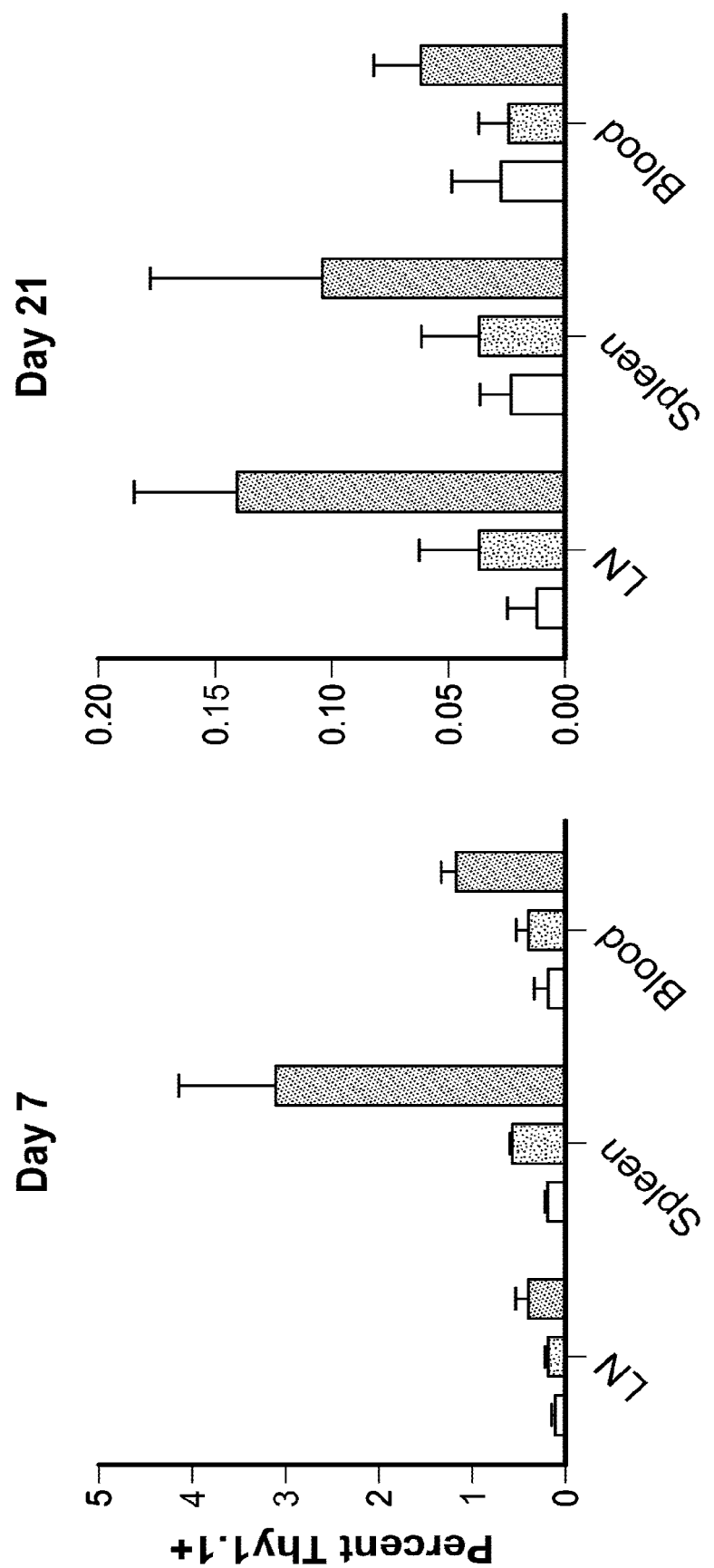
Figure 12D:
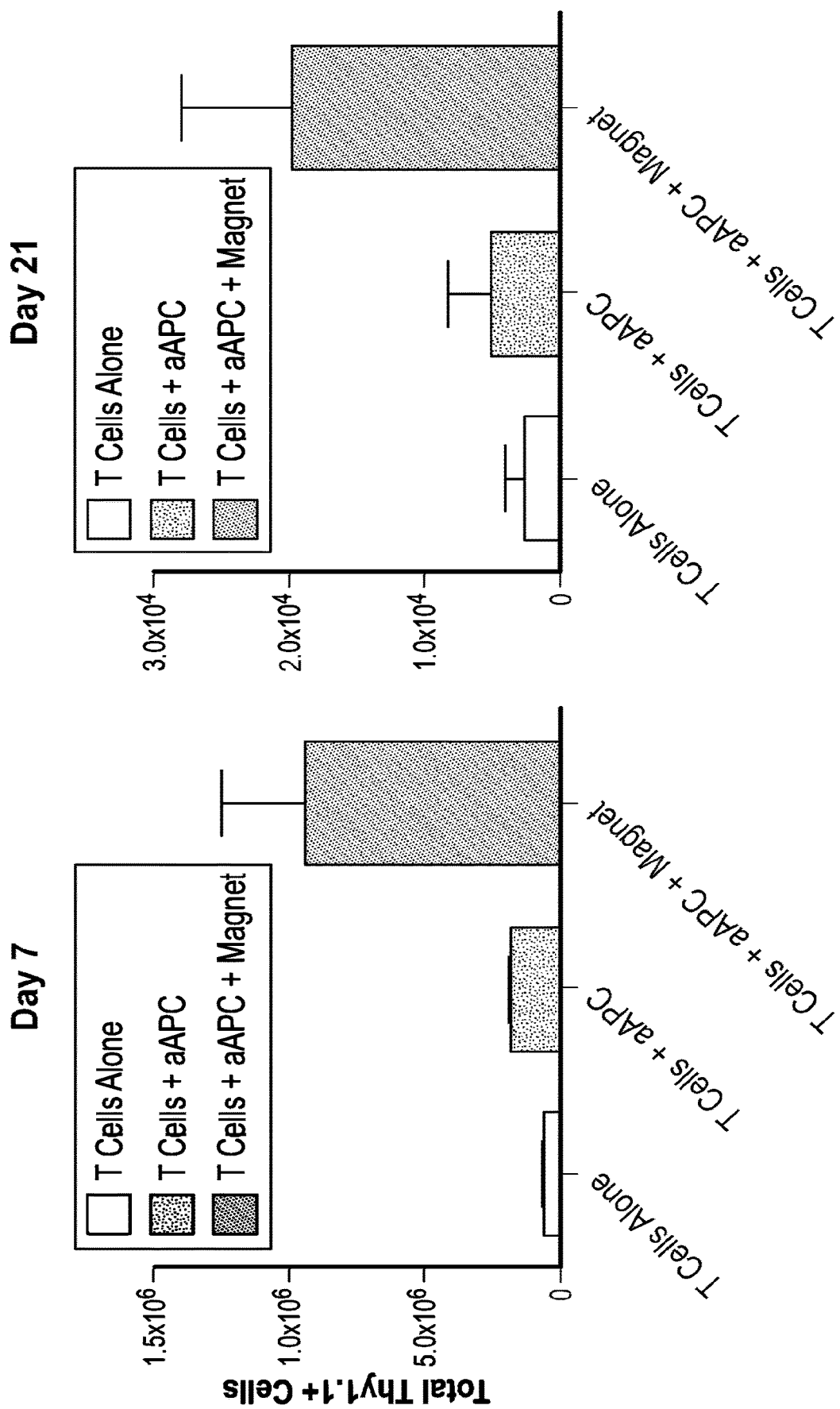

Magnetic field enhanced nano-aAPC stimulation resulted in robust expansion of the transferred T cell population. On day 7, 3.1% of T cells in the spleen were Thy1.1+ for T cells stimulated in a magnetic field, compared with 0.6% for cells stimulated with aAPC but no magnetic field, and 0.2% for untreated T cells alone that were not stimulated prior to adoptive transfer (p<0.01, FIGS. 12B-C). The largest percentage of cells was observed in the spleen on day 7 (FIG. 12C). The total Thy1.1+ cells in all organs examined reached approximately $1 \times 10^6$ for the magnetic field enhanced group (FIG. 12D) on day 7, compared to less than $2 \times 10^5$ for the no magnet group. This 5-fold enhancement was roughly consistent with the enhancement seen in vitro. While fewer cells were seen on day 21, T cells activated by aAPC in a magnetic field established a detectable population in lymph nodes (0.15%), compared to 0.04% from T cells activated by aAPC alone and 0.01% from cells that were not stimulated at all (p<0.05, FIGS. 12B-D).

Figure 12E:
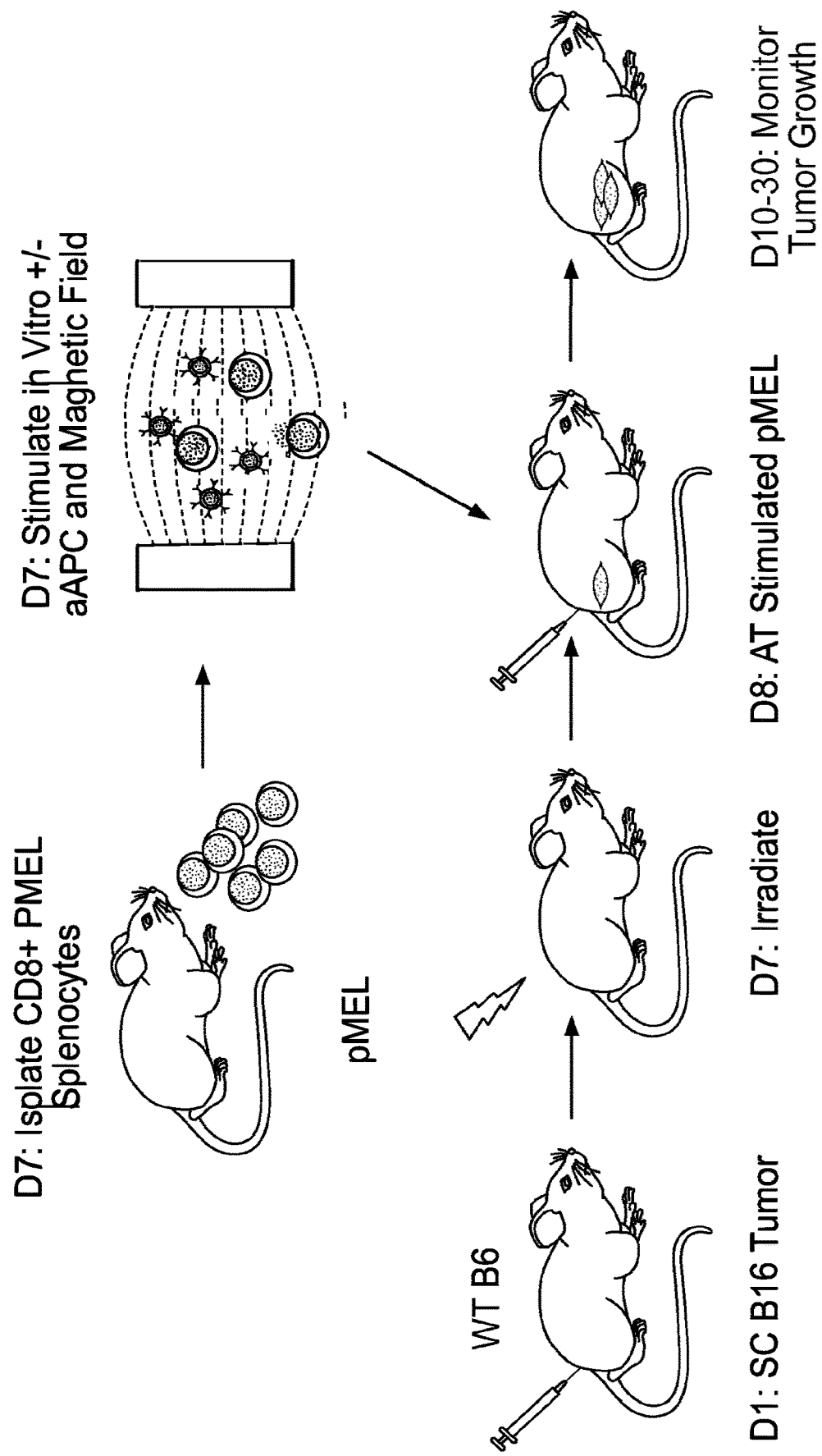

The functional consequences of magnetic field enhanced T cell stimulation were studied by treatment of B16 melanoma, a poorly immunogenic tumor with a high threshold for immune rejection.[34] Pmel T cells were adoptively transferred into mice bearing established subcutaneous B16 tumors ten days after tumor injection (FIG. 12E) and transient lymphopenia was induced by sublethal irradiation (500 cGy) of mice one day before adoptive transfer as per standard approaches to adoptive immunotherapy.[35,36]

Figure 12F:
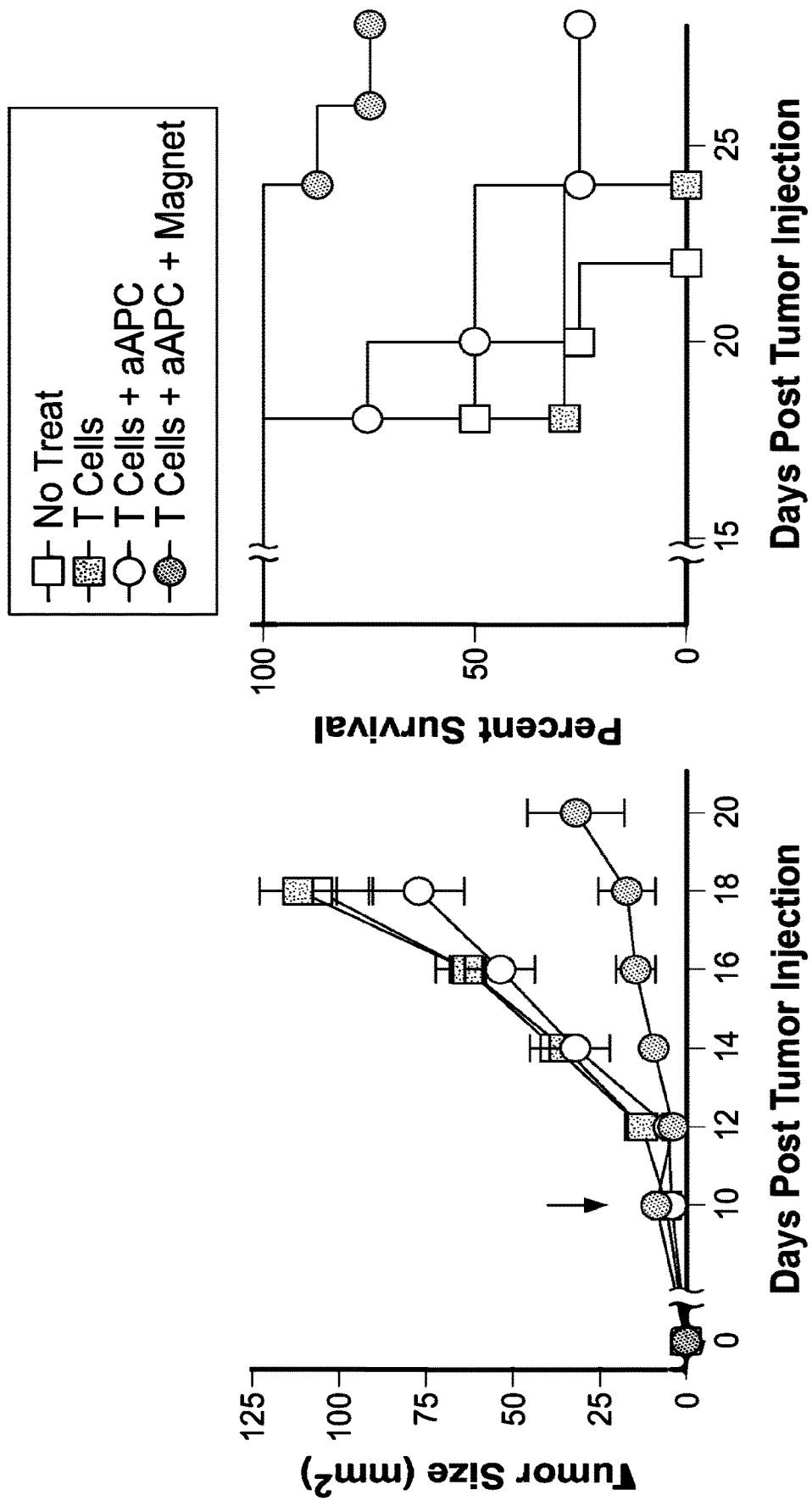

Tumor-specific T cells activated by aAPC in a magnetic field strongly inhibited tumor growth compared to no treatment controls, T cells alone and T cells stimulated by aAPC without a magnetic field (p<0.0001 treatment effect by two-way ANOVA, FIG. 12F). At day 18, mice treated with magnetic field enhanced T cells had 8 to 10-fold smaller tumors than untreated or no magnet T cell treated mice. Similarly, magnetic field enhanced T cells significantly improved host survival, with 6/8 mice surviving and 4/8 having no detectable tumor at Day 28 post injection (p<0.001, Mantel-Cox, FIG. 12F).

REFERENCES

1. Fay, F.; Scott, C. Antibody-Targeted Nanoparticles for Cancer Therapy. *Immunotherapy* 2011, 3, 381-394.
2. Moon, J. J.; Huang, B.; Irvine, D. J. Engineering Nano- and Microparticles to Tune Immunity. *Adv. Mater.* 2012, 24, 3724-46.
3. Perica, K.; León Medero, A. De; Durai, M.; Chiu, Y. L.; Bieler, J. G.; Sibener, L.; Niemöller, M.; Assenmacher, M.; Richter, A.; Edidin, M.; et al. Nanoscale Artificial Antigen Presenting Cells for T Cell Immunotherapy. *Nanomedicine* 2013, 10, 119-29.
4. Luxembourg, a T.; Brunmark, A.; Kong, Y.; Jackson, M. R.; Peterson, P. a; Sprent, J.; Cai, Z. Requirements for Stimulating Naive CD8+ T Cells Via Signal 1 Alone. I *Immunol.* 1998, 161, 5226-35.
5. Rogers, J.; Mescher, M. F. Augmentation of In Vivo Cytotoxic T Lymphocyte Activity and Reduction of Tumor Growth by Large Multivalent Immunogen. *J. Immunol.* 1992, 149, 269-76.
6. Motta, I.; Lone, Y. C.; Kourilsky, P. In Vitro Induction of Naive Cytotoxic T Lymphocytes with Complexes of Peptide and Recombinant MHC Class I Molecules Coated onto Beads: Role of TCR/ligand Density. *Eur. J. Immunol.* 1998, 28, 3685-95.
7. Merwe, P. A. van der; Dushek, O. Mechanisms for T Cell Receptor Triggering. *Nat. Rev. Immunol.* 2010, 11, 47-55.
8. Oelke, M.; Maus, M. V; Didiano, D.; June, C. H.; Mackensen, A.; Schneck, J. P. Ex Vivo Induction and Expansion of Antigen-Specific Cytotoxic T Cells by HLA-Ig-Coated Artificial Antigen-Presenting *Cells. Nat. Med.* 2003, 9, 619-24.
9. Ugel, S.; Zoso, A.; Santo, C. De; Li, Y.; Marigo, I.; Zanovello, P.; Scarselli, E.; Cipriani, B.; Oelke, M.; Schneck, J. P.; et al. In Vivo Administration of Artificial Antigen-Presenting Cells Activates Low-Avidity T Cells for Treatment of Cancer. *Cancer Res.* 2009, 69, 9376-84.

10. Oelke, M.; Schneck, J. P. Overview of a HLA-Ig Based "Lego-Like System" for T Cell Monitoring, Modulation and Expansion. *Immunol. Res.* 2010, 47, 248-56.
11. Steenblock, E.; Wrzesinski, S.; Flavell, R.; Fahmy, T. Antigen Presentation on Artificial Acellular Substrates: Modular Systems for Flexible, Adaptable Immunotherapy. *Expert Opin. Biol. Ther.* 2009, 9(4) 451-464.
12. Nel, A. E.; Madler, L.; Velegol, D.; Xia, T.; Hoek, E. M. V; Somasundaran, P.; Klaessig, F.; Castranova, V.; Thompson, M. Understanding Biophysicochemical Interactions at the Nano-Bio Interface. *Nat. Mater.* 2009, 8, 543-57.
13. Fahmy, T. M.; Bieler, J. G.; Edidin, M.; Schneck, J. P. Increased TCR Avidity after T Cell Activation: a Mechanism for Sensing Low-Density Antigen. *Immunity* 2001, 14, 135-43.
14. Kumar, R.; Ferez, M.; Swamy, M.; Arechaga, I.; Rejas, M. T.; Valpuesta, J. M.; Schamel, W. W. a; Alarcon, B.; Santen, H. M. van Increased Sensitivity of Antigen-Experienced T Cells through the Enrichment of Oligomeric T Cell Receptor Complexes. *Immunity* 2011, 35, 375-87.
15. Boyle, S.; Kolin, D. L.; Bieler, J. G.; Schneck, J. P.; Wiseman, P. W.; Edidin, M. Quantum Dot Fluorescence Characterizes the Nanoscale Organization of T Cell Receptors for Antigen. *Biophys. J.* 2011, 101, L57-L59.
16. Perica, K.; Bieler, J. G.; Edidin, M.; Schneck, J. Modulation of MHC Binding by Lateral Association of TCR and Coreceptor. *Biophys. J.* 2012, 103, 1890-8.
17. Lillemeier, B. F.; Mortelmaier, M. a; Forstner, M. B.; Huppa, J. B.; Groves, J. T.; Davis, M. M. TCR and Lat Are Expressed on Separate Protein Islands on T Cell Membranes and Concatenate During Activation. *Nat. Immunol.* 2010, 11, 90-6.
18. Varma, R.; Campi, G.; Yokosuka, T.; Saito, T.; Dustin, M. L. T Cell Receptor-Proximal Signals Are Sustained in Peripheral Microclusters and Terminated in the Central Supramolecular Activation Cluster. *Immunity* 2006, 25, 117-127.
19. Lee, J.-H.; Kim, E. S.; Cho, M. H.; Son, M.; Yeon, S.-I.; Shin, J.-S.; Cheon, J. Artificial Control of Cell Signaling and Growth by Magnetic Nanoparticles. *Angew. Chem. Int. Ed. Engl.* 2010, 49, 5698-702.
20. Mannix, R. J.; Kumar, S.; Cassiola, F.; Montoya-Zavala, M.; Feinstein, E.; Prentiss, M.; Ingber, D. E. Nanomagnetic Actuation of Receptor-Mediated Signal Transduction. *Nat. Nanotechnol.* 2008, 3, 36-40.
21. Cho, M. H.; Lee, E. J.; Son, M.; Lee, J.-H.; Yoo, D.; Kim, J.-W.; Park, S. W.; Shin, J.-S.; Cheon, J. A Magnetic Switch for the Control of Cell Death Signalling in In Vitro and In Vivo Systems. *Nat. Mater.* 2012, 11, 1038-1043.
22. Smith-Garvin, J. E.; Koretzky, G. a; Jordan, M. S. T Cell Activation. *Annu. Rev. Immunol.* 2009, 27, 591-619.
23. Kunzmann, A.; Andersson, B.; Thurnherr, T.; Krug, H.; Scheynius, A.; Fadeel, B. Toxicology of Engineered Nanomaterials: Focus on Biocompatibility, Biodistribution and Biodegradation. *Biochim. Biophys. Acta* 2010, 1810, 361-373.
24. Turtle, C. J.; Riddell, S. R. Artificial Antigen-Presenting Cells for Use in Adoptive Immunotherapy. 2010, 16.
25. Gunn, J.; Wallen, H.; Veiseh, O.; Sun, C.; Fang, C.; Cao, J.; Yee, C.; Zhang, M. A Multimodal Targeting Nanoparticle for Selectively Labeling T Cells. *Small* 2008, 4, 712-5.
26. Fahmy, T. M.; Bieler, J. G.; Schneck, J. P. Probing T Cell Membrane Organization Using Dimeric MHC-Ig Complexes. *J Immunol. Methods* 2002, 268, 93-106.
27. Dobson, J. Remote Control of Cellular Behaviour with Magnetic Nanoparticles. *Nat. Nanotechnol.* 2008, 3, 139-43.
28. James, J. R.; Vale, R. D. Biophysical Mechanism of T-Cell Receptor Triggering In a Reconstituted System. *Nature* 2012, 487, 64-9.
29. Hughes, S.; Haj, A. J. El; Dobson, J. Magnetic Micro- and Nanoparticle Mediated Activation of Mechanosensitive Ion Channels. *Med. Eng. Phys.* 2005, 27, 754-62.
30. Lim, T. S.; Mortellaro, A.; Lim, C. T.; Hammerling, G. J.; Ricciardi-Castagnoli, P. Mechanical Interactions Between Dendritic Cells and T Cells Correlate with T Cell Responsiveness. *J. Immunol.* 2011, 187, 258-65.
31. Husson, J.; Chemin, K.; Bohineust, A.; Hivroz, C.; Henry, N. Force Generation Upon T Cell Receptor Engagement. *PLoS One* 2011, 6, e19680.
32. Jenkins, M. K.; Moon, J. J. The Role of Naive T Cell Precursor Frequency and Recruitment in Dictating Immune Response Magnitude. *J. Immunol.* 2012, 188, 4135-4140.
33. Blattman, J. N.; Antia, R.; Sourdive, D. J. D.; Wang, X.; Kaech, S. M.; Murali-Krishna, K.; Altman, J. D.; Ahmed, R. Estimating the Precursor Frequency of Naive Antigen-Specific CD8 T Cells. *J. Exp. Med.* 2002, 195, 657-64.
34. Klebanoff, C. a; Gattinoni, L.; Palmer, D. C.; Muranski, P.; Ji, Y.; Hinrichs, C. S.; Borman, Z. a; Kerkar, S. P.; Scott, C. D.; Finkelstein, S. E.; et al. Determinants of Successful CD8+ T-Cell Adoptive Immunotherapy for Large Established Tumors in Mice. *Clin. Cancer Res.* 2011, 17, 5343-52.
35. Wrzesinski, C.; Paulos, C. M.; Kaiser, A.; Muranski, P.; Palmer, D. C.; Gattinoni, L.; Yu, Z.; Rosenberg, S. a; Restifo, N. P. Increased Intensity Lymphodepletion Enhances Tumor Treatment Efficacy of Adoptively Transferred Tumor-Specific T Cells. *J. Immunother.* 2010, 33, 1-7.
36. Restifo, N. P.; Dudley, M. E.; Rosenberg, S. a Adoptive Immunotherapy for Cancer: Harnessing the T Cell Response. *Nat. Rev. Immunol.* 2012, 12, 269-81.
37. Naahidi, S.; Jafari, M.; Edalat, F.; Raymond, K.; Khademhosseini, A.; Chen, P. Biocompatibility of Engineered Nanoparticles for Drug Delivery. *J. Control. Release* 2013, 166, 182-94.
38. Griitzkau, A.; Radbruch, A. Small but Mighty: How the MACS-Technology Based on Nanosized Superparamagnetic Particles Has Helped to Analyze the Immune System Within the Last 20 Years. *Cytometry. A* 2010, 77, 643-7.
39. Dvorak, C. C.; Gilman, a L.; Horn, B.; Oon, C.-Y.; Dunn, E. a; Baxter-Lowe, L. a; Cowan, M. J. Positive Selection and Transplantation of Autologous Highly Purified CD133(+) Stem Cells in Resistant/relapsed Chronic Lymphocytic Leukemia Patients Results in Rapid Hematopoietic Reconstitution Without an Adequate Leukemic Cell Purging. *Bone Marrow Transplant.* 2013, 48, 508-13.
40. Cheng, K.; Malliaras, K.; Li, T.-S.; Sun, B.; Houde, C.; Galang, G.; Smith, J.; Matsushita, N.; Marban, E. Magnetic Enhancement of Cell Retention, Engraftment, and Functional Benefit after Intracoronary Delivery of Cardiac-Derived Stem Cells in a Rat Model of Ischemia/reperfusion. *Cell Transplant.* 2012, 21, 1121-35.
41. Kobayashi, T.; Ochi, M.; Yanada, S.; Ishikawa, M.; Adachi, N.; Deie, M.; Arihiro, K. A Novel Cell Delivery System Using Magnetically Labeled Mesenchymal Stem Cells and an External Magnetic Device for Clinical Cartilage Repair. *Arthroscopy* 2008, 24, 69-76.

42. Arbab, A. S.; Jordan, E. K.; Wilson, L. B.; Yocum, G. T.; Lewis, B. K.; Frank, J. a In Vivo Trafficking and Targeted Delivery of Magnetically Labeled Stem Cells. *Hum. Gene Ther.* 2004, 15, 351-60.
43. Hinrichs, C. S.; Borman, Z. a; Gattinoni, L.; Yu, Z.; Burns, W. R.; Huang, J.; Klebanoff, C. a; Johnson, L. a; Kerkar, S. P.; Yang, S.; et al. Human Effector CD8+ T Cells Derived from Naive Rather Than Memory Subsets Possess Superior Traits for Adoptive Immunotherapy. *Blood* 2011, 117, 808-14.
44. Hinrichs, C. S.; Borman, Z. a; Cassard, L.; Gattinoni, L.; Spolski, R.; Yu, Z.; Sanchez-Perez, L.; Muranski, P.; Kern, S. J.; Logun, C.; et al. Adoptively Transferred Effector Cells Derived from Naive Rather Than Central Memory CD8+ T Cells Mediate Superior Antitumor Immunity. *Proc. Natl. Acad. Sci. U.S.A* 2009, 106, 17469-74.
45. Klebanoff, C. a; Gattinoni, L.; Restifo, N. P. Sorting through Subsets: Which T-Cell Populations Mediate Highly Effective Adoptive Immunotherapy? *J. Immunother.* 2012, 35, 651-60.
46. Durai, M.; Krueger, C.; Ye, Z.; Cheng, L.; Mackensen, A.; Oelke, M.; Schneck, J. P. In Vivo Functional Efficacy of Tumor-Specific T Cells Expanded Using HLA-Ig Based Artificial Antigen Presenting Cells (aAPC). *Cancer Immunol. Immunother.* 2009, 58, 209-20.

The invention claimed is:

1. A method of activating T cells, comprising incubating in the presence of a magnetic field a population of T cells with paramagnetic nanoparticles comprising:
   at least one T cell costimulatory molecule on the surface of the paramagnetic nanoparticles; and
   at least one MHC antigen presenting complex that comprises at least one MHC class II peptide binding cleft having a peptide antigen bound thereto;
   wherein the activated T cells are helper T cells; and
   wherein the paramagnetic nanoparticles are 50-500 nm in mean diameter.

2. The method of claim 1, wherein the population of T cells are incubated with the paramagnetic nanoparticles for 10 minutes to 3 days.

3. The method of claim 1, wherein the T cell costimulatory molecule is an antibody that binds CD28.

4. The method of claim 1, wherein the paramagnetic nanoparticles are 50-100 nm in mean diameter.

5. The method of claim 1, wherein the peptide antigen is selected from the group consisting of a peptide of a tumor-associated antigen and a peptide of an infectious agent antigen.

6. The method of claim 5, wherein the peptide antigen is an infectious agent antigen.

7. The method of claim 5, wherein the infectious agent antigen is selected from protozoan, bacteria, viruses, prions, fungi, parasites, intracellular parasites, and helminths.

8. The method of claim 7, wherein the protozoan antigen is selected from antigens of malarial plasmodia, *Leishmania* species, *Trypanosoma* species and *Schistosoma* species.

9. The method of claim 7, wherein the bacterial antigen is selected from antigens of gram-positive cocci, gram-positive bacilli, gram-negative bacteria, anaerobic bacteria, Actinomycetaceae, Bacillaceae, Bartonellaceae, Bordetellae, Captophagaceae, Corynebacteriaceae, Enterobacteriaceae, Legionellaceae, Micrococcaceae, Mycobacteriaceae, Pasteurellaceae, Pseudomonadaceae, Spirochaetaceae, Vibrionaceae, Nocardiaceae, *Acinetobacter, Brucella, Campylobacter, Erysipelothrix, Ewingella, Francisella, Gardnerella, Helicobacter, Levinea, Listeria, Streptobacillus*, and *Tropheryma*.

10. The method of claim 7, wherein the viral antigen is selected from antigens of adenovirus, herpes simplex virus, papilloma virus, respiratory syncytial virus, poxviruses, HIV, influenza viruses, and CMV.

11. The method of claim 1, wherein the population of T cells are obtained from peripheral blood mononuclear cells, bone marrow, lymph node tissue, spleen tissue, or tumor tissue.

12. The method of claim 1, wherein the population of T cells are obtained by apheresis or leukapheresis.

13. The method of claim 1, further comprising administering the activated T cells to a patient, wherein the patient has an infectious disease, or is immunosuppressed.

14. The method of claim 13, wherein the population of T cells are obtained from the patient.

15. The method of claim 13, wherein the population of T cells are obtained from a donor who is not the patient.

16. The method of claim 1, wherein the paramagnetic nanoparticles are iron dextran particles.

* * * * *

SEQUENCE LISTING

```
<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Synthetic sequence

<400> SEQUENCE: 1

Gly Gly Gly Thr Ser Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic sequence

<400> SEQUENCE: 2

Gly Ser Leu Gly Gly Ser
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic sequence

<400> SEQUENCE: 3

Ser Ile Tyr Arg Tyr Tyr Gly Leu
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic sequence

<400> SEQUENCE: 4

Ser Ile Ile Asn Phe Glu Lys Leu
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic sequence
```

```
<400> SEQUENCE: 5

Lys Val Pro Arg Asn Gln Asp Trp Leu
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic sequence

<400> SEQUENCE: 6

Ala Ser Asn Glu Asn Met Glu Thr His
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic sequence

<400> SEQUENCE: 7

Gly Ile Leu Gly Phe Val Phe Thr Leu
1               5
```